(12) United States Patent
Sugawara et al.

(10) Patent No.: US 11,981,794 B2
(45) Date of Patent: May 14, 2024

(54) CURABLE COMPOSITION, CURED PRODUCT, AND COMPOUND

(71) Applicant: TOKYO OHKA KOGYO CO., LTD., Kawasaki (JP)

(72) Inventors: Ryutaro Sugawara, Kawasaki (JP); Masato Miyazaki, Kawasaki (JP); Takuro Asaba, Kawasaki (JP)

(73) Assignee: TOKYO OHKA KOGYO CO., LTD., Kawasaki (JP)

( * ) Notice: Subject to any disclaimer, the term of this patent is extended or adjusted under 35 U.S.C. 154(b) by 104 days.

(21) Appl. No.: 17/457,104

(22) Filed: Dec. 1, 2021

(65) Prior Publication Data

US 2022/0177673 A1 Jun. 9, 2022

(30) Foreign Application Priority Data

Dec. 3, 2020 (JP) ................. 2020-201364

(51) Int. Cl.
 *C08K 5/3492* (2006.01)
 *C08K 5/06* (2006.01)

(52) U.S. Cl.
 CPC .............. *C08K 5/3492* (2013.01); *C08K 5/06* (2013.01)

(58) Field of Classification Search
 CPC .................................................. C08K 5/3492
 See application file for complete search history.

(56) References Cited

U.S. PATENT DOCUMENTS

2017/0002124 A1* 1/2017 Ishiyama ............. C07D 277/66
2020/0116896 A1 4/2020 Kaneko et al.

FOREIGN PATENT DOCUMENTS

WO WO 2018/230595 A1 12/2018

* cited by examiner

*Primary Examiner* — Wenwen Cai
(74) *Attorney, Agent, or Firm* — Knobbe, Martens, Olson & Bear, LLP

(57) ABSTRACT

A curable composition that can contain a high concentration of a heterocyclic compound (A) having a triazine ring as a component which gives a cured product exhibiting a high refractive index, surface without defects such as roughness or cracks, and is unlikely to have cracks occurring on the surface thereof even when exposed to a high-temperature and high-humidity environment, a cured product of the curable composition, and a compound that may be blended to the curable composition. As a component of the composition, a triazine compound having a structure in which an optionally substituted monocyclic aromatic group(s) or an optionally substituted condensed aromatic group(s) is/are bonded to the triazine ring via an amino group, and, as a solvent, triethylene glycol dimethyl ether are used in combination.

10 Claims, No Drawings

CURABLE COMPOSITION, CURED PRODUCT, AND COMPOUND

This application claims priority to Japanese Patent Application No. 2020-201364, filed Dec. 3, 2020, the entire content of which is incorporated herein by reference.

BACKGROUND OF THE INVENTION

Field of the Invention

The present invention relates to a curable composition, a cured product of the curable composition, and a compound that may be blended to the curable composition mentioned above.

Related Art

High refractive index materials have been conventionally used for formation of optical members. As a composition for forming a high refractive index material, for example, there has been suggested a curable composition including a triazine derivative having a specific structure, a polymerizable compound, a resin, and a photopolymerization initiator (see Patent Document 1). Use of the curable composition described in Patent Document 1 enables a cured product having a high refractive index to be formed.
Patent Document 1: PCT International Publication No.

SUMMARY OF THE INVENTION

Use of the curable composition described in Patent Document 1 enables a cured product having a high refractive index to be formed, as described above. However, high refractive index materials are required to have a higher refractive index. In this respect, in the curable composition described in Patent Document 1, when the content of the triazine derivative is increased, the cured product is expected to have a higher refractive index. The triazine derivative disclosed in Patent Document 1, however, does not necessarily have a high solubility in an organic solvent. High refractive index materials are often used in optical members, as described above. Optical members are usually required to have a surface without defects such as surface roughness or cracks. When the curable composition described in Patent Document 1 is used, however, defects such as roughness or cracks often occur on the surface of a cured product. Moreover, when a cured product of the curable composition described in Patent Document 1 is exposed to a high-temperature-and-high-humidity environment for a long time, cracks or blisters may occur on the surface of the cured product.

The present invention has been made in view of the above problems, and an object thereof is to provide a curable composition that can contain a high concentration of a heterocyclic compound (A) having a triazine ring, as a component increasing the refractive index of a cured product, and that gives a cured product exhibiting a high refractive index, having a surface without defects such as roughness or cracks, and being unlikely to have cracks or the like occurring on the surface thereof even when exposed to a high-temperature-and-high-humidity environment, a cured product of the curable composition, and a compound that may be blended to the curable composition mentioned above.

The present inventors have found that the above-mentioned problems can be solved by using, as a component of a curable composition, a triazine compound having a structure in which an optionally substituted monocyclic aromatic group(s) or an optionally substituted condensed aromatic group(s) is/are bonded to the triazine ring via an amino group, and, as a solvent, triethylene glycol dimethyl ether, in combination, and accomplished the present invention. Specifically, the present invention provides the followings.

A first aspect of the present invention relates to a curable composition comprising a heterocyclic compound (A), an initiator (C), and a solvent (S), wherein the heterocyclic compound (A) is a compound represented by the following formula (A1):

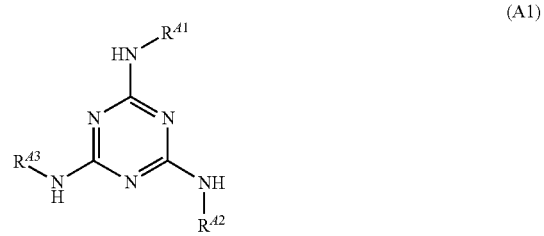

wherein $R^{A1}$, $R^{A2}$, and $R^{A3}$ are each independently an optionally substituted monocyclic aromatic group or an optionally substituted condensed aromatic group, when the monocyclic aromatic group or the condensed aromatic group has a substituent, the substituent does not contain an aromatic ring, and three —NH— groups bonded to the triazine ring each are bonded to the aromatic ring in the $R^{A1}$, the $R^{A2}$, and the $R^{A3}$;

when the heterocyclic compound (A) has a polymerizable group, the curable composition comprises or does not comprise a polymerizable compound (B) other than the heterocyclic compound (A);

when the heterocyclic compound (A) has no polymerizable group, the curable composition comprises a polymerizable compound (B) other than the heterocyclic compound (A);

the polymerizable group is a radically polymerizable group-containing group or a cationically polymerizable group-containing group;

when the curable composition comprises the heterocyclic compound (A) having the polymerizable group and the polymerizable compound (B), the polymerizable group possessed by the heterocyclic compound (A) and the polymerizable group possessed by the polymerizable compound (B) each are a radically polymerizable group-containing group or a cationically polymerizable group-containing group; and the solvent (S) comprises triethylene glycol dimethyl ether.

A second aspect of the present invention relates to a cured product of the curable composition according to the first aspect.

A third aspect of the present invention relates to a compound represented by the following formula (A1):

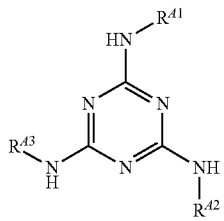

(A1)

wherein one or two of $R^{A1}$, $R^{A2}$, $R^{A3}$ is/are an optionally substituted naphthyl group(s), and one or two of the $R^{A1}$, the $R^{A2}$, and the $R^{A3}$ is/are a 4-cyanophenyl group(s) or a benzothiazolyl group(s).

The present invention can provide a curable composition that can contain a high concentration of a heterocyclic compound (A) having a triazine ring, as a component increasing the refractive index of a cured product, and that gives a cured product exhibiting a high refractive index, having a surface without defects such as roughness or cracks, and being unlikely to have cracks or the like occurring on the surface thereof even when exposed to a high-temperature-and-high-humidity environment, a cured product of the curable composition, and a compound that may be blended to the curable composition mentioned above.

DETAILED DESCRIPTION OF THE INVENTION

<<Curable Composition>>

The curable composition includes a heterocyclic compound (A), which is a compound represented by the formula (A1) mentioned below, an initiator (C), and a solvent (S). When the curable composition includes the compound represented by the following formula (A1), curing the curable composition enables a cured product to be formed, the cured product exhibiting a high refractive index, having a surface without defects such as roughness or cracks, and being unlikely to have cracks or the like occurring on the surface thereof even when exposed to a high-temperature-and-high-humidity environment. Additionally, when the curable composition includes the compound represented by the formula (A1), the cured product of the curable composition also has excellent heat resistance.

The curable composition further includes triethylene glycol dimethyl ether as the solvent (S). The compound represented by the formula (A1) dissolves favorably in the solvent (S). If the content of the compound represented by the formula (A1) in the curable composition can be increased, a cured product of the curable composition is expected to have a higher refractive index.

When the heterocyclic compound (A) has a polymerizable group, the curable composition includes or does not include a polymerizable compound (B) other than the heterocyclic compound (A). When the heterocyclic compound (A) has no polymerizable group, the curable composition includes a polymerizable compound (B) other than the heterocyclic compound (A). The polymerizable group is a radically polymerizable group-containing group or a cationically polymerizable group-containing group, and when the curable composition includes a heterocyclic compound (A) having a polymerizable group and a polymerizable compound (B), the polymerizable group possessed by the heterocyclic compound (A) and the polymerizable group possessed by the polymerizable compound (B) each are a radically polymerizable group-containing group or a cationically polymerizable group-containing group.

Hereinafter, essential or optional components that may be included in the curable composition will be described.

<Heterocyclic Compound (A)>

The curable composition includes a compound represented by the following formula (A1) as the heterocyclic compound (A).

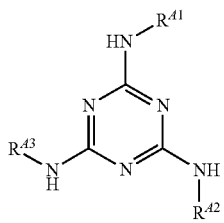

(A1)

$R^{A1}$, $R^{A2}$, and $R^{A3}$ are each independently an optionally substituted monocyclic aromatic group or an optionally substituted condensed aromatic group. when the monocyclic aromatic group or the condensed aromatic group has a substituent, the substituent does not contain an aromatic ring. Three —NH— groups bonded to the triazine ring each are bonded to the aromatic ring in the $R^{A1}$, the $R^{A2}$, and the $R^{A3}$.

The monocyclic aromatic group as $R^{A1}$, $R^{A2}$, and $R^{A3}$ may be an aromatic hydrocarbon group or a aromatic heterocyclic group. Examples of the monocyclic aromatic ring include a phenyl group, a pyridinyl group, a pyrazinyl group, a pyridazinyl group, a furanyl group, a thienyl group, an oxazolyl group, a thiazolyl group, and the like.

Examples of the substituent which may be possessed by the monocyclic aromatic group include a halogen atom, a hydroxy group, a mercapto group, a cyano group, a nitro group, and a monovalent organic group. However, the monovalent organic group does not include an aromatic ring. Examples of the halogen atom include a chlorine atom, a bromine atom and a fluorine atom. Examples of the monovalent organic group include an alkyl group, an alkoxy group, an alkoxyalkyl group, an aliphatic acyl group, an aliphatic acyloxy group, an alkoxycarbonyl group, an alkylthio group, an aliphatic acylthio group, and the like. A radically polymerizable group-containing group and a cationically polymerizable group-containing group described below are also preferred as the monovalent organic group.

The monovalent organic group as substituent is not particularly limited as long as the desired effect is not impaired. The number of carbon atoms of the monovalent organic group as substituent is, for example, preferably 1 or more and 20 or less, more preferably 1 or more and 12 or less, and further preferably 1 or more and 8 or less. A lower limit of the number of carbon atoms of the alkoxyalkyl group, the aliphatic acyl group, the aliphatic acyloxy group, the alkoxycarbonyl group, the alkoxyalkylthio group, and the aliphatic acylthio group is 2.

Suitable examples of the alkyl group as substituent include a methyl group, an ethyl group, an n-propyl group, an isopropyl group, an n-butyl group, an isobutyl group, a sec-butyl group, a tert-butyl group, an n-pentyl group, an n-hexyl group, an n-heptyl group, and an n-octyl group.

Suitable examples of the alkoxy group as substituent include a methoxy group, an ethoxy group, an n-propyloxy group, an isopropyloxy group, an n-butyloxy group, an isobutyloxy group, a sec-butyloxy group, a tert-butyloxy group, an n-pentyloxy group, an n-hexyloxy group, an n-heptyloxy group an n-octyloxy group.

Suitable examples of the alkoxyalkyl group as substituent include a methoxymethyl group, an ethoxymethyl group, an n-propyloxymethyl group, an n-butyloxymethyl group, a 2-methoxyethyl group, a 2-ethoxyethyl group, a 2-n-propyloxyethyl group, a 2-n-butyloxyethyl group, a 3-methoxy-n-propyloxy group, a 3-ethoxy-n-propyloxy group, a 3-n-propyloxy-n-propyloxy group, a 3-n-butyloxy-n-propyloxy group, a 4-methoxy-n-butyloxy group, a 4-ethoxy-n-butyloxy group, a 4-n-propyloxy-n-butyloxy group, and a 4-n-butyloxy-n-butyloxy group.

Suitable examples of the aliphatic acyl group as substituent include an acetyl group, a propionyl group, a butanoyl group, a pentanoyl group, a hexanoyl group, a heptanoyl group, and an octanoyl group.

Suitable examples of the aliphatic acyloxy group as substituent include an acetoxy group, a propionyloxy group, a butanoyloxy group, a pentanoyloxy group, a hexanoyloxy group, a heptanoyloxy group, and an octanoyloxy group.

Suitable examples of the alkoxycarbonyl group as substituent include a methoxycarbonyl group, an ethoxycarbonyl group, an n-propyloxycarbonyl group, an isopropyloxycarbonyl group, an n-butyloxycarbonyl group, an isobutyloxycarbonyl group, a sec-butyloxycarbonyl group, a tert-butyloxycarbonyl group, an n-pentyloxycarbonyl group, an n-hexyloxycarbonyl group, an n-heptyloxycarbonyl group, and an n-octyloxycarbonyl group.

Suitable examples of the alkylthio group as substituent include a methylthio group, an ethylthio group, an n-propylthio group, an isopropylthio group, an n-butylthio group, a sec-butylthio group, a tert-butylthio group, an n-pentylthio group, an n-hexylthio group, an n-heptylthio group, and an n-octylthio group.

Suitable examples of the aliphatic acylthio group include an acetylthio group, a propionylthio group, a butanoylthio group, a pentanoylthio group, a hexanoylthio group, a heptanoylthio group, and an ocatnoylthio group.

When the monocyclic aromatic group has a substituent(s), the number of substituents is not particularly limited as long as the desired effects are not impaired. When the monocyclic aromatic group has a substituent(s), the number of substituents is preferably 1 or more and 4 or less, more preferably 1 or 2, and particularly preferably 1. When the monocyclic aromatic group has a plurality of substituents, the plurality of substituents may be different from each other.

Examples of the optionally substituted monocyclic aromatic group described above include a phenyl group, a 4-cyanophenyl group, a 3-cyanophenyl group, a 2-cyanophenyl group, a 2,3-dicyanophenyl group, a 2,4-dicyanophenyl group, a 2,5-dicyanophenyl group, a 2,6-dicyanophenyl group, a 3,4-dicyanophenyl group, a 3,5-dicyanophenyl group, a 4-nitrophenyl group, a 3-nitrophenyl group, a 2-nitrophenyl group, a 4-chlorophenyl group, a 3-chlorophenyl group, a 2-chlorophenyl group, a 4-bromophenyl group, a 3-bromophenyl group, a 2-bromophenyl group, a 4-iodophenyl group, a 3-iodophenyl group, a 2-iodophenyl group, a 4-methoxyphenyl group, a 3-methoxyphenyl group, a 2-methoxyphenyl group, a 4-methylphenyl group, a 3-methylphenyl group, and a 2-methylphenyl group. A phenyl group having a radically polymerizable group-containing group or a cationically polymerizable group-containing group at 4-position, 3-position, or 4-position preferred as the monocyclic aromatic group.

Among these, the phenyl group, the 4-cyanophenyl group, the 3-cyanoohenyl group, the 2-cyanophenyl group, the 4-nitrophenyl group, the 3-nitrophenyl group, the 2-nitrophenyl group, and the phenyl group having a radically polymerizable group-containing group or a cationically polymerizable group-containing group at 4-position, 3-position, or 4-position are preferred, and the phenyl group, the 4-cyanophenyl group, having a radically polymerizable group-containing group or a cationically polymerizable group-containing group at 4-position, 3-position, or 4-position are more preferred.

The condensed aromatic group as $R^{41}$, $R^{42}$, and $R^{43}$ is a group obtained by removal of one hydrogen atom from a condensed polycyclic ring obtained by condensation of two or more aromatic monocycles. The number of aromatic monocycles constituting the condensed aromatic group is not particularly limited. The number of aromatic monocycles constituting the condensed aromatic group is preferably 2 or 3, and more preferably 2. That is, as the condensed aromatic group, a bicyclic condensed aromatic group or a tricyclic condensed aromatic group is preferred, and a bicyclic condensed aromatic group is more preferred. The condensed aromatic group may be an aromatic hydrocarbon group or an aromatic heterocyclic group.

As the bicyclic condensed aromatic group, for example, a naphthalene-1-yl group, a naphthalene-2-yl group, a quinoline-2-yl group, a quinoline-3-yl group, a quinoline-4-yl group, a quinoline-5-yl group, a quinoline-6-yl group, a quinoline-7-yl group, a quinoline-8-yl group, an isoquinoline-1-yl group, an isoquinoline-3-yl group, an isoquinoline-4-yl group, an isoquinoline-5-yl group, an isoquinoline-6-yl group, an isoquinoline-7-yl group, an isoquinoline-8-yl group, a benzoxazole-2-yl group, a benzoxazole-4-yl group, a benzoxazole-5-yl group, a benzoxazole-6-yl group, a benzoxazole-7-yl group, a benzothiazole-2-yl group, a benzothiazole-4-yl group, a benzothiazole-5-yl group, a benzothiazole-6-yl group, a benzothiazole-7-yl group, and the like are exemplified.

As the tricyclic condensed aromatic group, for example, an anthracene-1-yl group, an anthracene-2-yl group, an anthracene-9-yl group, a phenanthrene-1-yl group, a phenanthrene-2-yl group, a phenanthrene-3-yl group, a phenanthrene-4-yl group, a phenanthrene-9-yl group, an acridine-1-yl group, an acridine-2-yl group, an acridine-3-yl group, an acridine-4-yl group, and an acridine-9-yl group are exemplified.

A substituent which may be possessed by the polycyclic condensed aromatic group such as the bicyclic condensed aromatic group and the tricyclic condensed aromatic group is the same as the substituent which may be possessed by the monocyclic aromatic group.

As the optionally substituted condensed aromatic group described above, the naphthalene-1-yl group, the naphthalene-2-yl group, the quinoline-2-yl group, the quinoline-3-yl group, the quinoline-4-yl group, the quinoline-5-yl group, the quinoline-6-yl group, the quinoline-7-yl group, the quinoline-8-yl group, the benzothiazole-2-yl group, the 2-mercaptobenzothiazole-6-yl group. The naphthyl group having a radically polymerizable group-containing group or a cationically polymerizable group-containing group is also preferred as the optionally substituted monocyclic aromatic group.

Among these groups, the naphthalene-1-yl group, the quinoline-3-yl group, the quinoline-4-yl group, and 2-mercaptobenzothiazole-6-yl group are preferred, and the naphthalene-1-yl group is more preferred.

As mentioned above, the monocyclic aromatic group or the condensed aromatic group as $R^{A1}$, $R^{A2}$, and $R^{A3}$ may have a radically polymerizable group-containing group or a cationically polymerizable group-containing group as a polymerizable group. However, the compound represented by the formula (A1) does not have a radically polymerizable group-containing group and a cationically polymerizable group-containing group in combination. The position to which the radically polymerizable group-containing group or the cationically polymerizable group-containing group in the monocyclic aromatic group or the condensed aromatic group as $R^{A1}$, $R^{A2}$, and $R^{A3}$ is not particularly limited.

The number of the radically polymerizable group-containing group(s) or the cationically polymerizable group-containing group(s) in the monocyclic aromatic group or the condensed aromatic group as $R^{A1}$, $R^{A2}$, and $R^{A3}$ is not particularly limited. The number of the radically polymerizable group-containing group(s) or the cationically polymerizable group-containing group(s) in the monocyclic aromatic group or the condensed aromatic group as $R^{A1}$, $R^{A2}$, and $R^{A3}$ is preferably an integer of 1 or more and 3 or less, more preferably 1 or 2, and particularly preferably 1.

Examples of the radically polymerizable group-containing group typically include a group containing an ethylenically unsaturated double bond. The ethylenically unsaturated double bond-containing group is preferably an alkenyl group-containing group containing an alkenyl group such as a vinyl group and an allyl group, and more preferably a (meth)acryloyl group-containing group. Examples of the cationically polymerizable group typically include an epoxy group-containing group, an oxetanyl group-containing group, and a vinyloxy group-containing group. Among these, an epoxy group-containing group and a vinyloxy group-containing group are preferred. Preferred epoxy group-containing groups are an alicyclic epoxy group-containing group and a glycidyl group. It should be noted that the alicyclic epoxy group is an aliphatic cyclic group in which adjacent two carbon atoms, as atoms constituting the ring, are bonded via an oxygen atom. That is, the alicyclic epoxy group has an epoxy group including a 3-membered ring composed of two carbon atoms and one oxygen atom on the aliphatic ring.

In the description and claims of the present application, (meth)acryl means both acryl and methacryl, (meth)acryloyl means both acryloyl and methacryloyl, and (meth)acrylate means both acrylate and methacrylate.

Suitable examples of the radically polymerizable group-containing group include groups represented by the following formula (A-I) or the following formula (A-II), that do not correspond to a vinyloxy group.

$$-(A^{01})_{na}\text{-}R^{01} \quad (A\text{-}I)$$

$$-(A^{01})_{na}\text{-}R^{02}\text{-}A^{02}\text{-}R^{01} \quad (A\text{-}II)$$

In the formula (A-I) and the formula (A-II), $R^{01}$ is an alkenyl group having 2 or more and 10 or less carbon atoms. $Ra^{02}$ is an alkylene group having 1 or more and 10 or less carbon atoms. $A^{01}$ is —O—, —S—, —CO—, —CO—O—, —CO—S—, —O—CO—, —S—CO—, —CO—NH—, —NH—CO—, or —NH—. $A^{02}$ is —O—, —S—, —CO—, —CO—O—, —CO—S—, —O—CO—, —S—CO—, —CO—NH—, —NH—CO—, or —NH—. na is 0 or 1.

Suitable examples of radically polymerizable group-containing group include groups represented by
—O—$R^{03}$,
—S—$R^{03}$,
—O—$CH_2CH_2$—O—$R^{03}$,
—O—$CH_2CH_2CH_2$—O—$R^{03}$,
—O—$CH_2CH_2CH_2CH_2$—O—$R^{03}$,
—COO—$CH_2CH_2$—O—$R^{03}$,
—CO—O—$CH_2CH_2CH_2$—O—$R^{03}$,
—CO—O—$CH_2CH_2CH_2CH_2$—O—$R^{03}$,
—O—$CH_2CH_2$—NH—$R^{03}$,
—O—$CH_2CH_2CH_2$—NH—$R^{03}$,
—O—$CH_2CH_2CH_2CH_2$—NH—$R^{03}$,
—CO—O—$CH_2CH_2$—NH—$R^{03}$,
—CO—O—$CH_2CH_2CH_2$—NH—$R^{03}$,
—CO—O—$CH_2CH_2CH_2CH_2$—$R^{03}$,
—NH—$R^{03}$,
—NH—$CH_2CH_2$—O—$R^3$,
—NH—$CH_2CH_2CH_2$—O—$R^3$,
—NH—$CH_2CH_2CH_2$—$R^{03}$,
—CO—NH—$CH_2CH_2$—O—$R^{03}$,
—CO—NH—$CH_2CH_2CH_2$—O—$R^{03}$,
—CO—NH—$CH_2CH_2CH_2CH_2$—O—$R^{03}$,
—NH—$CH_2CH_2$—NH—$R^{03}$,
—NH—$CH_2CH_2CH_2$—NH—$R^{03}$,
—NH—$CH_2CH_2CH_2CH_2$—NH—$R^{03}$,
—CO—NH—$CH_2CH_2$—NH—$R^{03}$,
—CO—NH—$CH_2CH_2CH_2$—NH—$R^{03}$, and
—CO—NH—$CH_2CH_2CH_2CH_2$—NH—$R^{03}$. $R^{03}$ in these groups is an allyl group or a (meth)acryloyl group.

Suitable examples of the cationically polymerizable group-containing group include groups represented by the following formulas (A3) to (A8).

$$-(A^{01})_{na}\text{-}R^{04} \quad (A3)$$

$$-(A^{01})_{na}\text{-}R^{02}\text{—}R^{05} \quad (A4)$$

$$-(A^{01})_{na}\text{-}R^{02}\text{—}(CO)_{nb}\text{-}A^{03}\text{-}R^{04} \quad (A5)$$

$$-(A^{01})_{na}\text{-}R^{02}\text{—}(CO)_{nb}\text{-}A^{03}\text{-}R^{07}\text{—}R^{05} \quad (A6)$$

$$-(A^{01})_{na}\text{-}R^{02}\text{—}O\text{—}R^{06} \quad (A7)$$

$$-(A^{01})_{na}\text{-}R^{02}\text{—}(CO)_{nb}\text{-}A^{03}\text{-}R^{07}\text{—}O\text{—}R^{06} \quad (A8)$$

In the formula (A3) to formula (A8), $R^{a02}$ is an alkylene group having 1 or more and 10 or less carbon atoms. $R^{04}$ is an epoxyalkyl group having 2 or more and 20 or less carbon atoms or an alicyclic epoxy group having 3 or more and 20 or less carbon atoms. $R^{05}$ is an alicyclic epoxy group having 3 or more and 20 or less carbon atoms. $R^{06}$ is a vinyl group. $R^{07}$ is an alkylene group having 1 or more and 10 or less carbon atoms. $A^{01}$ is —O—, —S—, —CO—, —CO—O—, —CO—S—, —O—CO—, —S—CO—, —CO—NH—, —NH—CO—, or —NH—. $A^{03}$ is —O— or —NH—. Nb is 0 or 1.

Suitable examples of cationically polymerizable group-containing group include groups represented by
—$R^{08}$,
—O—$CH_2CH_2$—$R^{08}$,
—O—$CH_2CH_2CH_2$—$R^{08}$,
—O—$CH_2CH_2CH_2CH_2$—$R^{08}$,
—CO—O—$CH_2CH_2$—$R^{08}$,
—COO—$CH_2CH_2CH_2$—$R^{08}$,
—COO—$CH_2CH_2CH_2CH_2$—$R^{08}$,
—NH—$CH_2CH_2$—$R^{08}$,
—NH—$CH_2CH_2CH_2$—$R^{08}$,
—NH—$CH_2CH_2CH_2CH_2$—$R^{08}$,

—CO—NH—CH$_2$CH$_2$—R$^{O8}$,

—CO—NH—CH$_2$CH$_2$CH$_2$—R$^{O8}$, and

—CO—NH—CH$_2$CH$_2$CH$_2$CH$_2$—R$^{O8}$. R$^{O8}$ in these groups is a vinyloxy group, a glycidyloxy group, a glycidylthio group, an epoxycyclopentyl group, an epoxycyclohexyl group, or an epoxycycloheptyl group.

When the monocyclic aromatic group or the condensed aromatic group as R$^{A1}$, R$^{A2}$, and R$^{A3}$ has one radically polymerizable group-containing group or one cationically polymerizable group-containing group, preferred examples of R$^{A1}$, R$^{A2}$, and R$^{A3}$ include the groups of the following formula. In the following formula, PG is a radically polymerizable group-containing group or a cationically polymerizable group-containing group.

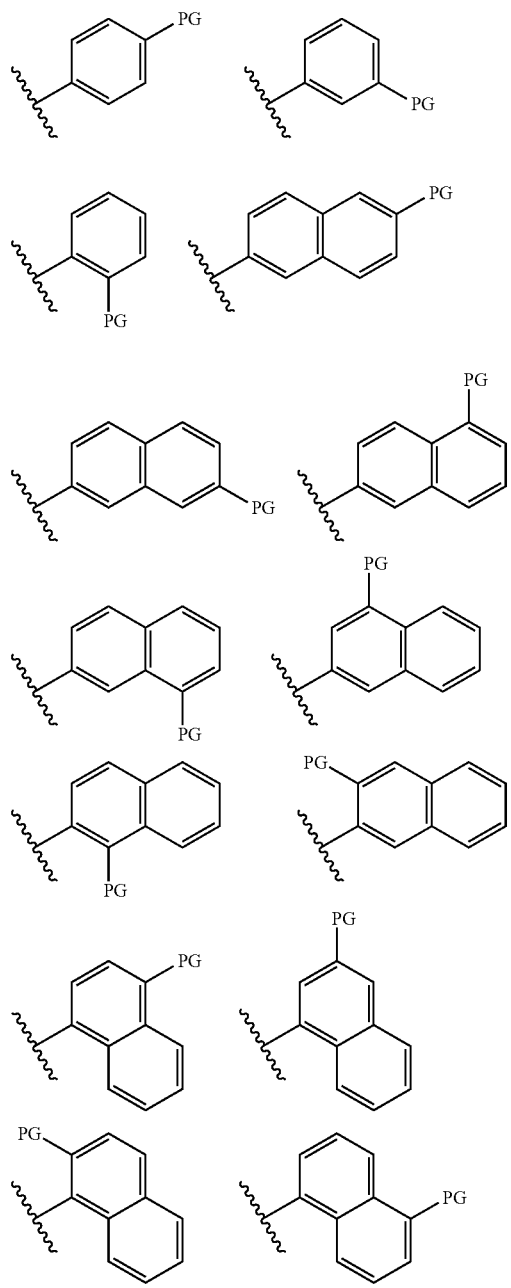

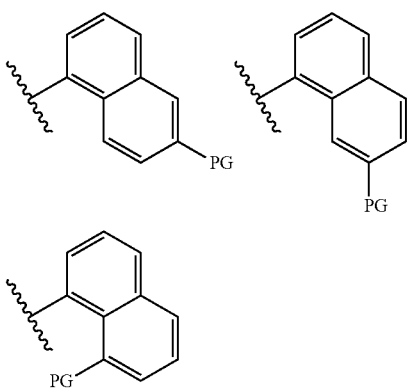

Among the compounds represented by the formula (A1) described above, a compound in which one or two of R$^{A1}$, R$^{A2}$, and R$^{A3}$ is/are an optionally substituted naphthyl group(s) and one or two of R$^{A1}$, R$^{A2}$, and R$^{A3}$ is/are a 4-cyanophenyl group(s) or a benzothiazolyl group(s) is preferred because the refractive index of the cured product, the surface appearance of the cured product, and the heat resistance of the cured product are well-balanced and excellent.

As the optionally substituted naphthyl group, a naphthalen-1-yl group is preferred.

Specific examples of the compound represented by the formula (A1) include compounds represented by the following formulas. In the formulas below, X$^A$ is a group selected from the group consisting of a (meth)acryloyloxy group, a 3-(meth)acryloyloxy-2-hydroxy-n-propyloxycarbonyl group, and a glycidyloxy group.

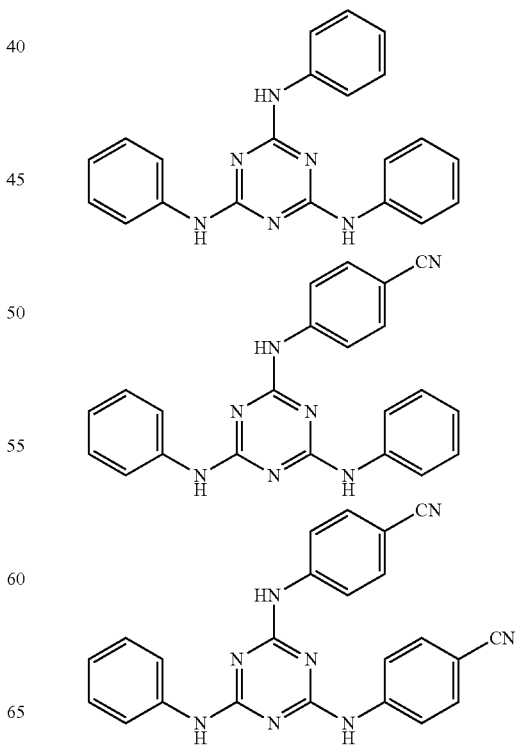

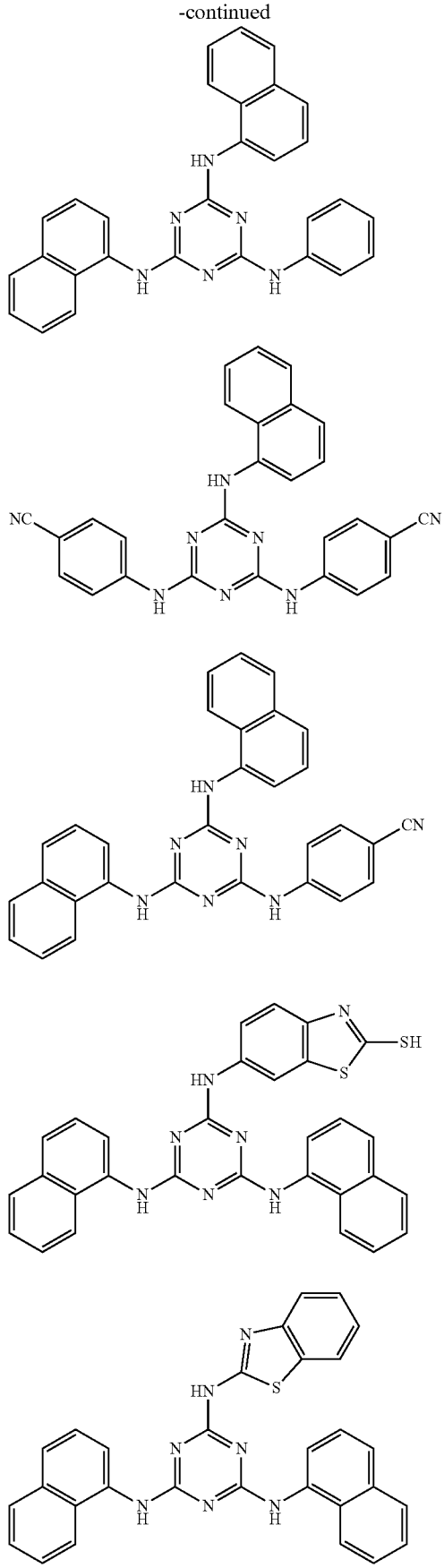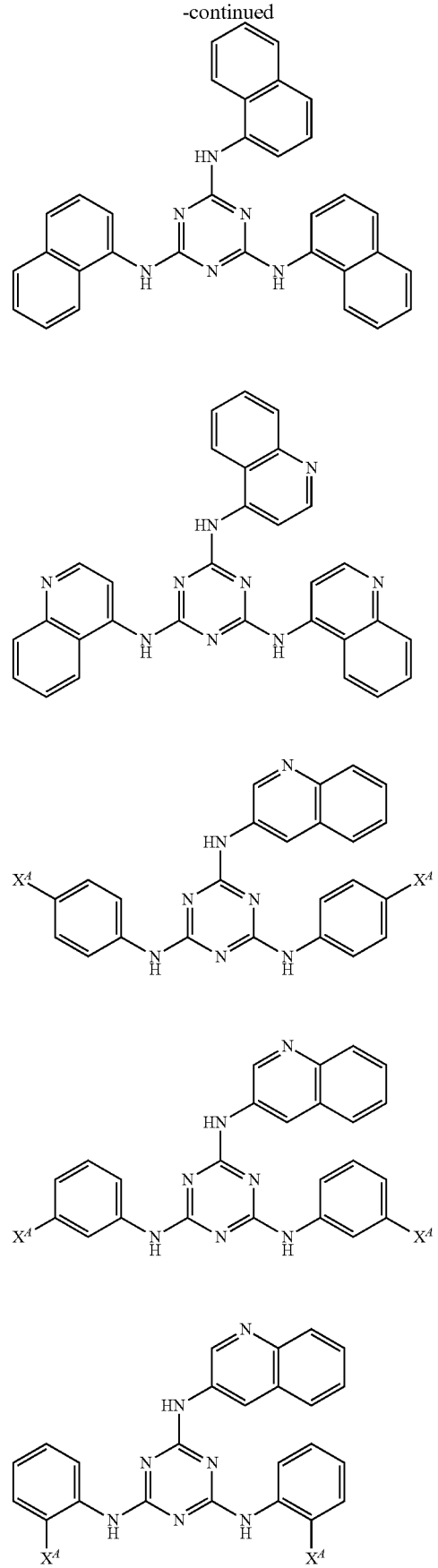

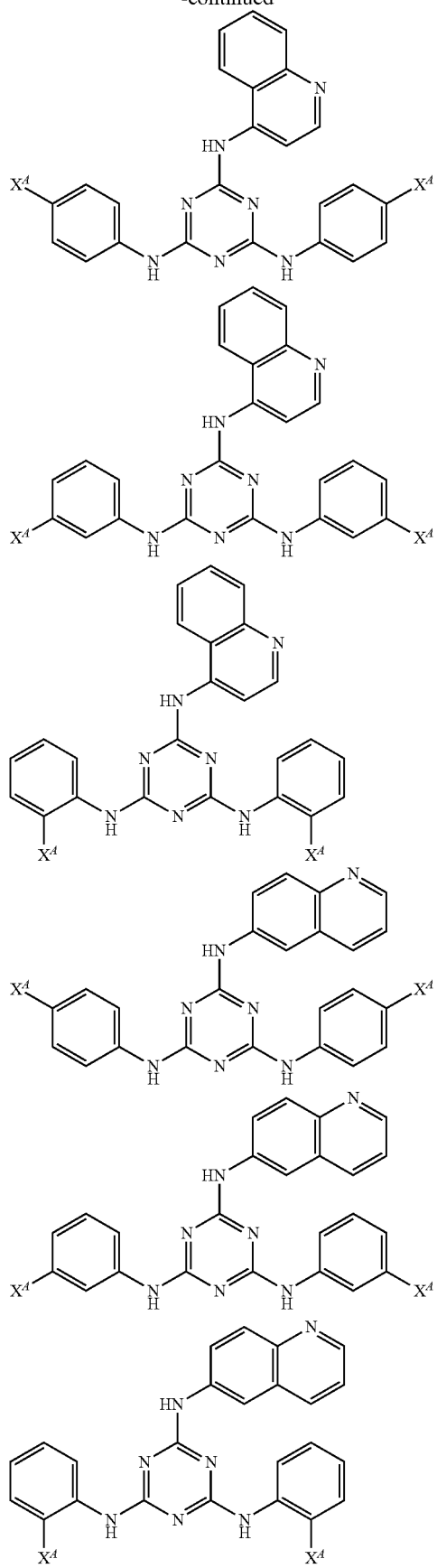
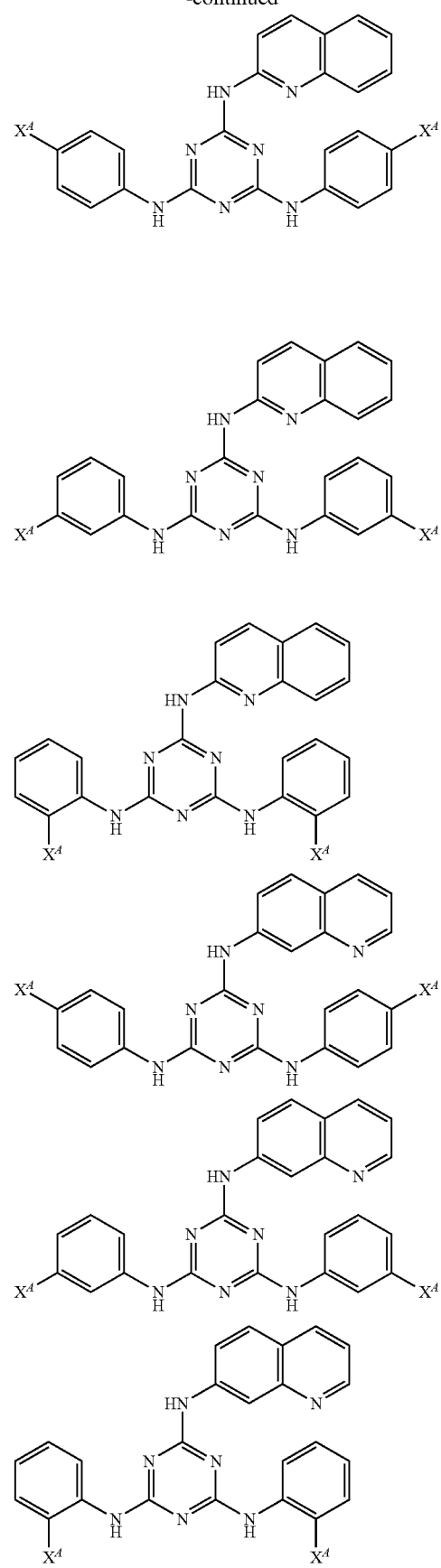

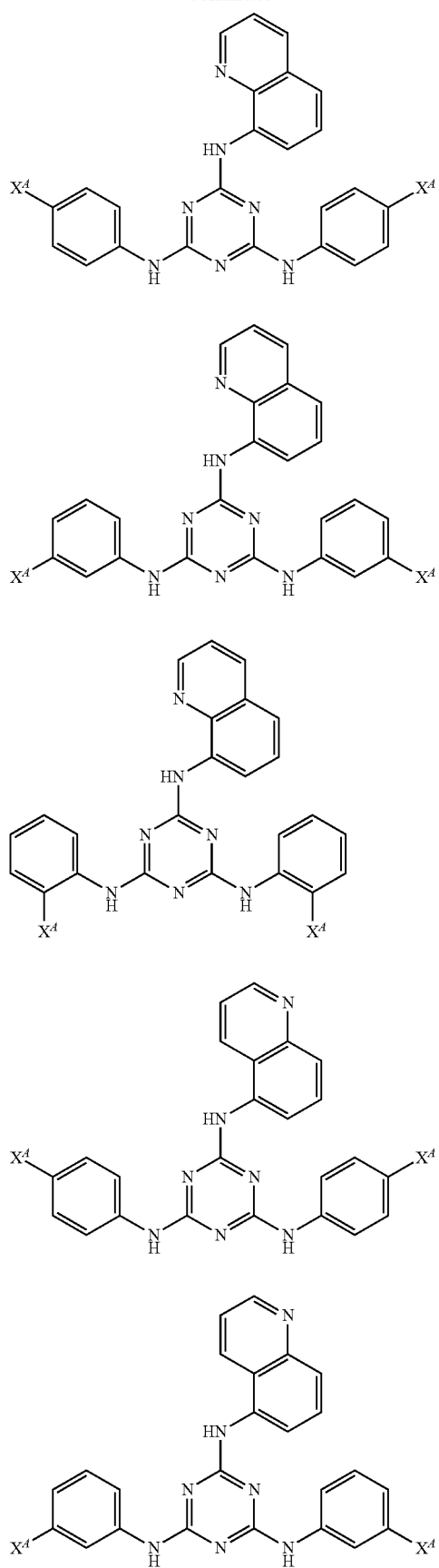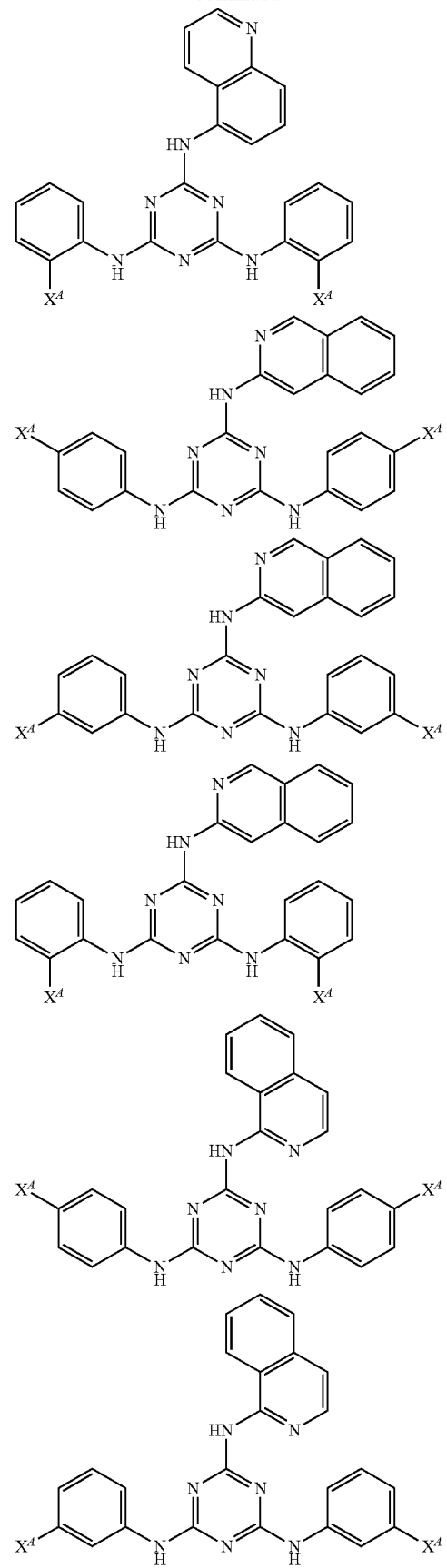

-continued
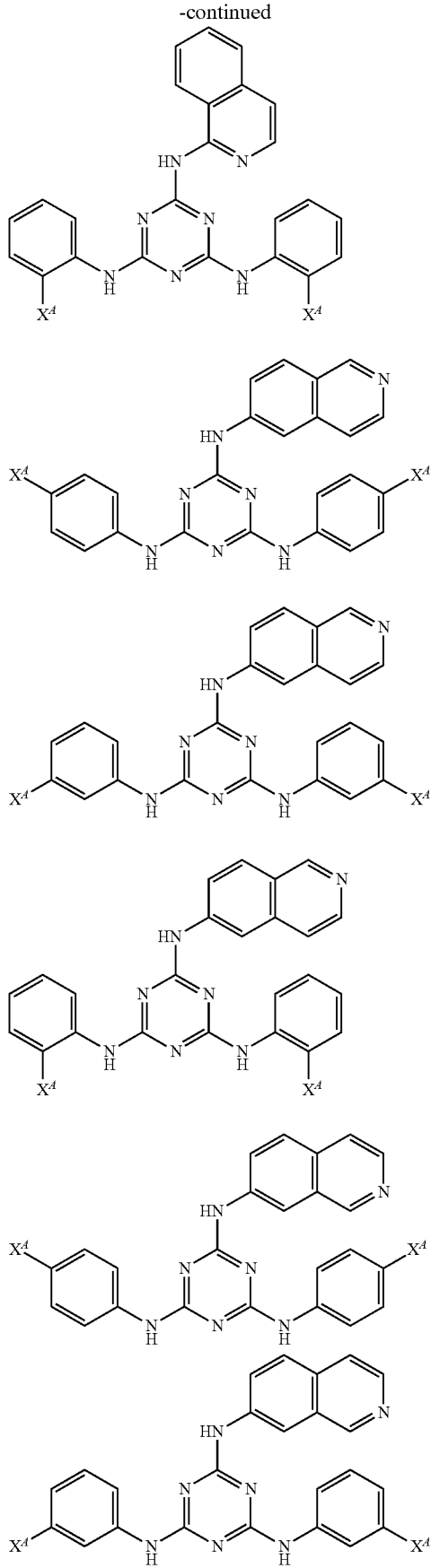
-continued
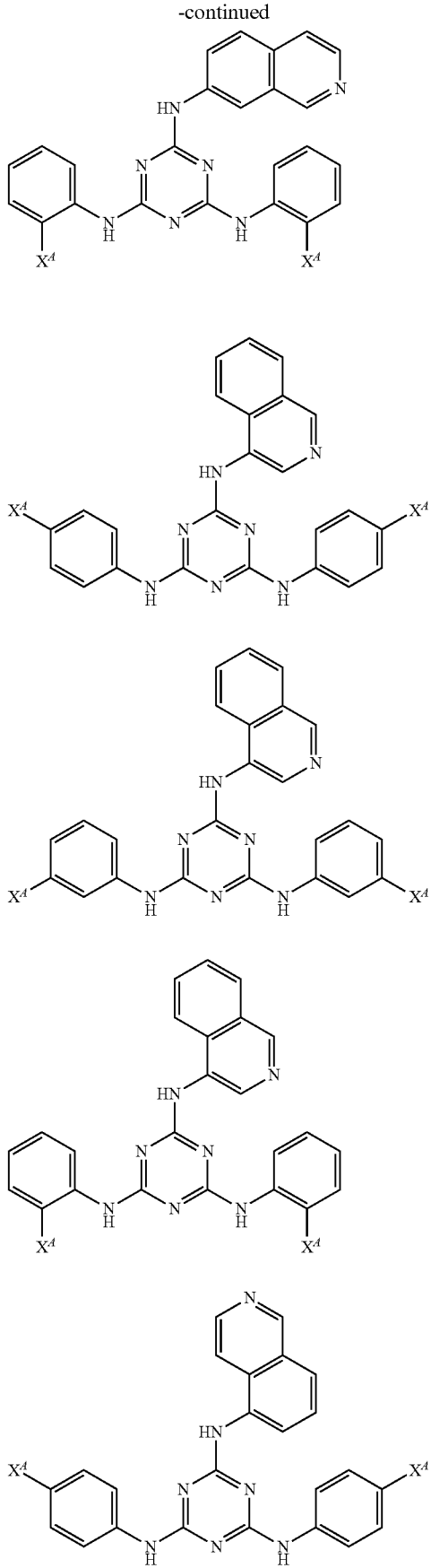

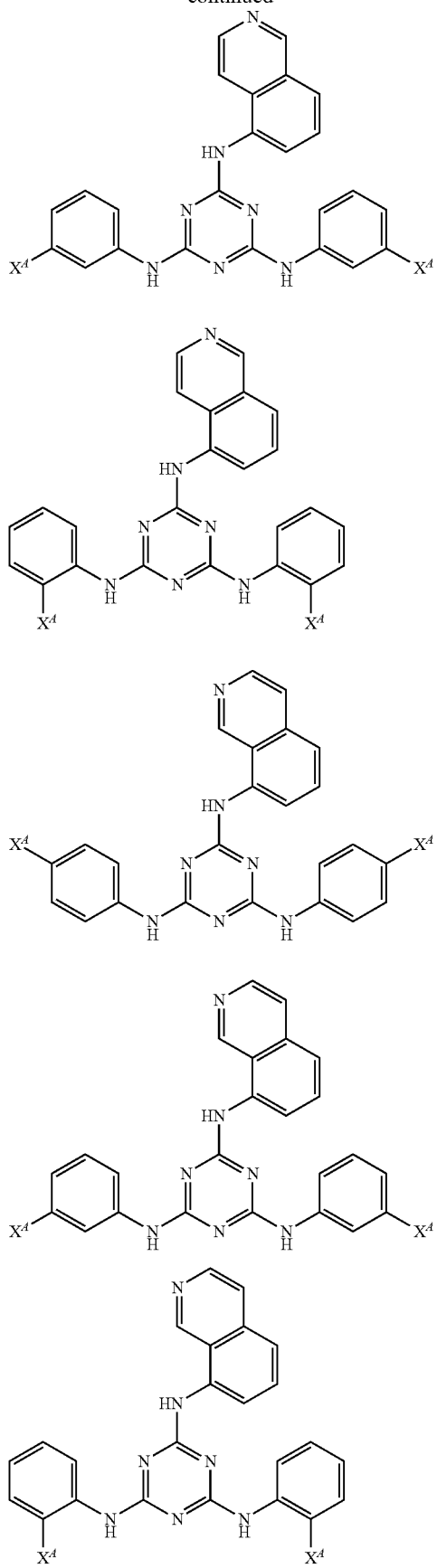
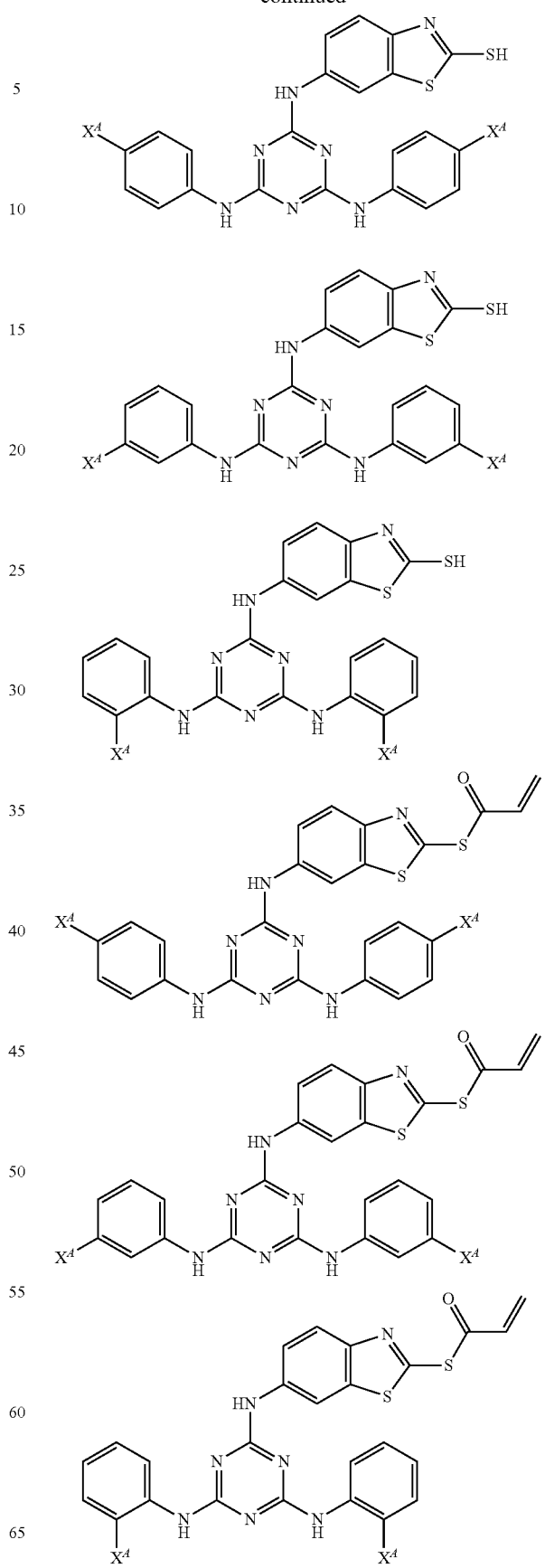

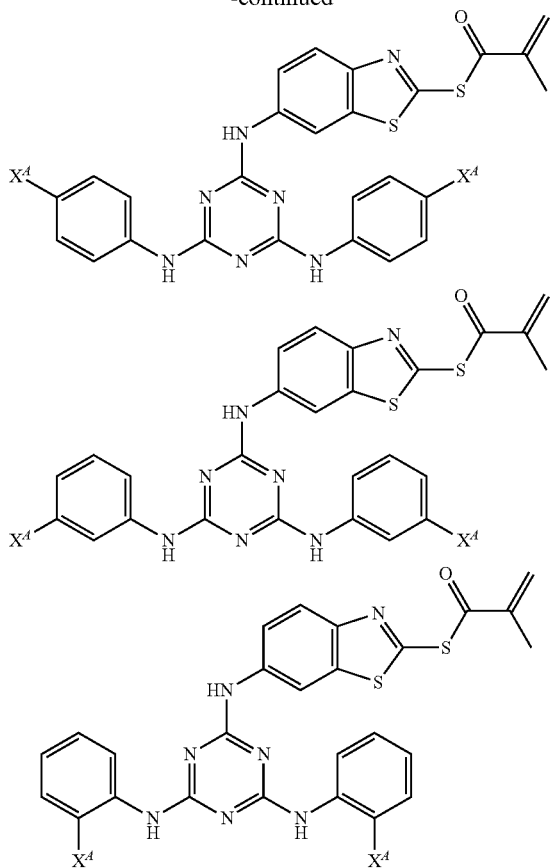

The method of producing the compound represented by the formula (A1) is not particularly limited.

The compound can be typically produced by reacting cyanuric halide such as cyanuric chloride with aromatic amines represented by $R^{A1}$—$NH_2$, $R^{A2}$—$NH_2$, and $R^{A3}$—$NH_2$.

These plural types of amines may be reacted simultaneously with cyanuric halide, may be reacted sequentially with cyanuric halide, and is preferably reacted with sequentially with cyanuric halide.

Alternatively, $R^{A2}$ and $R^{A3}$ in the formula (A1) can be produced by reacting aromatic amines having a functional group such as a hydroxyl group, a mercapto group, a carboxy group, or an amino group with cyanuric halide and then reacting a compound that gives a radically polymerizable group-containing group or a cationically polymerizable group-containing group with these functional groups. Examples of the compound that gives a radically polymerizable group-containing group or a cationically polymerizable group-containing group include compounds having a polymerizable group such as (meth)acryl acid, (meth)acrylic halide, halogenated olefins, epichlorohydrin, and glycidyl (meth)acrylate. As the reaction between the functional group such as a hydroxyl group, a mercapto group, a carboxy group, or an amino group and the compound having a polymerizable group, well-known reactions that produce an ether bond, a carboxylic ester bond, a carboxylic amide bond, and a thioether bond can be used.

The reaction that forms a radically polymerizable group-containing group or a cationically polymerizable group-containing group may be a multi-stage reaction. For example, an aromatic amine having a phenolic hydroxyl group is reacted with cyanuric halide, and then the phenolic hydroxyl group is glycidylated by a reaction with epichlorohydrin.

Subsequently, acrylic acid is reacted with the glycidyl group to thereby enable a radically polymerizable group-containing group represented by the following formula to be introduced on the aromatic ring.

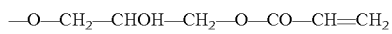

The above reaction is an example, and the radically polymerizable group-containing group or the cationically polymerizable group-containing group can be formed by carrying out various reactions in combination.

The compound represented by the formula (A1) is usually synthesized in an organic solvent. Such organic solvent is not particularly limited as long as the organic solvent is an inert solvent that does not react with cyanuric halide, an aromatic amine, a radically polymerizable group, a cationically polymerizable group, and the like. As the solvent, organic solvents and the like exemplified as specific examples of the solvent (S) can be used. In production of the compound represented by the formula (A1), the temperature at which cyanuric halide is reacted with aromatic amines such as aromatic amines represented by $R^{A1}$—$NH_2$, $R^{A2}$—$NH_2$, and $R^{A3}$—$NH_2$ is not particularly limited. The reaction temperature is typically preferably 0° C. or more and 150° C. or less.

The content of the heterocyclic compound (A) in the curable composition is not particularly limited as long as the desired effects are not impaired. The content of the heterocyclic compound (A) in the curable composition relative to 100 parts by mass of the mass of the curable composition excluding the mass of the solvent (S) described later is preferably 30 parts by mass or more and 99.99 parts by mass or less, more preferably 60 parts by mass or more and 95 parts by mass or less, and even more preferably 70 parts by mass or more and 90 parts by mass or less.

<Polymerizable Compound (B)>

The curable composition may include, in addition to the heterocyclic compound (A), a polymerizable compound (B) that may be polymerized singly or may be polymerized with a heterocyclic compound having a polymerizable group. When the heterocyclic compound (A) has a polymerizable group, the curable composition includes or does not include a polymerizable compound (B) other than the heterocyclic compound (A). When the heterocyclic compound (A) has no polymerizable group, the curable composition includes a polymerizable compound (B) other than the heterocyclic compound (A).

when the heterocyclic compound (A) has no polymerizable group, or has a radically polymerizable group, the curable composition may include a compound having a radically polymerizable group as the polymerizable compound (B). Such polymerizable compound (B) may be a monofunctional compound having one radically polymerizable group, may be a polyfunctional compound having two or more radically polymerizable groups, and is preferably a polyfunctional compound. The radically polymerizable group is as mentioned above for the heterocyclic compound (A). The polymerizable compound (B) having a radically polymerizable group is preferably a compound having one or more (meth)acryloyl group such as a (meth)acrylate compound or a (meth)acrylamide compound and more preferably a (meth)acrylate compound having one or more (meth)acryloyl group.

Examples of the monofunctional compound having the radically polymerizable group include (meth)acrylamide, methylol (meth)acrylamide, methoxymethyl(meth)acrylamide, ethoxymethyl(meth)acrylamide, propoxymethyl(meth)acrylamide, butoxymethoxymethyl(meth)acrylamide, N-methylol (meth)acrylamide, N-hydroxymethyl(meth)acrylamide, (meth)acrylic acid, fumaric acid, maleic acid, maleic anhydride, itaconic acid, itaconic anhydride, citraconic acid, citraconic anhydride, crotonic acid, 2-acrylamide-2-methylpropanesulfonic acid, tert-butylacrylamide sulfonic acid, methyl (meth)acrylate, ethyl (meth)acrylate, butyl (meth)acrylate, 2-ethylhexyl (meth)acrylate, cyclohexyl (meth)acrylate, 2-hydroxyethyl (meth)acrylate, 2-hydroxypropyl (meth)acrylate, 2-hydroxybutyl (meth)acrylate, 2-phenoxy-2-hydroxypropyl (meth)acrylate, 2-(meth)acryloyloxy-2-hydroxypropyl phthalate, glycerol mono(meth)acrylate, tetrahydrofurfuryl (meth)acrylate, N,N-dimethyl-2-aminoethyl (meth)acrylate, glycidyl (meth)acrylate, 2,2,2-trifluoroethyl (meth)acrylate, 2,2,3,3-tetrafluoropropyl (meth)acrylate, half (meth)acrylates of phthalic acid derivatives, and the like. These monofunctional compounds may be used alone, or in combination of two or more types thereof.

Examples of the polyfunctional compound having the radically polymerizable group include polyfunctional compounds such as ethylene glycol di(meth)acrylate, diethylene glycol di(meth)acrylate, tetraethylene glycol di(meth)acrylate, propylene glycol di(meth)acrylate, polypropylene glycol di(meth)acrylate, butylene glycol di(meth)acrylate, neopentyl glycol di(meth)acrylate, 1,6-hexane glycol di(meth)acrylate, dimethyroltricyclodecane di(meth)acrylate, trimethylolpropane tri(meth)acrylate, glycerol di(meth)acrylate, pentaerythritol di(meth)acrylate, pentaerythritol tri(meth)acrylate, pentaerythritol tetra(meth)acrylate, dipentaerythritol penta(meth)acrylate, dipentaerythritol hexa(meth)acrylate, 2,2-bis(4-(meth)acryloxydiethoxyphenyl)propane, 2,2-bis(4-(meth)acryloxypolyethoxyphenyl)propane, 2-hydroxy-3-(meth)acryloyloxypropyl (meth)acrylate, ethylene glycol diglycidyl ether di(meth)acrylate, diethylene glycol diglycidyl ether di(meth)acrylate, phthalic acid diglycidyl ester di (meth)acrylate, glycerol triacrylate, glycerol polyglycidyl ether poly(meth)acrylate, urethane (meth)acrylate (in other words, tolylene diisocyanate), a reaction product of trimethylhexamethylene diisocyanate, hexamethylene diisocyanate, or the like with 2-hydroxyethyl (meth)acrylate), methylenebis(meth)acrylamide, (meth)acrylamide methylene ether, polyfunctional compound such as condensates of a polyhydric alcohol and N-methylol (meth)acrylamide, triacrylformal, and the like. These polyfunctional compounds may be used alone, or in combination of two or more types thereof.

Of these polymerizable compounds (B) having a radically polymerizable group, trifunctional or higher polyfunctional compound is preferable, a tetrafunctional or higher polyfunctional compound is more preferable, and a pentafunctional or higher polyfunctional compound is still more preferable, in view of the fact that they tend to increase the strength of the cured product.

When the heterocyclic compound (A) has no polymerizable group or a vinyloxy group as the cationically polymerizable group-containing group, the curable composition may include a vinyl ether compound. Such vinyl ether compound may be a monofunctional compound or may be a polyfunctional compound.

Suitable specific examples of the vinyl ether compound include aromatic monovinyl ether compounds such as vinyl phenyl ether, 4-vinyloxytoluene, 3-vinyloxytoluene, 2-vinyloxytoluene, 1-vinyloxy-4-chlorobenzene, 1-vinyloxy-3-chlorobenzene, 1-vinyloxy-2-chlorobenzene, 1-vinyloxy-2,3-dimethylbenzene, 1-vinyloxy-2,4-dimethylbenzene, 1-vinyloxy-2,5-dimethylbenzene, 1-vinyloxy-2,6-dimethylbenzene, 1-vinyloxy-3,4-dimethylbenzene, 1-vinyloxy-3,5-dimethylbenzene, 1-vinyloxynaphthalene, 2-vinyloxynaphthalene, 2-vinyloxyfluorene, 3-vinyloxyfluorene, 4-vinyloxy-1,1'-biphenyl, 3-vinyloxy-1,1'-biphenyl, 2-vinyloxy-1,1'-biphenyl, 6-vinyloxytetralin, and 5-vinyloxytetralin; and aromatic divinyl ether compounds such as 1,4-divinyloxybenzene, 1,3-divinyloxybenzene, 1,2-divinyloxybenzene, 1,4-divinyloxynaphthalene, 1,3-divinyloxynaphthalene, 1,2-divinyloxynaphthalene, 1,5-divinyloxynaphthalene, 1,6-divinyloxynaphthalene, 1,7-divinyloxynaphthalene, 1,8-divinyloxynaphthalene, 2,3-divinyloxynaphthalene, 2,6-divinyloxynaphthalene, 2,7-divinyloxynaphthalene, 1,2-divinyloxyfluorene, 3,4-divinyloxyfluorene, 2,7-divinyloxyfluorene, 4,4'-divinyloxybiphenyl, 3,3'-divinyloxybiphenyl, 2,2'-divinyloxybiphenyl, 3,4'-divinyloxybiphenyl, 2,3'-divinyloxybiphenyl, 2,4'-divinyloxybiphenyl, and bisphenol A divinyl ether, and the like. These vinyl ether compounds may be used in combination of two or more types thereof.

When the heterocyclic compound (A) has no polymerizable group or a epoxy group-containing group as the cationically polymerizable group, the curable composition may include various epoxy compounds as the polymerizable compound (B). Examples of epoxy compounds include bifunctional epoxy resins such as a bisphenol A type epoxy resin, a bisphenol F type epoxy resin, a bisphenol S type epoxy resin, a bisphenol AD type epoxy resin, a naphthalene type epoxy resin and a biphenyl type epoxy resin; novolak epoxy resins such as a phenol novolak type epoxy resin, a brominated phenol novolak type epoxy resin, an ortho-cresol novolak type epoxy resin, a bisphenol A novolak type epoxy resin, and a bisphenol AD novolak type epoxy resin; alicyclic epoxy resins such as an epoxylated product of dicyclopentadiene type phenol resin; aromatic epoxy resins such as an epoxylated product of naphthalene type phenol resin; glycidyl ester type epoxy resins such as a dimer acid glycidyl ester, and triglycidyl ester; glycidylamine type epoxy resins such as a tetraglycidylaminodiphenylmethane, a triglycidyl-p-aminophenol, a tetraglycidyl methaxylylenediamine and a tetraglycidyl bisaminomethylcyclohexane; heterocyclic epoxy resins such as a triglycidyl isocyanurate; trifunctional epoxy resins such as a phloroglycinol triglycidyl ether, a trihydroxybiphenyl triglycidyl ether, a trihydroxyphenylmethane triglycidyl ether, a glycerol triglycidyl ether, a 2-[4-(2,3-epoxypropoxy)phenyl]-2-[4-[1,1-bis[4-(2,3-epoxypropoxy)phenyl]ethyl]phenyl]propane and a 1,3-bis[4-[1-[4-(2,3-epoxypropoxy)phenyl]-1-[4-[1-[4-(2,3-epoxypropoxy)phenyl]-1-methylethyl]phenyl]ethyl]phenoxy]-2-propanol; tetrafunctional epoxy resins such as a tetrahydroxyphenylethane tetraglycidyl ether, a tetraglycidylbenzophenone, a bisresorcinol tetraglycidyl ether and a tetraglycidoxybiphenyl; and a 1,2-epoxy-4-(2-oxiranyl)cyclohexane adduct of 2,2-bis(hydroxymethyl)-1-butanol. The 1,2-epoxy-4-(2-oxiranyl)cyclohexane adduct of 2,2-bis(hydroxymethyl)-1-butanol is commercially available as EHPE-3150 (manufactured by Daicel Corporation).

In addition, an oligomer or polymer type polyfunctional epoxy compound can be preferably used. Typical examples of the oligomer or polymer type polyfunctional epoxy compound include a phenol novolak type epoxy compound, a brominated phenol novolak type epoxy compound, an ortho-cresol type novolak epoxy compound, a xylenol novolak type epoxy compound, a naphthol novolak type epoxy compound, a bisphenol A novolak type epoxy compound, a bisphenol AD novolak type epoxy compound, an epoxylated product of dicyclopentadiene phenol resin, an epoxylated product of naphthalene phenol resin, and the like.

Other examples of suitable epoxy compounds include a polyfunctional alicyclic epoxy compound having an alicyclic epoxy group.

Specific examples of the alicyclic epoxy compound include 2-(3,4-epoxycyclohexyl-5,5-spiro-3,4-epoxy)cyclohexane-meta-dioxane, bis(3,4-epoxycyclohexylmethyl)adipate, bis(3,4-epoxy-6-methylcyclohexylmethyl)adipate, 3,4-epoxy-6-methylcyclohexyl-3',4'-epoxy-6'-methylcyclohexanecarboxylate, ε-caprolactone-modified 3,4-epoxycyclohexylmethyl-3',4'-epoxycyclohexanecarboxylate, trimethylcaprolactone-modified 3,4-epoxycyclohexylmethyl-3',4'-epoxycyclohexanecarboxylate, β-methyl-δ-valerolactone-modified 3,4-epoxycyclohexylmethyl-3',4'-epoxycyclohexanecarboxylate, methylenebis(3,4-epoxycyclohexane), di(3,4-epoxycyclohexylmethyl) ether of ethylene glycol, ethylenebis(3,4-epoxycyclohexanecarboxylate), epoxycyclohexahydrophthalic acid dioctyl ester, epoxyxyclohexahydrophthalic acid di-2-ethylhexyl ester, epoxy resins having a tricyclodecene oxide group, and compounds represented by the following formulas (b01-1) to (b01-5).

Among specific examples of the alicyclic epoxy compound, alicyclic epoxy compounds represented by the following formulas (b01-1) to (b01-5) are preferred since they give cured materials with high hardness.

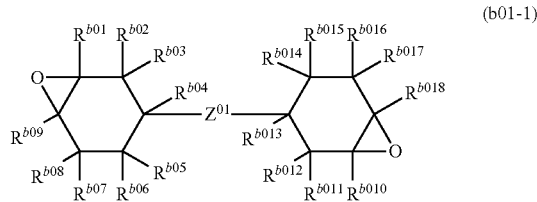
(b01-1)

In the formula (b01-1), $Z^{01}$ is a single bond, or a bridging group (divalent group having one or more atoms). $R^{b01}$ to $R^{b018}$ are each independently a group selected from the group consisting of a hydrogen atom, a halogen atom and an organic group.

Example of bridging group $Z^{01}$ includes a divalent group selected form the group consisting of a divalent hydrocarbon group, —O—, —O—CO—, —S—, —SO—, —SO$_2$—, —CBr$_2$—, —C(CBr$_3$)$_2$—, —C(CF$_3$)$_2$—, and —R$^{b019}$—O—CO— or a group formed by bonding plural of these divalent groups.

When the bridging group $Z^{01}$ is a divalent hydrocarbon group, example of the hydrocarbon group includes a linear or branched alkylene group having 1 or more and 18 or less carbon atoms, a divalent alicyclic hydrocarbon group and the like. The linear or branched alkylene group having 1 or more and 18 or less carbon atoms includes, for example, a methylene group, a methylmethylene group, a dimethylmethylene group, a dimethylene group, a trimethylene group, and the like. The divalent alicyclic hydrocarbon group described above includes, for example, a cycloalkylene group (including a cydlohexylidene group) such as a 1,2-cyclopentylene group, a 1,3-cyclopentylene group, a cyclopentylidene group, a 1,2-cyclohexylene group, 1,3-cyclohexylene group, 1,4-cyclohexylene group, and a cyclohexylidene group.

$R^{b019}$ is an alkylene group having 1 or more and 8 or less carbon atoms and preferably a methylene group or an ethylene group.

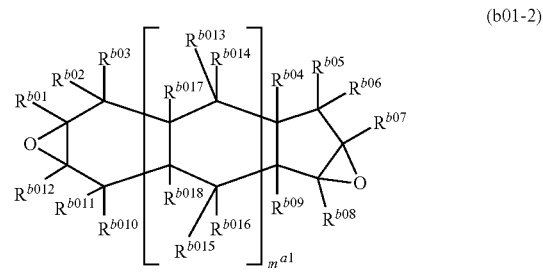
(b01-2)

In the formula (b01-2), $R^{b01}$ to $R^{b012}$ each independently represents a group selected from the group consisting of a hydrogen atom, a halogen atom, and an organic group. $R^{b02}$ and $R^{b010}$ may be combined to each other. $R^{b013}$ and $R^{b016}$ may be combined to each other to form a ring. $m^{a1}$ is 0 or 1.

A compound represented by the following formula (b01-2-1) which corresponds to the compound in which $m^{a1}$ is 0 in the formula (b01-2) is preferred as the alicyclic epoxy compound represented by the formula (b01-2).

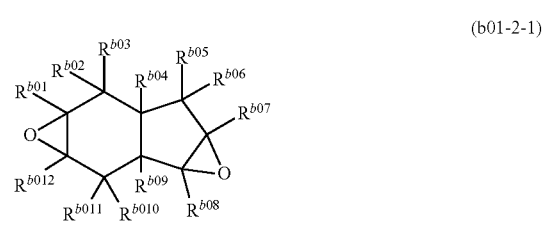
(b01-2-1)

In the formula (b01-2-1), $R^{b01}$ to $R^{b012}$ each independently represents a group selected from the group consisting of a hydrogen atom, a halogen atom, and an organic group. $R^{b012}$ and $R^{b010}$ may be combined to each other to form a ring.

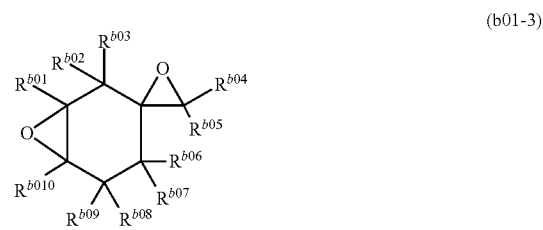
(b01-3)

In the formula (b01-3), $R^{b01}$ to $R^{b010}$ each independently represents a group selected from the group consisting of a hydrogen atom, a halogen atom, and an organic group.

$R^{b02}$ and $R^{b08}$ may be combined to each other.

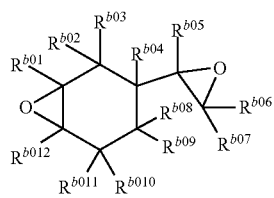

(b01-4)

In the formula (b01-4), $R^{b01}$ to $R^{b012}$ each independently represents a group selected from the group consisting of a hydrogen atom, a halogen atom, and an organic group.

$R^{b02}$ and $R^{b08}$ may be combined to each other.

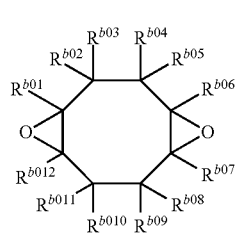

(b01-5)

In the formula (b01-5), $R^{b01}$ to $R^{b012}$ each independently represents a group selected from the group consisting of a hydrogen atom, a halogen atom, and an organic group.

In the formulae (b01-1) to (b01-5), when $R^{b01}$ to $R^{b018}$ are organic groups, the organic group is not particularly limited as long as the object of the present invention is not impaired, and may be a hydrocarbon group, or a group consisting of a carbon atom and a halogen atom, or a group having heteroatoms such as a halogen atom, an oxygen atom, a sulfur atom, a nitrogen atom, and a silicon atom, together with a carbon atom and a hydrogen atom. Examples of the halogen atom include a chlorine atom, a bromine atom, an iodine atom, and a fluorine atom.

The organic group is preferably a group consisting of a hydrocarbon group, a group consisting of a carbon atom, a hydrogen atom, and an oxygen atom; a halogenated hydrocarbon group, a group consisting of a carbon atom, an oxygen atom, and a halogen atom; and a group consisting of a carbon atom, a hydrogen atom, an oxygen atom, and a halogen atom. When the organic group is a hydrocarbon group, the hydrocarbon group may be an aromatic hydrocarbon group, or an aliphatic hydrocarbon group, or a group including an aromatic skeleton and an aliphatic skeleton. The number of carbon atoms of the organic group is preferably 1 or more and 20 or less, more preferably 1 or more and 10 or less, and particularly preferably 1 or more and 5 or less.

Specific examples of the hydrocarbon group include chain alkyl groups such as a methyl group, an ethyl group, an n-propyl group, an isopropyl group, an n-butyl group, an isobutyl group, a sec-butyl group, a tert-butyl group, an n-pentyl group, an n-hexyl group, an n-heptyl group, an n-octyl group, a 2-ethylhexyl group, an n-nonyl group, an n-decyl group, an n-undecyl group, an n-tridecyl group, an n-tetradecyl group, an n-pentadecyl group, an n-hexadecyl group, an n-heptadecyl group, an n-octadecyl group, an n-nonadecyl group, and an n-icosyl group; chain alkenyl groups such as a vinyl group, a 1-propenyl group, a 2-n-propenyl group (allyl group), a 1-n-butenyl group, a 2-n-butenyl group, and a 3-n-butenyl group; cycloalkyl groups such as a cyclopropyl group, a cyclobutyl group, a cyclopentyl group, a cyclohexyl group, and a cycloheptyl group; aryl groups such as a phenyl group, an o-tolyl group, an m-tolyl group, a p-tolyl group, an α-naphthyl group, a β-naphthyl group, a biphenyl-4-yl group, a biphenyl-3-yl group, a biphenyl-2-yl group, an anthryl group, and a phenanthryl group; and aralkyl groups such as a benzyl group, a phenethyl group, an α-naphthylmethyl group, a β-naphthylmethyl group, an α-naphthylethyl group, and a β-naphthylethyl group.

Specific examples of the halogenated hydrocarbon group include halogenated chain alkyl groups such as a chloromethyl group, a dichloromethyl group, a trichloromethyl group, a bromomethyl group, a dibromomethyl group, a tribromomethyl group, a fluoromethyl group, a difluoromethyl group, a trifluoromethyl group, a 2,2,2-trifluoroethyl group, a pentafluoroethyl group, a heptafluoropropyl group, a perfluorobutyl group, and a perfluoropentyl group, a perfluorohexyl group, a perfluoroheptyl group, a perfluorooctyl group, a perfluorononyl group, and a perfluorodecyl group; halogenated cycloalkyl groups such as a 2-chlorocyclohexyl group, a 3-chlorocyclohexyl group, a 4-chlorocyclohexyl group, a 2,4-dichlorocyclohexyl group, a 2-bromocyclohexyl group, a 3-bromocyclohexyl group, and a 4-bromocyclohexyl group; halogenated aryl groups such as a 2-chlorophenyl group, a 3-chlorophenyl group, a 4-chlorophenyl group, a 2,3-dichlorophenyl group, a 2,4-dichlorophenyl group, a 2,5-dichlorophenyl group, a 2,6-dichlorophenyl group, a 3,4-dichlorophenyl group, a 3,5-dichlorophenyl group, a 2-bromophenyl group, a 3-bromophenyl group, a 4-bromophenyl group, a 2-fluorophenyl group, a 3-fluorophenyl group, and a 4-fluorophenyl group; and halogenated aralkyl groups such as a 2-chlorophenylmethyl group, a 3-chlorophenylmethyl group, 4-chlorophenylmethyl group, a 2-bromophenylmethyl group, a 3-bromophenylmethyl group, a 4-bromophenylmethyl group, a 2-fluorophenylmethyl group, a 3-fluorophenylmethyl group, and a 4-fluorophenylmethyl group.

Specific examples of the group consisting of a carbon atom, a hydrogen atom, and an oxygen atom include hydroxy chain alkyl groups such as a hydroxymethyl group, a 2-hydroxyethyl group, a 3-hydroxy-n-propyl group, and a 4-hydroxy-n-butyl group; halogenated cycloalkyl groups such as a 2-hydroxycyclohexyl group, a 3-hydroxycyclohexyl group, and a 4-hydroxycyclohexyl group; hydroxyaryl groups such as a 2-hydroxyphenyl group, a 3-hydroxyphenyl group, a 4-hydroxyphenyl group, a 2,3-dihydroxyphenyl group, a 2,4-dihydroxyphenyl group, a 2,5-dihydroxyphenyl group, a 2,6-dihydroxyphenyl group, a 3,4-dihydroxyphenyl group, and a 3,5-dihydroxyphenyl group; hydroxyaralkyl groups such as a 2-hydroxyphenylmethyl group, a 3-hydroxyphenylmethyl group, and a 4-hydroxyphenylmethyl group; chain alkoxy groups such as a methoxy group, an ethoxy group, an n-propoxy group, an isopropoxy group, an n-butyloxy group, an isobutyloxy group, a sec-butyloxy group, a tert-butyloxy group, an n-pentyloxy group, an n-hexyloxy group, an n-heptyloxy group, an n-octyloxy group, a 2-ethylhexyloxy group, an n-nonyloxy group, an n-decyloxy group, an n-undecyloxy group, an n-tridecyloxy group, an n-tetradecyloxy group, an n-pentadecyloxy group, an n-hexadecyloxy group, an n-heptadecyloxy group, an n-octadecyloxy group, an n-nonadecyloxy group, and an n-icosyloxy group; chain alkenyloxy groups such as a vinyloxy group, a 1-propenyloxy group, a 2-n-propenyloxy group (allyloxy group), a 1-n-butenyloxy group, a 2-n- butenyloxy group, and a 3-n-butenyloxy group; aryloxy groups such as a phenoxy group, an o-tolyloxy group, an m-tolyloxy group, a p-tolyloxy group, an α-naphthyloxy group, a β-naphthyloxy group, a biphenyl-4-yloxy group, a biphenyl-3-yloxy group, a biphenyl-2-yloxy group, an anthryloxy group, and a phenanthryloxy group; aralkyloxy groups such as a benzyloxy group, a phenethyloxy group, an α-naphthylmethyloxy group, a β-naphthylmethyloxy group, an α-naphthylethyloxy group, and a β-naphthylethyloxy group; alkoxyalkyl groups such as a methoxymethyl group, an ethoxymethyl group, an n-propoxymethyl group, a 2-methoxyethyl group, a 2-ethoxyethyl group, a 2-n-propoxyethyl group, a 3-methoxy-n-propyl group, a 3-ethoxy-n-propyl group, a 3-n-propoxy-n-propyl group, a 4-methoxy-n-butyl group, a 4-ethoxy-n-butyl group, and a 4-n-propoxy-n-butyl group; alkoxyalkoxy groups such as a methoxymethoxy group, an ethoxymethoxy group, an n-propoxymethoxy group, a 2-methoxyethoxy group, a 2-ethoxyethoxy group, a 2-n-propoxyethoxy group, a 3-methoxy-n-propoxy group, a 3-ethoxy-n-propoxy group, a 3-n-propoxy-n-propoxy group, a 4-methoxy-n-butyloxy group, a 4-ethoxy-n-butyloxy group, and a 4-n-propoxy-n-butyloxy group; alkoxyaryl groups such as a 2-methoxyphenyl group, a 3-methoxyphenyl group, and a 4-methoxyphenyl group; alkoxyaryloxy groups such as a 2-methoxyphenoxy group, a 3-methoxyphenoxy group, and a 4-methoxyphenoxy group; aliphatic acyl groups such as a formyl group, an acetyl group, a propionyl group, a butanoyl group, a pentanoyl group, a hexanoyl group, a heptanoyl group, an octanoyl group, a nonanoyl group, and a decanoyl group; aromatic acyl groups such as a benzoyl group, an α-naphthoyl group, and a β-naphthoyl group; chain alkyloxycarbonyl groups such as a methoxycarbonyl group, an ethoxycarbonyl group, an n-propoxycarbonyl group, an n-butyloxycarbonyl group, an n-pentyloxycarbonyl group, an n-hexyloxycarbonyl group, an n-heptyloxycarbonyl group, an n-octyloxycarbonyl group, an n-nonyloxycarbonyl group, and an n-decyloxycarbonyl group; aryloxycarbonyl groups such as a phenoxycarbonyl group, an α-naphthoxycarbonyl group, and a β-naphthoxycarbonyl group; aliphatic acyloxy groups such as a formyloxy group, an acetyloxy group, a propionyloxy group, a butanoyloxy group, a pentanoyloxy group, a hexanoyloxy group, a heptanoyloxy group, an octanoyloxy group, a nonanoyloxy group, and a decanoyloxy group; and aromatic acyloxy groups such as a benzoyloxy group, an α-naphthoyloxy group, and a β-naphthoyloxy group.

It is preferred that $R^{b01}$ to $R^{b018}$ be each independently a group selected from the group consisting of a hydrogen atom, a halogen atom, an alkyl group having 1 or more and 5 or less carbon atoms and an alkoxy group having 1 or more and 5 or less carbon atoms, and it is more preferred that all $R^{b01}$ to $R^{b018}$ be hydrogen atoms particularly because a cured film with good mechanical properties is easily formed.

In the formulas (b01-2) to (b01-5), $R^{b01}$ to $R^{b018}$ are the same as $R^{b01}$ to $R^{b018}$ in the formula (b01-1). Examples of the divalent group formed when $R^{b02}$ and $R^{b010}$ are bonded to each other in the formula (b01-2) and the formula (b01-4), when $R^{b013}$ and $R^{b016}$ are bonded to each other in the formula (b01-2), and when $R^{b02}$ and $R^{b08}$ are bonded to each other in the formula (b01-3) include —CH$_2$— and —C(CH$_3$)$_2$—.

Specific examples of suitable compounds of the alicyclic epoxy compound represented by the formula (b01-1) can include alicyclic epoxy compounds represented by the following formulas (b01-1a), (b01-1b) and (b01-1c), 2,2-bis(3,4-epoxycyclohexan-1-yl)propane [=2,2-bis(3,4-epoxycyclohexyl)propane], and the like.

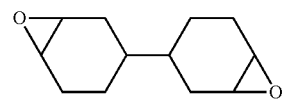

(b01-1a)

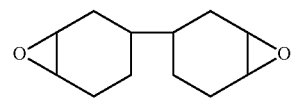

(b01-1b)

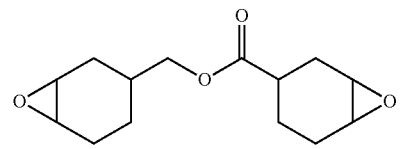

(b01-1c)

Specific examples of suitable compounds of the alicyclic epoxy compound represented by the formula (b01-2) include an alicyclic epoxy compounds represented by the following formula (b01-2a) or an alicyclic epoxy compounds represented by the following formula (b01-2b).

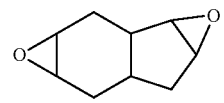

(b01-2a)

(b01-2b)

Specific examples of suitable compounds of the alicyclic epoxy compound represented by the formula (b01-3) include S-spiro[3-oxatricyclo[3.2.1.0$^{2,4}$]octane-6,2'-oxirane], and the like.

Specific examples of suitable compounds of the alicyclic epoxy compound represented by the formula (b01-4) include 4-vinylcyclohexene dioxide, dipentene dioxide, limonene dioxide, 1-methyl-4-(3-methyloxiran-2-yl)-7-oxabicyclo[4.1.0]heptane, and the like.

Specific examples of suitable compounds of the alicyclic epoxy compound represented by the formula (b01-5) include 1,2,5,6-diepoxycyclooctane, and the like.

Furthermore, a compound represented by the following formula (b1-I) can be suitably used as the epoxy compound.

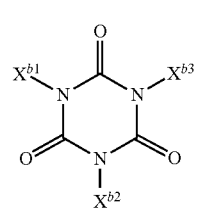

(b1-I)

In the formula (b1-I), $X^{b1}$, $X^{b2}$ and $X^{b3}$ are each independently a hydrogen atom or an organic group which may include an epoxy group, and the total number of epoxy groups of $X^{b1}$, $X^{b2}$ and $X^{b3}$ is 2 or more.

The compound represented by the above formula (b1-I) is preferably a compound represented by the following formula (b1-II).

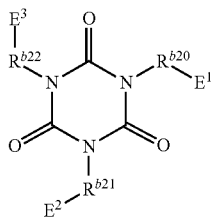

(b1-II)

In the formula (b1-II), $R^{b20}$ to $R^{b22}$ are a linear, branched or cyclic alkylene group, an arylene group, —O—, —C(=O)—, —NH— and a combination thereof, and may be the same or different. $E^1$ to $E^3$ are at least one substituent selected from the group consisting of an epoxy group, an oxetanyl group, an ethylenically unsaturated group, an alkoxysilyl group, an isocyanate group, a blocked isocyanate group, a thiol group, a carboxy group, a hydroxy group and a succinic acid anhydride group, or a hydrogen atom, provided that a number of the epoxy groups that $E^1$, $E^2$, and $E^3$ have is at least two.

In the formula (b1-II), each of at least two of a group represented by $R^{b20}$ and $E^1$, a group represented by $R^{b21}$ and $E^2$, and a group represented by $R^{b22}$ and $E^3$ is preferably a group represented by the following formula (b1-IIa). It is more preferred that all of these groups are groups represented by the following formula (b1-IIa). A plurality of groups represented by the formula (b1-IIa) bonded to one compound are preferably the same.

-L-C$^a$      (b1-IIa)

In the formula (b1-IIa), L is a linear, branched or cyclic alkylene group, an arylene group, —O—, —C(=O)—, —NH— and a combination thereof, and C$^a$ is an oxiranyl group (an epoxy group). In the formula (b1-IIa), L and C$^a$ may be combined to each other to form a cyclic structure.

In the formula (b1-IIa), the linear, branched or cyclic alkylene group as L is preferably an alkylene group having 1 or more and 10 or less carbon atoms, and additionally the arylene group as L is preferably an arylene group having 5 or more and 10 or less carbon atoms. In the formula (b1-IIa), L is preferably a linear alkylene group having 1 or more and 3 or less carbon atoms, a phenylene group, —O—, —C(=O)—, —NH— and a combination thereof, and is preferably at least one of a linear alkylene group having 1 or more and 3 or less carbon atoms such as a methylene group and a phenylene group or a combination of these groups and at least one of —O—, —C(=O)— and —NH—.

As a case where L and C$^a$ are bonded to each other to form a cyclic structure in the formula (b1-IIa), for example when a branched alkylene group and an epoxy group are bonded to each other to form a cyclic structure (a structure having an epoxy group of an alicyclic structure), examples thereof include an organic group represented by the following formulas (b1-IIb) to (b1-IId).

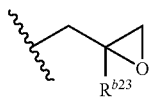

(b1-IIb)

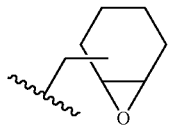

(b1-IIc)

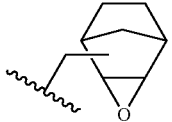

(b1-IId)

In the formula (b1-IIb), $R^{b23}$ is a hydrogen atom or a methyl group.

As examples of the compound represented by the formula (b1-II), epoxy compounds having an oxiranyl group or an alicyclic epoxy group will be exemplified. It should be noted, however, that the compound represented by the formula (b1-II) is not limited thereto.

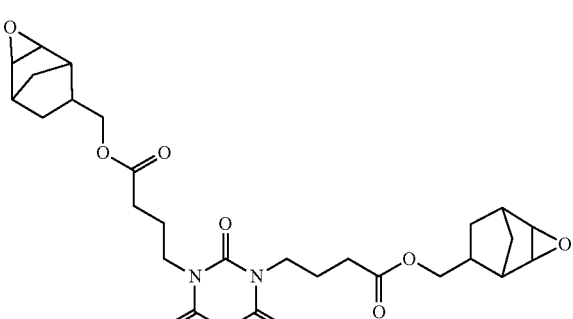

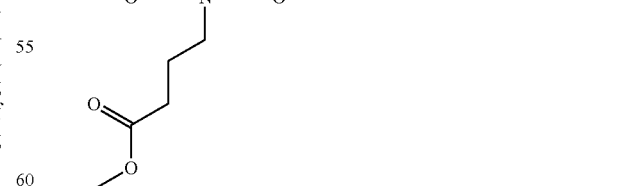

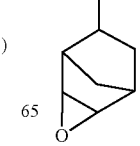

33
-continued
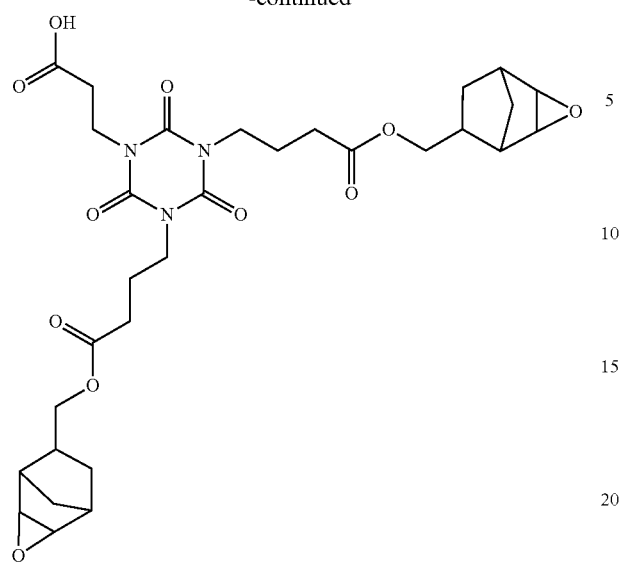
34
-continued
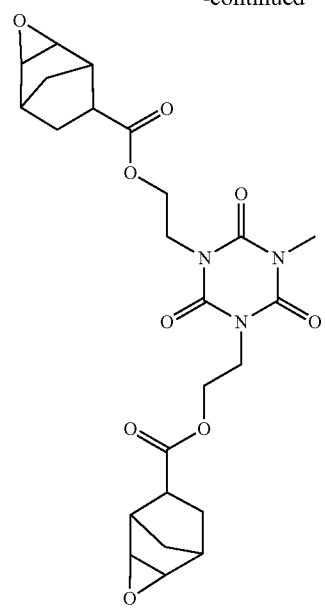
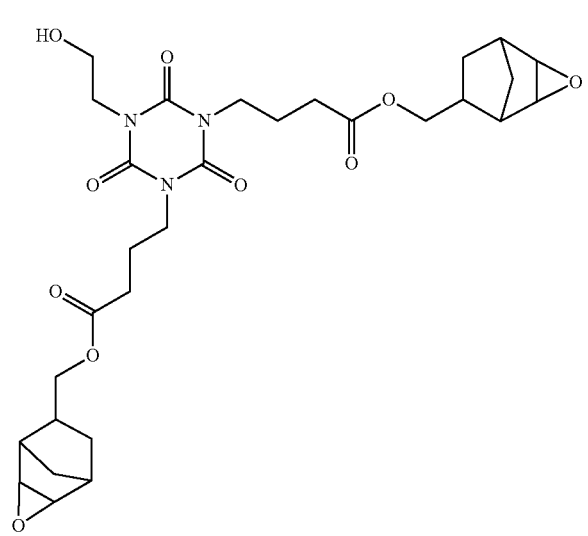
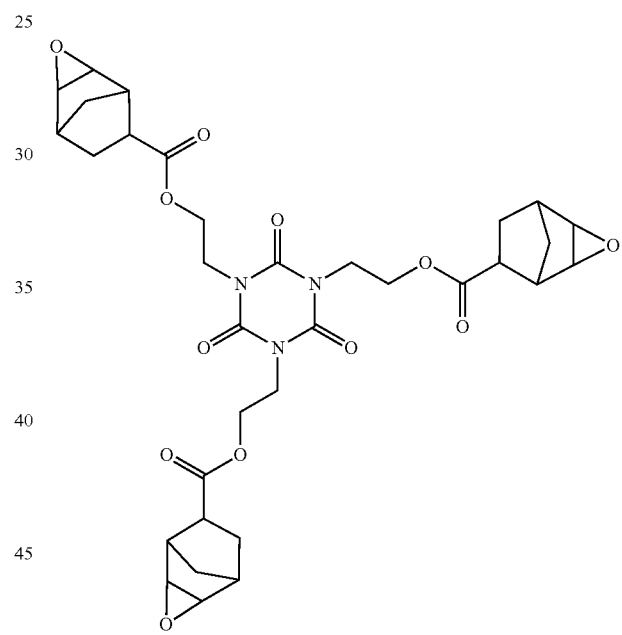
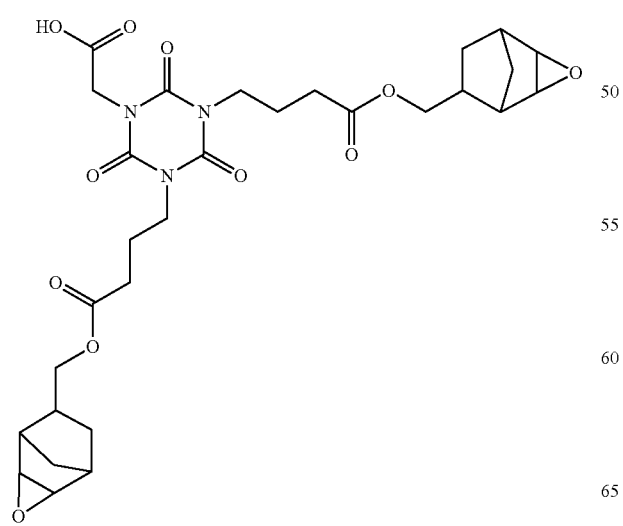
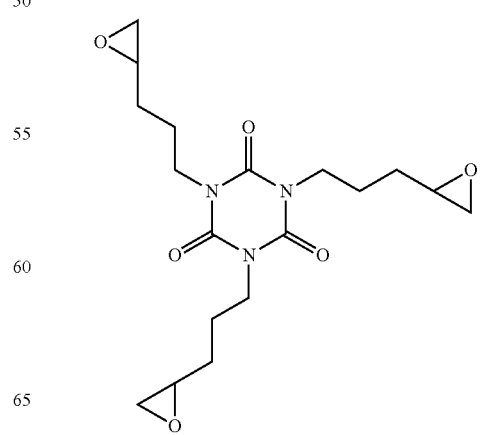

35
-continued
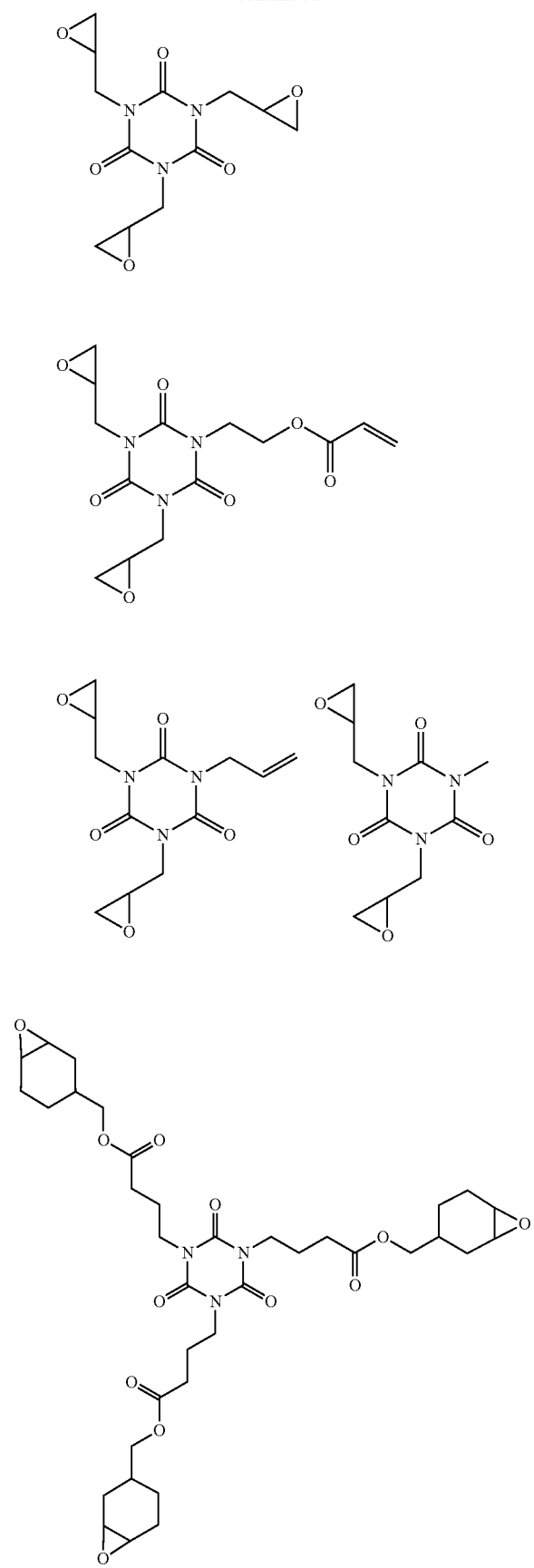
36
-continued
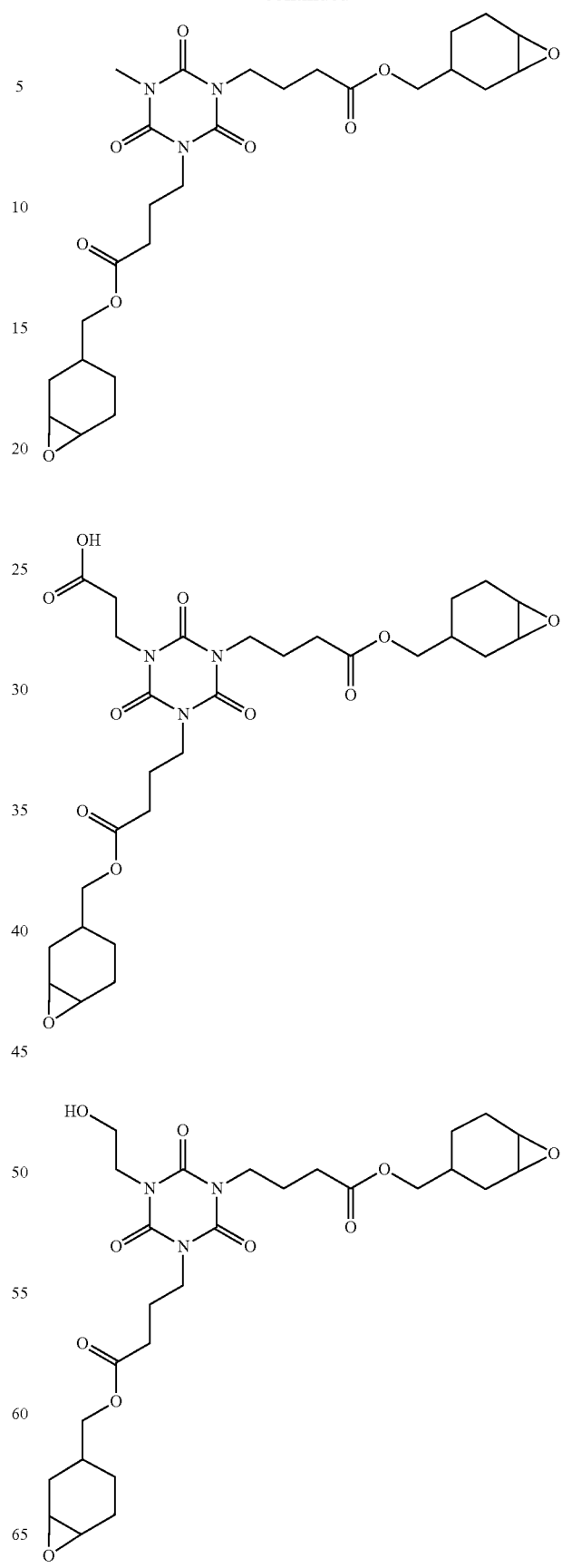

-continued

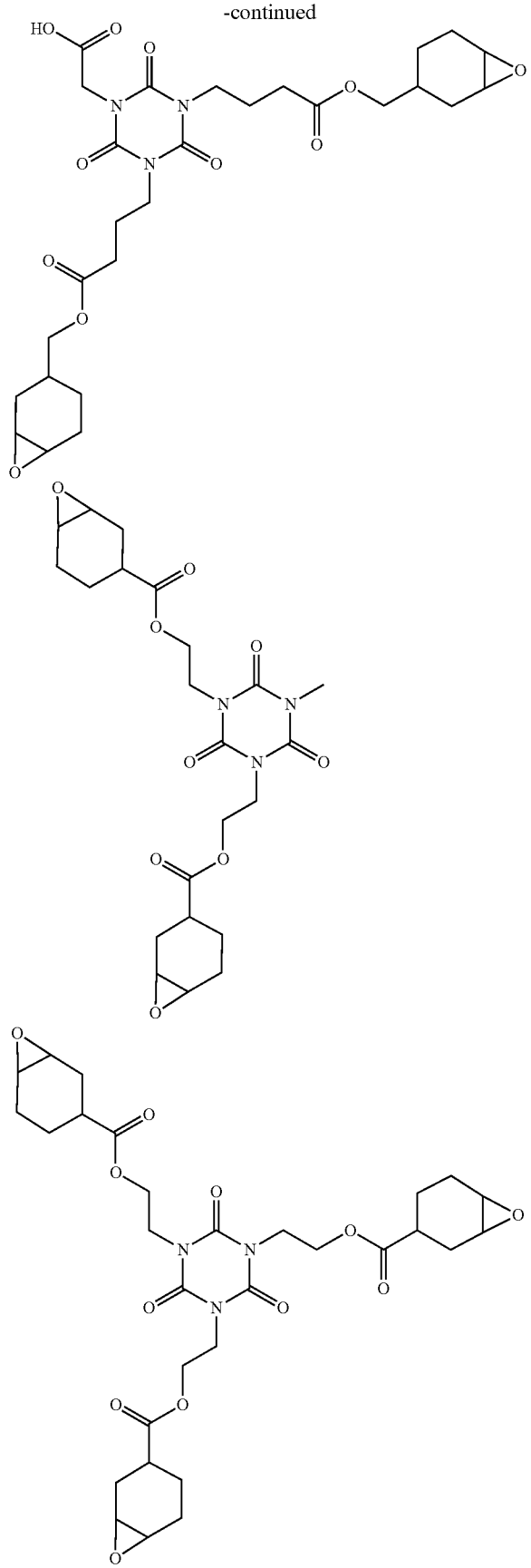

Furthermore, as a compound which can preferably be used as the epoxy compound, a siloxane compound having two or more epoxy groups in a molecule (hereinafter, also simply referred to as "siloxane compound") is exemplified.

The siloxane compound is a compound having a siloxane skeleton constituted with siloxane bonds (Si—O—Si) and two or more glycidyl groups or alicyclic epoxy groups in a molecule.

Examples of the siloxane skeleton in the siloxane compound can include a cyclic siloxane skeleton, a polysiloxane skeleton and a basket or ladder type polysilsesquioxane skeleton.

As the siloxane compound, a compound having a cyclic siloxane skeleton represented by the following formula (b1-III) (hereinafter, may be referred to as "cyclic siloxane") is preferred.

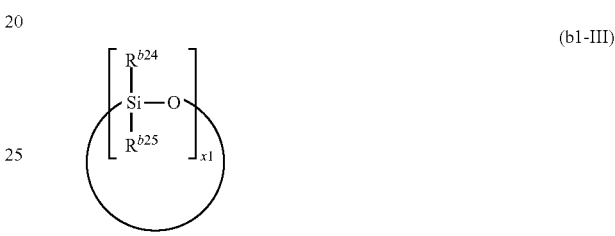

(b1-III)

In the formula (b1-III), $R^{b24}$ and $R^{b25}$ represent a monovalent group including an epoxy group, or an alkyl group. However, at least two of the x1 number of $R^{b24}$ and the x1 number of $R^{b25}$ in the compound represented by the formula (b1-III) are a monovalent group including an epoxy group. Furthermore, x1 in the formula (b1-III) represents an integer of 3 or more. It should be noted that $R^{b24}$ and $R^{b25}$ in the compound represented by the formula (b1-III) may be the same or different. In addition, a plurality of $R^{b24}$ may be the same or different. A plurality of $R^{b25}$ may also be the same or different. As the alkyl group, for example, a linear or branched alkyl group having 1 or more and 18 or less carbon atoms (preferably 1 or more and 6 or less carbon atoms, and more preferably 1 or more and 3 or less carbon atoms) such as a methyl group, an ethyl group, a propyl group, and an isopropyl group are exemplified.

In the formula (b1-III), x1 represents an integer of 3 or more, and particularly preferably an integer of 3 or more and 6 or less from the viewpoint of good crosslinking reactivity when a cured film is formed. The number of epoxy groups in the molecule of the siloxane compound is 2 or more, and preferably 2 or more and 6 or less, and particularly preferably 2 or more and 4 or less from the viewpoint of good crosslinking reactivity when a cured film is formed.

The above monovalent group including an epoxy group is preferably an alicyclic epoxy group and a glycidyl ether group represented by -$D^A$-O—$R^{b26}$ [where $D^A$ represents an alkylene group, and $R^{b26}$ represents a glycidyl group.], more preferably the alicyclic epoxy group, and further preferably an alicyclic epoxy group represented by the following formula (b1-IIIa) or the following formula (b-IIIb). Examples of the above $D^A$(alkylene group) can include linear or branched alkylene groups having 1 or more and 18 or less carbon atoms such as a methylene group, a methylmethylene group, a dimethylmethylene group, a dimethylene group and a trimethylene group, and the like.

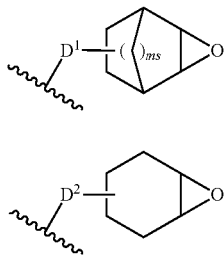

(b1-IIIa)

(b1-IIIb)

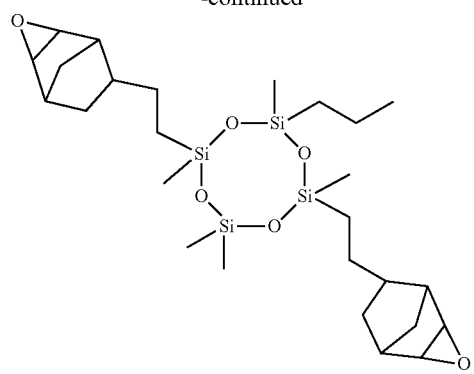

In the formula (b1-IIIa) and the formula (b1-IIIb), D1 and D2 each independently represents an alkylene group, and ms represents an integer of 0 or more and 2 or less.

The curable composition may include, in addition to the siloxane compound represented by the formula (b1-III), compounds having a siloxane skeleton such as alicyclic epoxy group-containing cyclic siloxane, an alicyclic epoxy group-containing silicone resin described in Japanese Unexamined Patent Application Publication No. 2008-248169, and an organopolysilsesquioxane resin having at least two epoxy functional groups in one molecule described in Japanese Unexamined Patent Application Publication No. 2008-19422.

More specific examples of the siloxane compound can include cyclic siloxane having two or more epoxy groups in a molecule represented by the following formulas, and the like. In addition, commercial products such as trade name "X-40-2670," "X-40-2701," "X-40-2728," "X-40-2738" and "X-40-2740" (all manufactured by Shinetsu Chemical Co., Ltd.), for example, can be used as the siloxane compound.

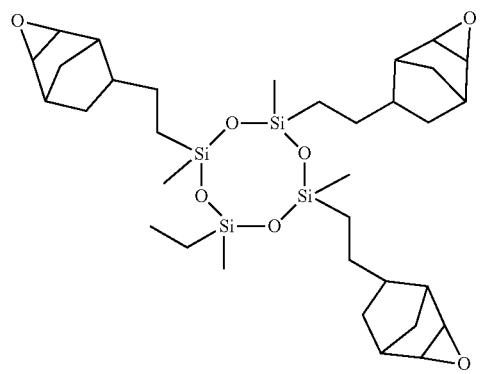

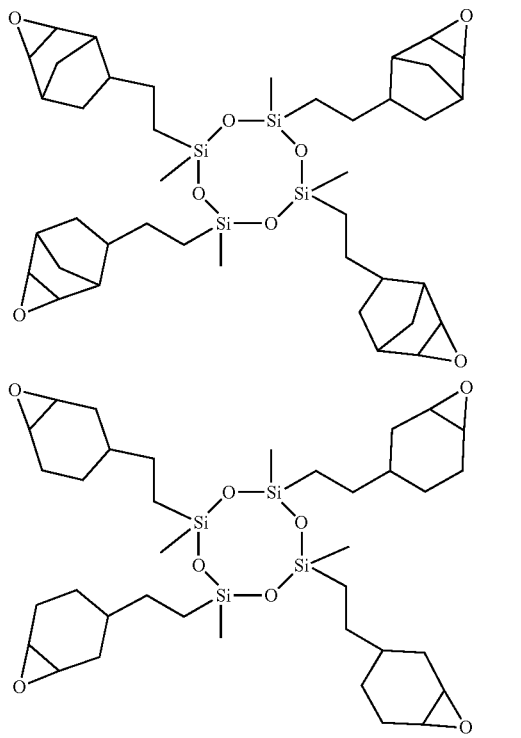

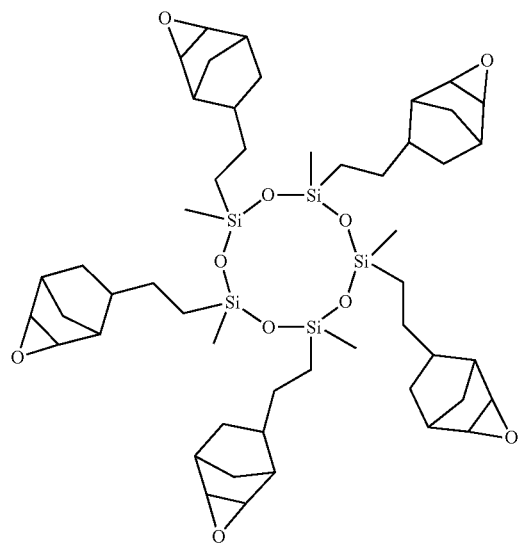

41
-continued
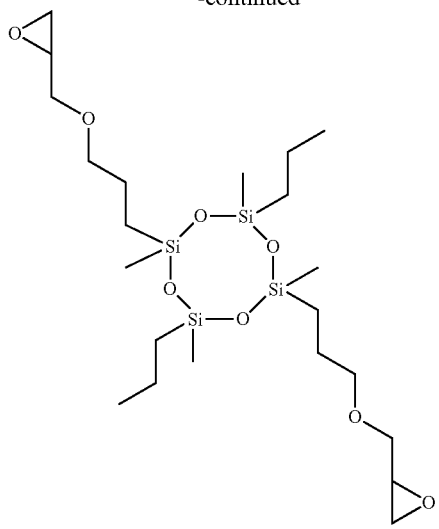
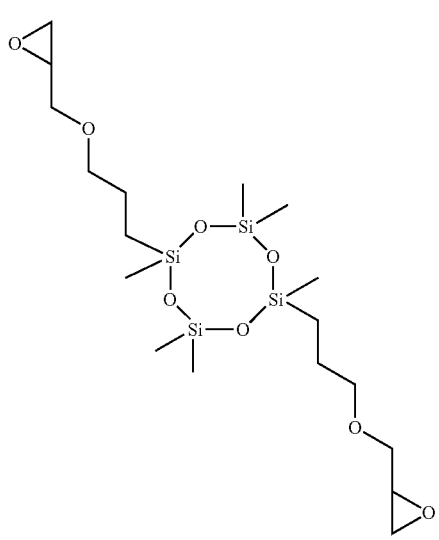
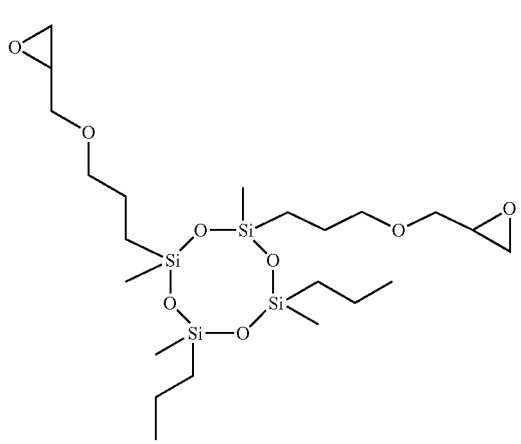
42
-continued
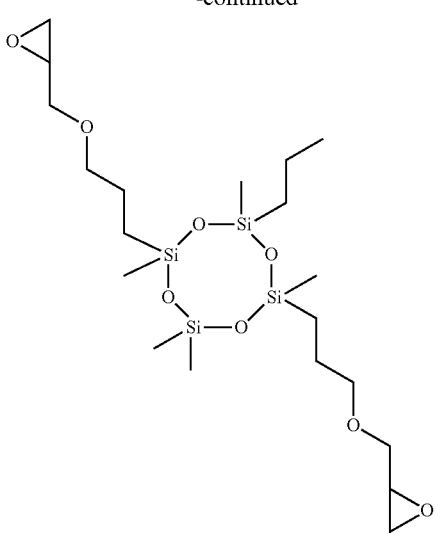
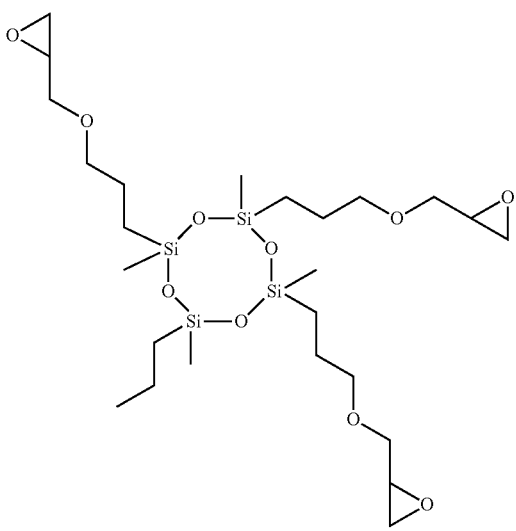
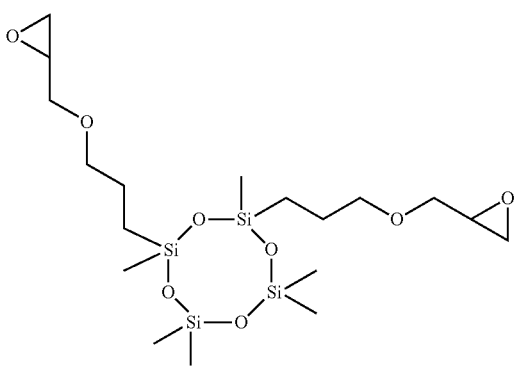

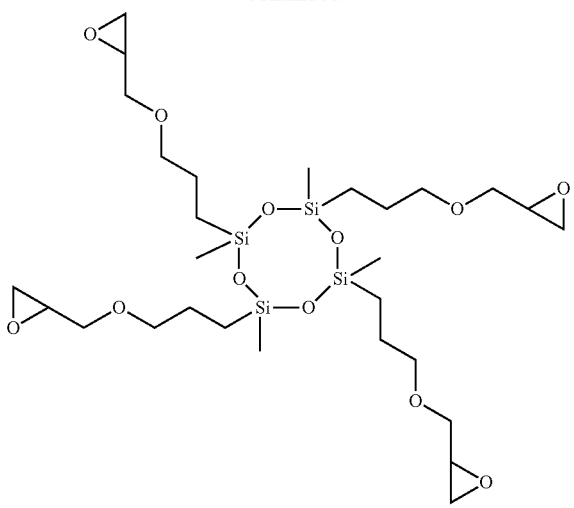

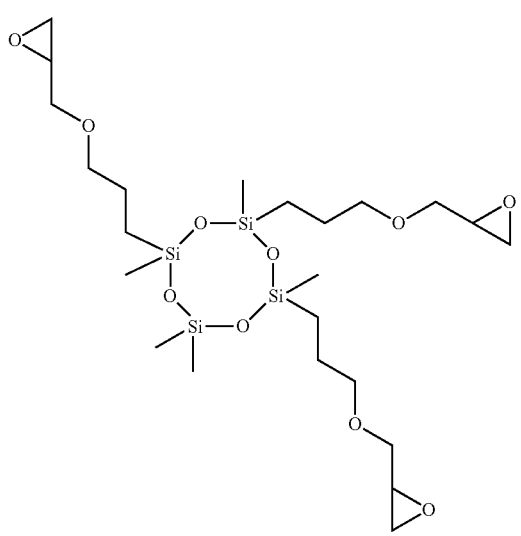

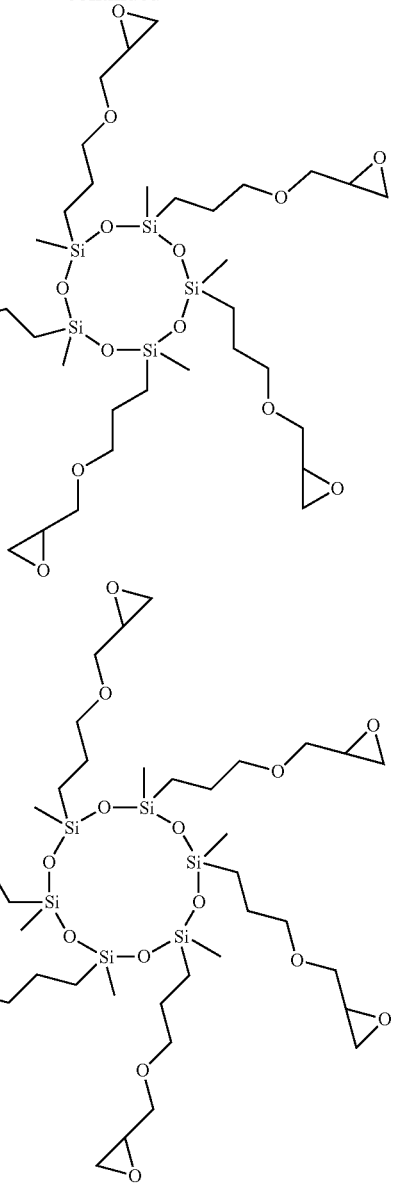

The content of the polymerizable compound (B) in the curable composition is not particularly limited as long as the desired effect is not impaired. The content of the polymerizable compound (B) in the curable composition relative to 100 parts by mass of the mass of the curable composition excluding the mass of the solvent (S) described later is preferably 0.1 parts by mass or more and 50 parts by mass or less, more preferably 0.5 parts by mass or more and 40 parts by mass or less, and even more preferably 1 part by mass or more and 25 parts by mass or less.

<Initiator (C)>

In order to cure the heterocyclic compound (A) or the heterocyclic compound (A) and the polymerizable compound (B), the curable composition contains the initiator (C). When the heterocyclic compound (A) and the curable compound (B) have a radically polymerizable group, a radical polymerization initiator (C1) is used as the initiator (C). When the heterocyclic compound (A) and the curable compound (B) have a cationically polymerizable group, a cationic polymerization initiator (C2) is used as the initiator (C). The initiator (C) may be a thermal initiator or a photo initiator. Since regioselective curing of the curable composition is capable, and there is no concern about thermal degradation, volatilization, or sublimation of the components of the curable composition, the photo initiator is preferred as the initiator (C). The initiator (C) is not particularly limited and various polymerization initiator conventionally known can be used.

Specific examples of the photo radical polymerization initiator useful as useful as the radically polymerization initiator (C1) include 1-hydroxycyclohexyl phenyl ketone, 2-hydroxy-2-methyl-1-phenylpropan-1-one, 1-[4-(2-hydroxyethoxy)phenyl]-2-hydroxy-2-methyl-1-propan-1-one, 1-(4-isopropylphenyl)-2-hydroxy-2-methylpropan-1-one, 1-(4-dodecylphenyl)-2-hydroxy-2-methylpropan-1-one, 2,2-dimethoxy-1,2-diphenylethan-1-one, bis(4-dimethylaminophenyl) ketone, 2-methyl-1-[4-(methylthio)phenyl]-2-morpholinopropan-1-one, 2-benzyl-2-dimethylamino-1-(4-morpholinophenyl)-butan-1-one, O-acetyl-1-[6-(2-methylbenzoyl)-9-ethyl-9H-carbazol-3-yl]ethanone oxime, (9-ethyl-6-nitro-9H-carbazol-3-yl)[4-(2-methoxy-1-methylethoxy)-2-methylphenyl]methanon 0-acetyloxime, 1,2-octanedione, 2-(benzoyloxyimino)-1-[4-(phenylthio)phenyl]-1-octanone, 2,4,6-trimethylbenzoyldiphenylphosphine oxide, 4-benzoyl-4'-methyldimethyl sulfide, 4-dimethylaminobenzoic acid, methyl 4-dimethylaminobenzoate, ethyl 4-dimethylaminobenzoate, butyl 4-dimethylaminobenzoate, 4-dimethylamino-2-ethylhexylbenzoic acid, 4-dimethylamino-2-isoamylbenzoic acid, benzyl-β-methoxyethyl acetal, benzyl dimethyl ketal, 1-phenyl-1,2-propanedion-2-(O-ethoxycarbonyl) oxime, methyl o-benzoylbenzoate, 2,4-diethylthioxanthone, 2-chlorothioxanthone, 2,4-dimethylthioxanthone, 1-chloro-4-propoxythioxanthone, thioxanthene, 2-chlorothioxanthene, 2,4-diethylthioxanthene, 2-methylthioxanthene, 2-isopropylthioxanthene, 2-ethylanthraquinone, octamethylanthraquinone, 1,2-benzanthraquinone, 2,3-diphenylanthraquinone, azobisisobutyronitrile, benzoyl peroxide, cumene hydroperoxide, 2-mercaptobenzimidazole, 2-mercaptobenzoxazole, 2-mercaptobenzothiazole, 2-(o-chlorophenyl)-4,5-di(m-methoxyphenyl)-imidazolyl dimer, benzophenone, 2-chlorobenzophenone, p,p'-bisdimethylaminobenzophenone, 4,4'-bisdiethylaminobenzophenone, 4,4'-dichlorobenzophenone, 3,3-dimethyl-4-methoxybenzophenone, benzil, benzoin, benzoin methyl ether, benzoin ethyl ether, benzoin isopropyl ether, benzoin-n-butyl ether, benzoin isobutyl ether, benzoin butyl ether, acetophenone, 2,2-diethoxyacetophenone, p-dimethylacetophenone, p-dimethylaminopropiophenone, dichloroacetophenone, trichloroacetophenone, p-tert-butylacetophenone, p-dimethylaminoacetophenone, p-tert-butyltrichloroacetophenone, p-tert-butyldichloroacetophenone, α,α-dichloro-4-phenoxyacetophenone, thioxanthone, 2-methylthioxanthone, 2-isopropylthioxanthone, dibenzosuberone, pentyl 4-dimethylaminobenzoate, 9-phenylacridine, 1,7-bis-(9-acridinyl)heptane, 1,5-bis-(9-acridinyl)pentane, 1,3-bis-(9-acridinyl)propane, p-methoxytriazine, 2,4,6-tris(trichloromethyl)-s-triazine, 2-methyl-4,6-bis(trichloromethyl)-s-triazine, 2-[2-(5-methylfuran-2-yl)ethenyl]-4,6-bis(trichloromethyl)-s-triazine, 2-[2-(furan-2-yl)ethenyl]-4,6-bis(trichloromethyl)-s-triazine, 2-[2-(4-diethylamino-2-methylphenyl)ethenyl]-4,6-bis(trichloromethyl)-s-triazine, 2-[2-(3,4-dimethoxyphenyl)ethenyl]-4,6-bis(trichloromethyl)-s-triazine, 2-(4-methoxyphenyl)-4,6-bis(trichloromethyl)-s-triazine, 2-(4-ethoxystyryl)-4,6-bis(trichloromethyl)-s-triazine, 2-(4-n-butoxyphenyl)-4,6-bis(trichloromethyl)-s-triazine, 2,4-bis-trichloromethyl-6-(3-bromo-4-methoxy)phenyl-s-triazine, 2,4-bis-trichloromethyl-6-(2-bromo-4-methoxy)phenyl-s-triazine, 2,4-bis-trichloromethyl-6-(3-bromo-4-methoxy)styrylphenyl-s-triazine, 2,4-bis-trichloromethyl-6-(2-bromo-4-methoxy)styrylphenyl-s-triazine, and the like. These photo radical polymerization initiators may be used either individually or in combination of two or more.

Among photo radical polymerization initiators, an oxime ester compound is preferable from the viewpoint of sensitivity of the curable composition. A compound including the partial structure represented by the formula (c1) is preferable as the oxime ester compound.

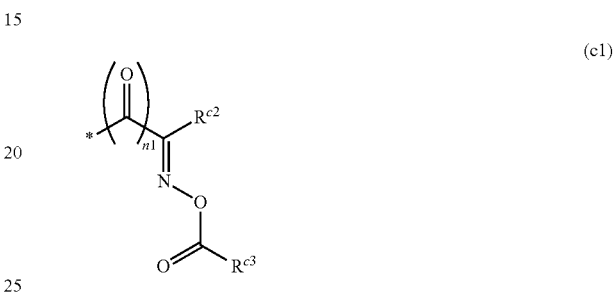

(c1)

In the formula (c1), n1 is 0 or 1, $R^{c2}$ is a monovalent organic group, $R^{c3}$ is a hydrogen atom, an optionally substituted aliphatic hydrocarbon group having 1 or more and 20 or less carbon atoms, or an optionally substituted aryl group, and

* represents a bond.

The compound including the partial structure represented by the formula (c1) preferably has a carbazole skeleton, a fluorene skeleton, a diphenyl ether skeleton, or a phenyl sulfide skeleton. The compound including the partial structure represented by the formula (c1) preferably has 1 or 2 partial structures represented by the formula (c1).

Examples of the compound including the partial structure represented by the formula (c1) includes a compound represented by the following formula (c2).

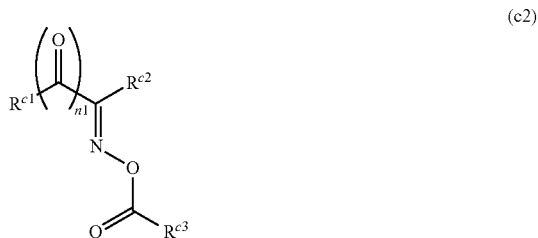

(c2)

In the formula (c2), $R^{c1}$ is a group represented by following formula (c3), (c4) or (c5), n1 is 0 or 1, $R^{c2}$ is a monovalent organic group, and $R^{c3}$ is a hydrogen atom, an optionally substituted aliphatic hydrocarbon group having 1 or more and 20 or less carbon atoms, or an optionally substituted aryl group.

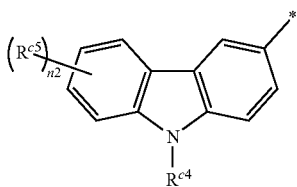

(c3)

In the formula (c3), $R^{c4}$ and RCS are each independently a monovalent organic group, n2 is an integer of 0 or more and 3 or less, and when n2 is 2 or 3, plural $R^{c5}$s may be the same as or different each other, and plural $R^{c5}$s may be combined to each other to form a ring. * represents a bond.

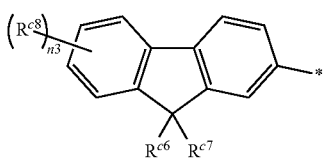

(c4)

In the formula (c4), $R^{c6}$ and $R^{c7}$ are each independently an optionally substituted chain alkyl group, an optionally substituted chain alkoxy group, an optionally substituted cyclic organic group, or a hydrogen atom, $R^{c6}$ and $R^{c7}$ may be combined to each other to form a ring, $R^{c7}$ and a benzene ring in the fluorene skeleton may be combined to each other to form a ring, $R^{c8}$ is a nitro group, or a monovalent organic group, n3 is an integer of 0 or more and 4 or less, and

* represents a bond.

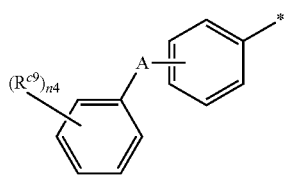

(c5)

In the formula (c5), $R^{c9}$ is a monovalent organic group, a halogen atom, a nitro group, or a cyano group, A is S or O, n4 is an integer of 0 or more and 4 or less, and

* represents a bond.

In the formula (c3), $R^{c4}$ is the monovalent organic group. $R^{c4}$ can be selected from various kinds of organic groups as far as objects of the present invention are not inhibited. As the organic group, a carbon atom-containing group is preferred, and a group consisting of 1 or more carbon atoms, and 1 or more atoms selected from the group consisting of H, O, S, Se, N, B, P, Si and a halogen atom is more preferred. The number of carbon atoms of the carbon atom-containing group is not particularly limited, and is preferably 1 or more and 50 or less, and more preferably 1 or more and 20 or less. Suitable examples of $R^{c4}$ include an optionally substituted alkyl group having 1 or more and 20 or less carbon atoms, an optionally substituted cycloalkyl group having 3 or more an 20 or less carbon atoms, an optionally substituted saturated aliphatic acyl group having 2 or more and 20 or less carbon atoms, an optionally substituted alkoxycarbonyl group having 2 or more and 20 or less carbon atoms, an optionally substituted phenyl group, an optionally substituted benzoyl group, an optionally substituted phenoxycarbonyl group, an optionally substituted phenylalkyl group having 7 or more and 20 or less carbon atoms, an optionally substituted naphthoyl group, an optionally substituted naphthoxycarbonyl group, an optionally substituted naphthylalkyl group having 11 or more and 20 or less carbon atoms, an optionally substituted heterocyclyl group, an optionally substituted heterocyclylcarbonyl group, and the like.

Among $R^{c4}$s, the alkyl group having 1 or more and 20 or less carbon atoms. The alkyl group may be straight or branched. The number of carbon atoms of the alkyl group as Rc4 is preferably 2 or more, more preferably 5 or more, and particularly preferably 7 or more, from the viewpoint of good solubility of the compound represented by the formula (c3) in the curable composition. From the viewpoint of good compatibility between the compound represented by the formula (c3) and other components in the curable composition, the number of carbon atoms of the alkyl group as $R^{c4}$ is preferably 15 or less, and more preferably 10 or less.

When $R^{c4}$ has a substituent, suitable examples of the substituent is a hydroxy group, an alkyl group having 1 or more and 20 or less carbon atoms, an alkoxy group having 1 or more and 20 or less carbon atoms, an aliphatic acyl group having 2 or more and 20 or less carbon atoms, an aliphatic acyloxy group having 2 or more and 20 or less carbon atoms, a phenoxy group, a benzoyl group, a benzoyloxy group, a group represented by —PO(OR)$_2$ (in which, R is an alkyl group having 1 or more and 6 or less carbon atoms), a halogen atom, a cyano group, a heterocyclyl group, and the like.

When $R^{c4}$ is a heterocyclyl group, the heterocyclyl group may be an aliphatic heterocyclic group or an aromatic heterocyclic group. When $R^{c4}$ is the heterocyclyl group, the heterocyclyl group is a 5- or 6-membered single ring containing one or more N, S, and O, or a heterocyclyl group in which single rings are fused each other, or a single ring is fused with a benzene ring. When the heterocyclyl group is a fused ring, the number of rings constituting the fused ring is 3 or less. Examples of the heterocycle constituting the heterocyclyl group include furan, thiophene, pyrrole, oxazole, isoxazole, thiazole, thiadiazole, isothiazole, imidazole, pyrazole, triazole, pyridine, pyrazine, pyrimidine, pyridazine, benzofuran, benzothiophene, indole, isoindole, indolizine, benzoimidazole, benzotriazole, benzoxazole, benzothiazole, carbazole, purine, quinoline, isoquinoline, quinazoline, phthalazine, cinnoline, quinoxaline, piperidine, piperazine, morpholine, tetrahydropyran, tetrahydrofuran, and the like. When $R^{c4}$ is the heterocyclyl group, examples of substituent that the heterocyclyl group may have include a hydroxy group, an alkoxy group having 1 or more and 6 or less carbon atoms, a halogen atom, a cyano group, a nitro group, and the like.

Suitable examples of above described $R^{c4}$ include a methyl group, an ethyl group, an n-propyl group, an isopropyl group, an n-butyl group, an isobutyl group, a sec-butyl group, a tert-butyl group, an n-pentyl group, an isopentyl group, a neopentyl group, a pentane-3-yl group, a sec-pentyl group, a tert-pentyl group, an n-hexyl group, an n-heptyl group, an n-octyl group and a 2-ethylhexyl group. The n-octyl group and the 2-ethylhexyl group is preferable, and the 2-ethylhexyl group is more preferable, from the viewpoint of good solubility of the compound represented by the formula (c3) in the curable composition.

In the formula (c3), RCS is a monovalent organic group. $R^{c5}$ can be selected from various organic groups as long as it does not interfere with the object of the present invention. As the organic group, a carbon atom-containing group is preferred, and a group consisting of 1 or more carbon atoms, and 1 or more atoms selected from the group consisting of H, O, S, Se, N, B, P, Si and a halogen atom is more preferred. The number of carbon atoms of the carbon atom-containing group is not particularly limited, and preferably 1 or more and 50 or less, and more preferably 1 or more and 20 or less. Examples of the organic group suitable for $R^{c5}$ include an alkyl group, an alkoxy group, a cycloalkyl group, a cycloalkoxy group, a saturated aliphatic acyl group, an alkoxycarbonyl group, a saturated aliphatic acyloxy group, an optionally substituted phenyl group, an optionally substituted phenoxy group, an optionally substituted benzoyl group, an optionally substituted phenoxycarbonyl group, an optionally substituted benzoyloxy group, an optionally substituted phenylalkyl group, an optionally substituted naphthyl group, an optionally substituted naphthoxy group, an optionally substituted naphthoyl group, an optionally substituted naphthoxycarbonyl group, an optionally substituted naphthoyloxy group, an optionally substituted naphthylalkyl group, an optionally substituted heterocyclyl group, an optionally substituted heterocyclylcarbonyl group, an amino group substituted with 1 or 2 organic groups, a morpholine-1-yl group, a piperazine-1-yl group, a halogen atom, a nitro group, a cyano group, a substituent including a group represented by $HX_2C—$ or $H_2XC—$ (in which, X is each independently a halogen atom), and the like.

When $R^{c5}$ is the alkyl group, a number of carbon atoms of the alkyl group is preferably 1 or more and 20 or less, and more preferably 1 or more and 6 or less. When $R^{c5}$ is the alkyl group, the alkyl group may be linear or branched. Specific examples of the alkyl group as $R^{c5}$ include a methyl group, an ethyl group, an n-propyl group, an isopropyl group, an n-butyl group, an isobutyl group, a sec-butyl group, a tert-butyl group, an n-pentyl group, an isopentyl group, a sec-pentyl group, a tert-pentyl group, an n-hexyl group, an n-heptyl group, an n-octyl group, an isooctyl group, a sec-octyl group, a tert-octyl group, an n-nonyl group, an isononyl group, an n-decyl group, an isodecyl group, and the like. When $R^{c5}$ is alkyl group, the alkyl group may contain an ether bond (—O—) in the carbon chain. Examples of the alkyl group having an ether bond in a carbon chain include a methoxyethyl group, an ethoxyethyl group, a methoxyethoxyethyl group, an ethoxyethoxyethyl group, a propyloxyethoxyethyl group, and a methoxypropyl group.

When $R^{c5}$ is the alkoxy group, the number of carbon atoms of the alkoxy group is preferably 1 or more and 20 or less, and more preferably 1 or more and 6 or less. When $R^{c5}$ is the alkoxy group, the alkoxy group may be linear or branched. When $R^{c5}$ is the alkoxy groups, specific examples thereof include a methoxy group, an ethoxy group, an n-propyloxy group, an isopropyloxy group, an n-butyloxy group, an isobutyloxy group, a sec-butyloxy group, a tert-butyloxy group, an n-pentyloxy group, an isopentyloxy group, a sec-pentyloxy group, a tert-pentyloxy group, an n-hexyloxy group, an n-heptyloxy group, an n-octyloxy group, an isooctyloxy group, a sec-octyloxy group, a tert-octyloxy group, an n-nonyloxy group, an isononyloxy group, an n-decyloxy group, an isodecyloxy group, and the like. When $R^{c5}$ is the alkoxy groups, the alkoxy group may have an ether bond (—O—) in a carbon chain. Examples of the alkoxy group having an ether bond in a carbon chain include a methoxyethoxy group, an ethoxyethoxy group, a methoxyethoxyethoxy group, an ethoxyethoxyethoxy group, a propyloxyethoxyethoxy group, and a methoxypropyloxy group.

When $R^{c5}$ is the cycloalkyl group or the cycloalkoxy group, the number of carbon atoms of the cycloalkyl group or the cycloalkoxy group is preferably 3 or more and 10 or less, and more preferably 3 or more and 6 or less. Specific examples of the cycloalkyl group as $R^{c5}$ include a cyclopropyl group, a cyclobutyl group, a cyclopentyl group, a cyclohexyl group, a cycloheptyl group, a cyclooctyl group, and the like. Specific examples of the cycloalkoxy group as $R^{c5}$ include a cyclopropyloxy group, a cyclobutyloxy group, a cyclopentyloxy group, a cyclohexyloxy group, a cycloheptyloxy group, a cyclooctyloxy group, and the like.

When $R^{c5}$ is a saturated aliphatic acyl group or a saturated aliphatic acyloxy group, the number of carbon atoms is preferably 2 or more and 21 or less, and more preferably 2 or more and 7 or less. When $R^{c5}$ is a saturated aliphatic acyl group, specific examples thereof include an acetyl group, a propanoyl group, an n-butanoyl group, a 2-methylpropanoyl group, an n-pentanoyl group, a 2,2-dimethylpropanoyl group, an n-hexanoyl group, an n-heptanoyl group, an n-octanoyl group, an n-nonanoyl group, an n-decanoyl group, an n-undecanoyl group, an n-dodecanoyl group, an n-tridecanoyl group, an n-tetradecanoyl group, an n-pentadecanoyl group, and an n-hexadecanoyl group. When $R^{c5}$ is a saturated aliphatic acyloxy group, specific examples thereof include an acetyloxy group, a propanoyloxy group, an n-butanoyloxy group, a 2-methylpropanoyloxy group, an n-pentanoyloxy group, a 2,2-dimethylpropanoyloxy group, an n-hexanoyloxy group, an n-heptanoyloxy group, an n-octanoyloxy group, an n-nonanoyloxy group, an n-decanoyloxy group, an n-undecanoyloxy group, an n-dodecanoyloxy group, an n-tridecanoyloxy group, an n-tetradecanoyloxy group, an n-pentadecanoyloxy group, and an n-hexadecanoyloxy group.

When $R^{c5}$ is an alkoxycarbonyl group, the number of carbon atoms is preferably 2 or more and 20 or less, and preferably 2 or more and 7 or less. When $R^{c5}$ is an alkoxycarbonyl group, specific examples thereof include a methoxycarbonyl group, an ethoxycarbonyl group, an n-propyloxycarbonyl group, an isopropyloxycarbonyl group, an n-butyloxycarbonyl group, an isobutyloxycarbonyl group, a sec-butyloxycarbonyl group, a tert-butyloxycarbonyl group, an n-pentyloxycarbonyl group, an isopentyloxycarbonyl group, a sec-pentyloxycarbonyl group, a tert-pentyloxycarbonyl group, an n-hexyloxycarbonyl group, an n-heptyloxycarbonyl group, an n-octyloxycarbonyl group, an isooctyloxycarbonyl group, a sec-octyloxycarbonyl group, a tert-octyloxycarbonyl group, an n-nonyloxycarbonyl group, an isononyloxycarbonyl group, an n-decyloxycarbonyl group, and an isodecyloxycarbonyl group.

When $R^{c5}$ is a phenylalkyl group, the number of carbon atoms is preferably 7 or more and 20 or less, and more preferably 7 or more and 10 or less. When RCS is a naphthylalkyl group, the number of carbon atoms is preferably 11 or more and 20 or less, and more preferably 11 or more and 14 or less. When RCS is a phenylalkyl group, specific examples thereof include a benzyl group, a 2-phenylethyl group, a 3-phenylpropyl group, and a 4-phenylbutyl group. When RCS is a naphthylalkyl group, specific examples thereof include an α-naphthylmethyl group, a β-naphthylmethyl group, a 2-(α-naphthyl)ethyl group, and a 2-(β-naphthyl)ethyl group. When $R^{c5}$ is a phenylalkyl group or a naphthylalkyl group, RCS may further have a substituent on a phenyl group or a naphthyl group.

When $R^{c5}$ is a heterocyclyl group, the heterocyclyl group is the same as the heterocyclyl group as $R^{c4}$ in the formula (c3), and may further have a substituent. When $R^{c5}$ is a heterocyclylcarbonyl group, the heterocyclyl group included in the heterocyclylcarbonyl group is the same as the heterocyclyl group as $R^{c5}$.

When $R^{dc5}$ is an amino group substituted with one or two organic groups, suitable examples of the organic groups include an alkyl group having 1 or more and 20 or less carbon atoms, a cycloalkyl group having 3 or more and 10 or less carbon atoms, a saturated aliphatic acyl group having 2 or more and 21 or less carbon atoms, an optionally substituted phenyl group, an optionally substituted benzoyl group, an optionally substituted phenylalkyl group having 7 or more and 20 or less carbon atoms, an optionally substituted naphthyl group, an optionally substituted naphthoyl group, an optionally substituted naphthylalkyl group having 11 or more and 20 or less carbon atoms, and a heterocyclyl group. Specific examples of these suitable organic group are the same as $R^{c5}$. Specific examples of the amino group substituted with one or two organic groups include a methylamino group, an ethylamino group, a diethylamino group, an n-propylamino group, a di-n-propylamino group, an isopropylamino group, an n-butylamino group, a di-n-butylamino group, an n-pentylamino group, an n-hexylamino group, an n-heptylamino group, an n-octylamino group, an n-nonylamino group, an n-decylamino group, a phenylamino group, a naphthylamino group, an acetylamino group, a propanoylamino group, an n-butanoylamino group, an n-pentanoylamino group, an n-hexanoylamino group, an n-heptanoylamino group, an n-octanoylamino group, an n-decanoylamino group, a benzoylamino group, an α-naphthoylamino group, and a β-naphthoylamino group.

When the phenyl group, the naphthyl group, and the heterocyclyl group included in $R^{c5}$ further have a substituent, examples of the substituent include a substituent including a group represented by $HX_2C$— or $H_2XC$— (for example, a halogenated alkoxy group including a group represented by $HX_2C$— or $H_2XC$—, and a halogenated alkyl group including a group represented by $HX_2C$— or $H_2XC$—), an alkyl group having 1 or more and 6 or less carbon atoms, an alkoxy group having 1 or more and 6 or less carbon atoms, a saturated aliphatic acyl group having 2 or more and 7 or less carbon atoms, an alkoxycarbonyl group having 2 or more and 7 or less carbon atoms, a saturated aliphatic acyloxy group having 2 or more and 7 or less carbon atoms, a monoalkyl group having an alkyl group having 1 or more and 6 or less carbon atoms, a dialkyl amino group having alkyl groups having 1 or more and 6 or less carbon atoms, a morpholine-1-yl group, a piperazine-1-yl group, a benzoyl group, a halogen atom, a nitro group, a cyano group, and the like. When the phenyl group, the naphthyl group, and the heterocyclyl group included in $R^{c5}$ further having one or more substituents, the number of substituents is not particularly limited as long as it does not interfere with the object of the present invention, and is preferably 1 or more and 4 or less. When a phenyl group, a naphthyl group, and a heterocyclyl group included in RCS have a plurality of substituents, the plurality of substituents may be the same or different.

When a benzoyl group, a naphthyl group included in $R^cS$ further have a substituent, examples of the substituent include an alkyl group having 1 or more and 6 or less carbon atoms, a morpholine-1-yl group, a piperazine-1-yl group, a 2-thenoyl group (thiophen-2-ylcarbonyl group), a furan-3-ylcarbonyl group, a phenyl group, and the like.

As a halogen atom represented by X, a fluorine atom, a chlorine atom, a bromine atom, and the like are exemplified, and the fluorine atom is preferred.

As a substituent including a group represented by $HX_2C$— or $H_2XC$—, a halogenated alkoxy group including a group represented by $HX_2C$— or $H_2XC$—, a group having a halogenated alkoxy group including a group represented by $HX_2C$— or $H_2XC$—, a halogenated alkyl group including a group represented by $HX_2C$— or $H_2XC$—, a group having a halogenated alkyl group including a group represented by $HX_2C$— or $H_2XC$—, and the like are exemplified, and the halogenated alkoxy group including a group represented by $HX_2C$— or $H_2XC$— or the group having a halogenated alkoxy group including a group represented by $HX_2C$— or $H_2XC$— is preferred.

As a group having a halogenated alkyl group including a group represented by $HX_2C$— or $H_2XC$—, an aromatic group, such as phenyl group, and naphthyl group, substituted with the halogenated alkyl group including a group represented by $HX_2C$— or $H_2XC$—, a cycloalkyl group, such as cyclopentyl group, and cyclohexyl group, substituted with the halogenated alkyl group including a group represented by $HX_2C$— or $H_2XC$—, and the like are exemplified, and the aromatic group substituted with the halogenated alkyl group including a group represented by $HX_2C$— or $H_2XC$— is preferred.

As a group having a halogenated alkoxy group including a group represented by $HX_2C$— or $H_2XC$—, an aromatic group, such as phenyl group, and naphthyl group, substituted with the halogenated alkoxy group including a group represented by $HX_2C$— or $H_2XC$—, an alkyl group, such as methyl group, ethyl group, n-propyl group, and i-propyl group, substituted with the halogenated alkoxy group including a group represented by $HX_2C$— or $H_2XC$—, a cycloalkyl group, such as cyclopentyl group, and cyclohexyl group, substituted with the halogenated alkoxy group including a group represented by $HX_2C$— or $H_2XC$—, and the like are exemplified, and the aromatic group substituted with the halogenated alkoxy group including a group represented by $HX_2C$— or $H_2XC$—.

A cycloalkyl group, a phenoxyalkyl group that may have a substituent on an aromatic ring, and a phenylthioalkyl group that may have a substituent on an aromatic ring are also preferred as $R^{c5}$. The substituent that the phenoxyalkyl group and phenylthioalkyl group may have is the same as the substituent that the phenyl group included in $R^{c5}$ may have.

Among the monovalent organic groups, an alkyl group, a cycloalkyl group, an optionally substituted phenyl group, a cycloalkylalkyl group, and a phenylthioalkyl group that may have a substituent in the aromatic ring. As the alkyl group, an alkyl group having 1 or more and 20 or less carbon atoms is preferred, an alkyl group having 1 or more and 8 or less carbon atoms is more preferred, an alkyl group having 1 or more and 4 or less carbon atoms is particularly preferred, and a methyl group is most preferred. Among the optionally substituted phenyl groups, a 2-methylphenyl group is preferred. The number of carbon atoms of the cycloalkyl group included in the cycloalkylalkyl group is preferably 5 or more and 10 or less, more preferably 5 or more and 8 or less, and particularly preferably 5 or 6. The number of carbon atoms of the alkyl group included in the cycloalkylalkyl group is preferably 1 or more and 8 or less, more preferably 1 or more and 4 or less, and particularly preferably 2. Among the cycloalkylalkyl groups, a cyclopentylethyl group is preferred. The number of carbon atoms of the alkylene group included in the phenylthioalkyl group that may have a substituent on the aromatic ring is preferably 1 or more and 8 or less, more preferably 1 or more and 4 or less, and particularly preferably 2. Among the phenylthioalkyl groups that may have a substituent on the aromatic ring, a 2-(4-chlorophenylthio)ethyl group is preferred.

In the group represented by the formula (c3), when there is a plurality of $R^{c5}$s and the plurality of $R^{c5}$s bonds to each other to form a ring, examples of the ring formed include a hydrocarbon ring, a heterocyclic ring, and the like. As a heteroatom included in the heterocycle, for example, N, O, and S is exemplified. An aromatic ring is particularly preferred as the ring formed by combining a plurality of $R^{c5}$s each other. Such an aromatic ring may be an aromatic hydrocarbon ring or an aromatic heterocyclic ring. Such an aromatic ring is preferably an aromatic hydrocarbon ring. Specific examples of the group in which a benzene ring is formed by combining a plurality of $R^{c5}$s in the formula (3) each other are shown below.

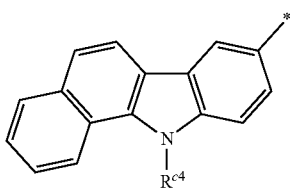

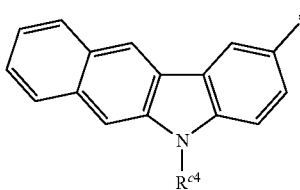

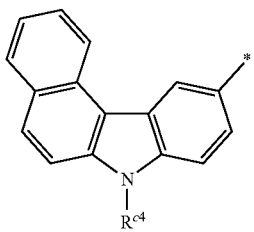

In a group represented by the formula (c4), $R^{c8}$ is a nitro group or a monovalent organic group. $R^{c8}$ bonds to a 6-membered aromatic ring other than an aromatic ring that bonds to a group represented by —(CO)$_{n1}$— on a condensed ring in the formula (c4). In the formula (c4), the bond position of $R^{c8}$ is not particularly limited. When a group represented by the formula (c4) has 1 or more $R^{c8}$s, one of 1 or more $R^{c8}$s preferably bonds to 7-position in a fluorene skeleton from the viewpoint that a compound having the group represented by the formula (c4) can be easily synthesized. In other words, when a group represented by the formula (c4) has 1 or more $R^{c8}$s, the group represented by the formula (c4) is preferably a group represented by the formula (c6). When there is a plurality of $R^{c8}$s, plurality of substituents may be the same or different.

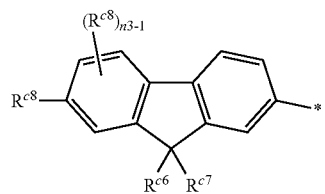

(c6)

In the formula (c6), $R^{c6}$, $R^{c7}$, $R^{c8}$, and n3 are same as $R^{c6}$, $R^{c7}$, $R^{c8}$, and n3 in the formula (c4).

When $R^{c8}$ is a monovalent organic group, $R^{c8}$ is not particularly limited as long as it does not interfere with the object of the present invention. As the organic group, a carbon atom-containing group is preferred, and a group consisting of 1 or more carbon atoms, and 1 or more atoms selected from the group consisting of H, O, S, Se, N, B, P, Si and a halogen atom is more preferred. The number of carbon atoms of the carbon atom-containing group is not particularly limited, and preferably 1 or more and 50 or less, and more preferably 1 or more and 20 or less. Suitable examples of the monovalent organic group as $R^{c8}$ include the same groups as the examples of the monovalent organic group as RCS in the formula (c3).

In the formula (c4), $R^{c6}$ and $R^{c7}$ each represent an optionally substituted chain alkyl group, an optionally substituted chain alkoxy group, an optionally substituted cyclic organic group, or a hydrogen atom. $R^{c6}$ and $R^{c7}$ may be combined to one another to form a ring. Among these, preferably, $R^{c6}$ and $R^{c7}$ are optionally substituted chain alkyl groups. When $R^{c6}$ and $R^{c7}$ are optionally substituted chain alkyl groups, a chain alkyl group may be either a straight-chain alkyl group or a branched-chain alkyl group.

When $R^{c6}$ and $R^{c7}$ are chain alkyl groups having no substituent, the number of carbon atoms of the chain alkyl group is preferably 1 or more and 20 or less, more preferably 1 or more and 10 or less, and particularly preferably 1 or more and 6 or less. When $R^{c6}$ and $R^{c7}$ are chain alkyl groups, specific examples thereof include a methyl group, an ethyl group, an n-propyl group, an isopropyl group, an n-butyl group, an isobutyl group, a sec-butyl group, a tert-butyl group, an n-pentyl group, an isopentyl group, a sec-pentyl group, a tert-pentyl group, an n-hexyl group, an n-heptyl group, an n-octyl group, an isooctyl group, a sec-octyl group, a tert-octyl group, an n-nonyl group, an isononyl group, an n-decyl group, an isodecyl group, and the like. When $R^{c6}$ and $R^{c7}$ are alkyl groups, the alkyl group may have an ether bond (—O—) in a carbon chain. Examples of the alkyl group having an ether bond in a carbon chain include a methoxyethyl group, an ethoxyethyl group, a methoxyethoxyethyl group, an ethoxyethoxyethyl group, a propyloxyethoxyethyl group, and a methoxypropyl group.

When $R^{c6}$ and $R^{c7}$ are chain alkyl groups having a substituent, the number of carbon atoms of the chain alkyl group is preferably 1 or more and 20 or less, more preferably 1 or more and 10 or less, and particularly preferably 1 or more and 6 or less. In this case, the number of carbon atoms of the substituent is not included in the number of carbon atoms of the chain alkyl group. The chain alkyl group having a substituent is preferably a straight-chain group.

The substituent, with which the alkyl group is optionally substituted, is not particularly limited as long as it does not interfere with the object of the present invention. Suitable examples of the substituent include an alkoxy group, a cyano group, a halogen atom, a halogenated alkyl group, a cyclic organic group, and an alkoxycarbonyl group. Examples of the halogen atom include a fluorine atom, a chlorine atom, a bromine atom, and an iodine atom. Among these, a fluorine atom, a chlorine atom, and a bromine atom are preferable. Examples of the cyclic organic group include a cycloalkyl group, an aromatic hydrocarbon group, and a heterocyclyl group. Specific examples of the cycloalkyl group are the same as suitable examples in case $R^{c8}$ is a cycloalkyl group. Specific examples of the aromatic hydrocarbon group include a phenyl group, a naphthyl group, a biphenylyl group, an anthryl group, a phenanthryl group, and the like. Specific examples of the heterocyclyl group are the same as suitable examples in case $R^{c8}$ is a heterocyclyl group. When $R^{c8}$ is an alkoxycarbonyl group, an alkoxy group included in the alkoxycarbonyl group may be straight or branched, and preferably straight. The number of carbon atoms of an alkoxy group included in the alkoxycarbonyl group is preferably 1 or more and 10 or less, and more preferably 1 or more and 6 or less.

When the chain alkyl group has a substituent, the number of substituents is not particularly limited. The number of substituents preferably varies depending on the number of carbon atoms of the chain alkyl group. The number of substituents is typically 1 or more and 20 or less, preferably 1 or more and 10 or less, and more preferably 1 or more and 6 or less.

When $R^{c6}$ and $R^{c7}$ are unsubstituted chain alkoxy groups, the number of carbon atoms of the chain alkoxy group is preferably 1 or more and 20 or less, more preferably 1 or more and 10 or less, and particularly preferably 1 or more and 6 or less. When $R^{c6}$ and $R^{c7}$ are chain alkoxy groups, specific examples thereof include a methoxy group, an ethoxy group, an n-propyloxy group, an isopropyloxy group, an n-butyloxy group, an isobutyloxy group, a sec-butyloxy group, a tert-butyloxy group, an n-pentyloxy group, an isopentyloxy group, a sec-pentyloxy group, a tert-pentyloxy group, an n-hexyloxy group, an n-heptyloxy group, an n-octyloxy group, an isooctyloxy group, a sec-octyloxy group, a tert-octyloxy group, an n-nonyloxy group, an isononyloxy group, an n-decyloxy group, an isodecyloxy group, and the like. When $R^{c6}$ and $R^{c7}$ are alkoxy groups, the alkoxy group may contain an ether bond (—O—) in the carbon chain. Examples of the alkoxy group having an ether bond in the carbon chain include a methoxyethoxy group, an ethoxyethoxy group, a methoxyethoxyethoxy group, an ethoxyethoxyethoxy group, a propyloxyethoxyethoxy group, a methoxypropyloxy group, and the like.

When $R^{c6}$ and $R^{c7}$ are chain alkoxy groups having a substituent, the substituent that the alkoxy group may have is the same as the substituent that the chain alkyl group as $R^{c6}$ and $R^{c7}$ may have.

When $R^{c6}$ and $R^{c7}$ are cyclic organic groups, the cyclic organic groups may be an alicyclic group or an aromatic group. Examples of the cyclic organic group include an aliphatic cyclic hydrocarbon group, an aromatic hydrocarbon group, and a heterocyclyl group. When $R^{c6}$ and $R^{c7}$ are cyclic organic groups, the substituent, with which the cyclic organic group is optionally substituted, is the same as in the case where $R^{c6}$ and $R^{c7}$ are chain alkyl groups.

When $R^{c6}$ and $R^{c7}$ are aromatic hydrocarbon groups, the aromatic hydrocarbon group is preferably a phenyl group, or a group formed by bonding a plurality of benzene rings through a carbon-carbon bond, or a group formed by condensing a plurality of benzene rings. When the aromatic hydrocarbon group is a phenyl group, or a group formed by bonding or condensing a plurality of benzene rings, the number of benzene rings included in the aromatic hydrocarbon group is not particularly limited, and is preferably 3 or less, more preferably 2 or less, and particularly preferably 1. Preferred specific examples of the aromatic hydrocarbon group include a phenyl group, a naphthyl group, a biphenylyl group, an anthryl group, and a phenanthryl group.

When $R^{c6}$ and $R^{c7}$ are aliphatic cyclic hydrocarbon groups, the aliphatic cyclic hydrocarbon group may be a monocyclic or polycyclic group. The number of carbon atoms of the aliphatic cyclic hydrocarbon group is not particularly limited, and is preferably 3 or more and 20 or less, and more preferably 3 or more and 10 or less. Examples of the monocyclic cyclic hydrocarbon group include cyclopropyl group, a cyclobutyl group, a cyclopentyl group, a cyclohexyl group, a cycloheptyl group, a cyclooctyl group, a norbornyl group, an isobornyl group, a tricyclononyl group, a tricyclodecyl group, a tetracyclododecyl group, and an adamantyl group.

When $R^{c6}$ and $R^{c7}$ are heterocyclyl groups, the same groups as the heterocyclyl groups as RCS in the formula (c3) are exemplified.

$R^{c6}$ and $R^{c7}$ may be combined to one another to form a ring. The group composed of the ring formed by $R^{c6}$ and $R^{c7}$ is preferably a cycloalkylidene group. When $R^{c6}$ and $R^{c7}$ are combined to form a cycloalkylidene group, the ring constituting the cycloalkylidene group is preferably a 5- to 6-membered ring, and more preferably a 5-membered ring.

When $R^{c7}$ and a benzene ring in fluorene skeleton are combined to form a ring, the ring may be an aromatic ring or an aliphatic ring.

When the group formed by combining $R^{c6}$ and $R^{c7}$ is a cycloalkylidene group, the cycloalkylidene group may be condensed with one or more other rings. Examples of the ring which may be condensed with the cycloalkylidene group include a benzene ring, a naphthalene ring, a cyclobutane ring, a cyclopentane ring, a cyclohexane ring, a cycloheptane ring, a cyclooctane ring, a furan ring, a thiophene ring, a pyrrole ring, a pyridine ring, a pyrazine ring, a pyrimidine ring, and the like.

Examples of a suitable group among $R^{c6}$ and $R^{c7}$ described above include a group represented by the formula: -$A^1$-$A^2$. In the formula, $A^1$ is a linear alkylene group, and $A^2$ is an alkoxy group, a cyano group, a halogen atom, a halogenated alkyl group, a cyclic organic group, or an alkoxycarbonyl group.

The number of carbon atoms of the linear alkylene group for $A^1$ is preferably 1 or more and 10 or less, and more preferably 1 or more and 6 or less. When $A^2$ is an alkoxy group, the alkoxy group may be a linear or branched alkoxy group, and preferably a linear alkoxy group. The number of carbon atoms of the alkoxy group is preferably 1 or more and 10 or less, and more preferably 1 or more and 6 or less. When $A^2$ is a halogen atom, a fluorine atom, a chlorine atom, a bromine atom, or an iodine atom is preferable, and a fluorine atom, a chlorine atom, or a bromine atom is more preferable. When $A^2$ is a halogenated alkyl group, a halogen atom included in the halogenated alkyl group is preferably a fluorine atom, a chlorine atom, a bromine atom, or an iodine atom, and more preferably is a fluorine atom, a chlorine atom, or a bromine atom. The halogenated alkyl group may be a linear or branched halogenated alkyl group, preferably a linear halogenated alkyl group. When $A^2$ is a cyclic organic group, examples of the cyclic organic group are the same as the cyclic organic group possessed by $R^{c6}$ and $R^{c7}$ as a substituent. When $A^2$ is an alkoxycarbonyl group, examples of the alkoxycarbonyl group are the same as the alkoxycarbonyl group possessed by $R^{c6}$ and $R^{c7}$ as a substituent.

Suitable specific examples of $R^{c6}$ and $R^{c7}$ include alkyl groups such as an ethyl group, an n-propyl group, an n-butyl group, an n-hexyl group, an n-heptyl group, and an n-octyl group; alkoxyalkyl groups such as a 2-methoxyethyl group, a 3-methoxy-n-propyl group, a 4-methoxy-n-butyl group, a 5-methoxy-n-pentyl group, a 6-methoxy-n-hexyl group, a 7-methoxy-n-heptyl group, a 8-methoxy-n-octyl group, a 2-ethoxyethyl group, a 3-ethoxy-n-propyl group, a 4-ethoxy-n-butyl group, a 5-ethoxy-n-pentyl group, a 6-ethoxy-n-hexyl group, a 7-ethoxy-n-heptyl group, and a 8-ethoxy-n-octyl group; cyanoalkyl groups such as a 2-cyanoethyl group, a 3-cyano-n-propyl group, a 4-cyano-n-butyl group, a 5-cyano-n-pentyl group, a 6-cyano-hexyl group, a 7-cyano-n-heptyl group, and a 8-cyano-n-octyl group; phenylalkyl groups such as a 2-phenylethyl group, a 3-phenyl-n-propyl group, a 4-phenyl-n-butyl group, a 5-phenyl-n-pentyl group, a 6-phenyl-n-hexyl group, a 7-phenyl-n-heptyl group, and a 8-phenyl-n-octyl group; cycloalkylalkyl groups such as a 2-cyclohexylethyl group, a 3-cyclohexyl-n-propyl group, a 4-cyclohexyl-n-butyl group, a 5-cyclohexyl-n-pentyl group, a 6-cyclohexyl-n-hexyl group, a 7-cyclohexyl-n-heptyl group, a 8-cyclohexyl-n-octyl group, a 2-cyclopentylethyl group, a 3-cyclopentyl-n-propyl group, a 4-cyclopentyl-n-butyl group, a 5-cyclopentyl-n-pentyl group, a 6-cyclopentyl-n-hexyl group, a 7-cyclopentyl-n-heptyl group, and a 8-cyclopentyl-n-octyl group; alkoxycarbonylalkyl groups such as a 2-methoxycarbonylethyl group, a 3-methoxycarbonyl-n-propyl group, a 4-methoxycarbonyl-n-butyl group, a 5-methoxycarbonyl-n-pentyl group, a 6-methoxycarbonyl-n-hexyl group, a 7-methoxycarbonyl-n-heptyl group, a 8-methoxycarbonyl-n-octyl group, a 2-ethoxycarbonylethyl group, a 3-ethoxycarbonyl-n-propyl group, a 4-ethoxycarbonyl-n-butyl group, a 5-ethoxycarbonyl-n-pentyl group, a 6-ethoxycarbonyl-n-hexyl group, a 7-ethoxycarbonyl-n-heptyl group, and a 8-ethoxycarbonyl-n-octyl group; and halogenated alkyl groups such as a 2-chloroethyl group, a 3-chloro-n-propyl group, a 4-chloro-n-butyl group, a 5-chloro-n-pentyl group, a 6-chloro-n-hexyl group, a 7-chloro-n-heptyl group, a 8-chloro-n-octyl group, a 2-bromoethyl group, a 3-bromo-n-propyl group, a 4-bromo-n-butyl group, a 5-bromo-n-pentyl group, a 6-bromo-n-hexyl group, a 7-bromo-n-heptyl group, a 8-bromo-n-octyl group, a 3,3,3-trifluoropropyl group, and a 3,3,4,4,5,5,5-heptafluoro-n-pentyl group.

Among groups mentioned above, groups suitable as $R^{c6}$ and $R^{c7}$ are an ethyl group, an n-propyl group, an n-butyl group, an n-pentyl group, a 2-methoxyethyl group, a 2-cyanoethyl group, a 2-phenylethyl group, a 2-cyclohexylethyl group, a 2-methoxycarbonylethyl group, a 2-chloroethyl group, a 2-bromoethyl group, a 3,3,3-trifluoropropyl group, and a 3,3,4,4,5,5,5-heptafluoro-n-pentyl group.

From the view point that a highly sensitive photo polymerization initiator is likely to be easily obtained, A is preferably S.

In the formula (c5), $R^{c9}$ is a monovalent organic group, a halogen atom, a nitro group, or a cyano group. When $R^{c9}$ in the formula (c5) is a monovalent organic group, $R^{c9}$ can be selected from various organic groups as long as it does not interfere with the object of the present invention. As the organic group, a carbon atom-containing group is preferred, and a group consisting of 1 or more carbon atoms, and 1 or more atoms selected from the group consisting of H, O, S, Se, N, B, P, Si and a halogen atom is more preferred. The number of carbon atoms of the carbon atom-containing group is not particularly limited, and preferably 1 or more and 50 or less, and more preferably 1 or more and 20 or less.

Suitable examples of the organic group as $R^{c9}$ in the formula (c5) are the same groups as the monovalent organic groups as $R^cS$ in the formula (c3).

Among $R^{c9}$, a benzoyl group; a naphthoyl group; a benzoyl groups substituted with a group selected from the group consisting of an alkyl group having 1 or more and 6 or less carbon atoms, a morpholin-1-yl group, a piperazin-1-yl group, and a phenyl group; a nitro group; an optionally substituted benzofuranylcarbonyl group are preferred, and a benzoyl group; a naphthoyl group; a 2-methylphenylcarbonyl group; a 4-(piperazine-1-yl)phenylcarbonyl group; and a 4-(phenyl)phenylcarbonyl group are more preferred.

In the formula (c5), n4 is preferably an integer of 0 or more and 3 or less, more preferably an integer of 0 or more and 2 or less, and particularly preferably 0 or 1. When n4 is 1, the position at which $R^{c9}$ bonds is preferably the para-position to the bonding through which the phenyl group (to which $R^{c9}$ bonds) bonds to an oxygen atom or a sulfur atom.

In the formula (c1) and the formula (c2), the monovalent organic group as $R^{c2}$ is not particularly limited as long as it does not interfere with the object of the present invention. As the organic group, a carbon atom-containing group is preferred, and a group consisting of 1 or more carbon atoms, and 1 or more atoms selected from the group consisting of H, O, S, Se, N, B, P, Si and a halogen atom is more preferred. The number of carbon atoms of the carbon atom-containing group is not particularly limited, and preferably 1 or more and 50 or less, and more preferably 1 or more and 20 or less. Suitable examples of the monovalent organic group as $R^{c2}$ are the same groups as the monovalent organic groups as $R^cS$ in the formula (c3). Specific examples of these groups are the same as the groups described for $R^cS$ in the formula (c3). A cycloalkyl group, a phenoxyalkyl group that may have a substituent on an aromatic ring, and a phenylthioalkyl group that may have a substituent on an aromatic ring are also preferred as $R^{c2}$. The substituent that the phenoxyalkyl group and phenylthioalkyl group may have is the same as the substituent that the phenyl group, the naphthyl group, and the heterocyclyl group included in $R^cS$ in the formula (c3) may have.

Among substituents, a substituent including the group represented by $HX_2C$— or $H_2XC$— described above, an alkyl group, a cycloalkyl group, an optionally substituted phenyl group, an optionally substituted cycloalkyl group, and a phenylthioalkyl group that may have a substituent on an aromatic ring are preferred. The alkyl group, the optionally substituted alkyl group, the number of carbon atoms of the cycloalkyl group included in the cycloalkylalkyl group, the cycloalkylalkyl group, the number of carbon atoms of the alkylene group included in the phenylthioalkyl group that may have a substituent on an aromatic ring, and the phenylthioalkyl group that may have a substituent on an aromatic ring are the same as these about $R^cS$.

A group represented by $-A^3-CO-O-A^4$ is also preferred as $R^{c2}$. $A^3$ is a divalent organic group, preferably a divalent hydrocarbon group, and more preferably an alkylene group. $A^4$ is a monovalent organic group, and preferably a monovalent hydrocarbon group.

When $A^3$ is the alkylene group, the alkylene group may be straight or branched, and is preferably straight. When $A^3$ is the alkylene group, the number of carbon atoms of the alkylene group is preferably 1 or more and 10 or less, more preferably 1 or more and 6 or less, and particularly preferably 1 or more and 4 or less.

Suitable examples of $A^4$ include an alkyl group having 1 or more and 10 or less carbon atoms, an aralkyl group having 7 or more and 20 or less carbon atoms, and an aromatic hydrocarbon group having 6 or more and 20 or less carbon atoms. Suitable specific examples of $A^4$ include a methyl group, an ethyl group, an n-propyl group, an isopropyl group, an n-butyl group, an isobutyl group, a sec-butyl group, a tert-butyl group, an n-pentyl group, an n-hexyl group, a phenyl group, a naphthyl group, a benzyl group, a phenethyl group, an α-naphthylmethyl group, a β-naphthylmethyl group, and the like.

Specific examples of a suitable group represented by -$A^3$-CO—O-$A^4$ include a 2-methoxycarbonylethyl group, a 2-ethoxycarbonylethyl group, a 2-n-propyloxycarbonylethyl group, a 2-n-butyloxycarbonylethyl group, a 2-n-pentyloxycarbonylethyl group, a 2-n-hexyloxycarbonylethyl group, a 2-benzyloxycarbonylethyl group, a 2-phenoxycarbonylethyl group, a 3-methoxycarbonyl-n-propyl group, a 3-ethoxycarbonyl-n-propyl group, a 3-n-propyloxycarbonyl-n-propyl group, a 3-n-butyloxycarbonyl-n-propyl group, a 3-n-pentyloxycarbonyl-n-propyl group, a 3-n-hexyloxycarbonyl-n-propyl group, a 3-benzyloxycarbonyl-n-propyl group, a 3-phenoxycarbonyl-n-propyl group, and the like.

A group represented by the following formula (c7) or the following formula (c8) is also preferred as $R^{c2}$.

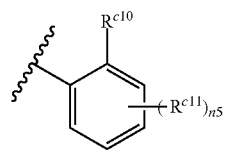

(c7)

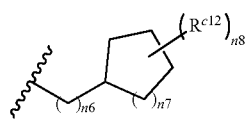

(c8)

In the formula (c7) and the formula (c8), $R^{c10}$ and $R^{c11}$ are each independently a monovalent organic group, n5 is an integer of 0 or more and 4 or less, when $R^{c10}$ and $R^{c11}$ are adjacent to each other on the benzene ring, $R^{c10}$ and $R^{c11}$ may be combined to each other to form a ring, $R^{c12}$ is a monovalent organic group, n6 is an integer of 1 or more and 8 or less, n7 is an integer of 1 or more and 5 or less, and n8 is an integer of 0 or more and (n7+3) or less.

The organic group as $R^{c10}$ and $R^{c11}$ in the formula (c7) is the same ad $R^{c8}$ in the formula (c4). As $R^{c10}$, a halogenated alkoxy group including a group represented by $HX_2C$— or $H_2XC$—, a halogenated alkyl group including a group represented by $HX_2C$- or $H_2XC$—, an alkyl group, or a phenyl group is preferred. When $R^{c10}$ and $R^{c11}$ are combined to each other to form a ring, the ring may be an aromatic ring or an aliphatic ring. Suitable examples of the group represented by the formula (d7) in which $R^{c10}$ and $R^{c11}$ form a ring include a naphthalen-1-yl group, a 1,2,3,4-tetrahydronaphthalen-5-yl group, and the like. In the above formula (c7), n5 is an integer of 0 or more and 4 or less, preferably 0 or 1, and more preferably 0.

In the above formula (c8), $R^{c12}$ is an organic group. As the organic group, the same group as the organic group described above as $R^{c8}$ in the formula (c4). Among the organic groups, an alkyl group is preferred. The alkyl group may be straight or branched. The number of carbon atoms of the alkyl group is preferably 1 or more and 10 or less, more preferably 1 or more and 5 or less, and particularly preferably 1 or more and 3 or less. A methyl group, an ethyl group, a propyl group, an isopropyl group, a butyl group, and the like are exemplified as $R^{c12}$. Among these, the methyl group is preferred.

In the above formula (c8), n7 is an integer of 1 or more and 5 or less, preferably an integer of 1 or more and 3 or less, and more preferably 1 or 2. In the above formula (c8), n8 is 0 or more and (n+3) or less, preferably an integer of 0 or more and 3 or less, more preferably integer of 0 or more and 2 or less, and particularly preferably 0. In the above formula (c8), n6 is an integer of 1 or more and 8 or less, preferably an integer of 1 or more and 5 or less carbon atoms, further preferably an integer of 1 or more and 3 or less, and particularly preferably 1 or 2.

In the formula (c2), $R^{c3}$ is a hydrogen atom, an optionally substituted aliphatic hydrocarbon group having 1 or more and 20 or less carbon atoms, or an optionally substituted aryl group. For $R^{c3}$, suitable examples of the aliphatic hydrocarbon group include a phenyl group, a naphthyl group and the like.

In the formula (c1) and (c2), suitable examples of $R^{c3}$ include a hydrogen atom, a methyl group, an ethyl group, an n-propyl group, an isopropyl group, an n-butyl group, a 2-cyclopentylethyl group, a 2-cyclobutylethyl group, a cyclohexylmethyl group, a phenyl group, a benzyl group, a methylphenyl group, a naphthyl group, and the like. Among these, the methyl group or the phenyl group is more preferred.

Preferable specific examples of the compound represented by the formula (c2) and having the group represented by the formula (c3) include following compounds.

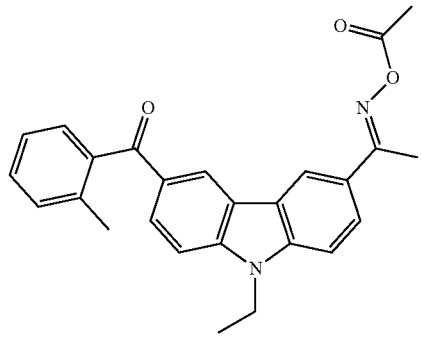

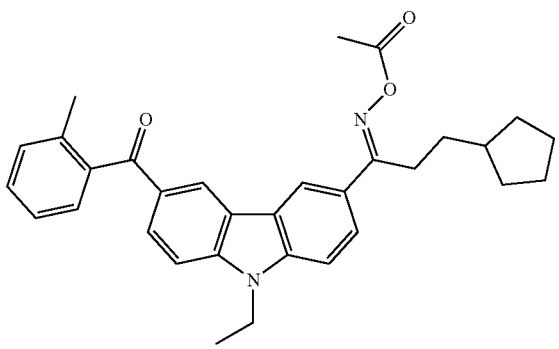

-continued
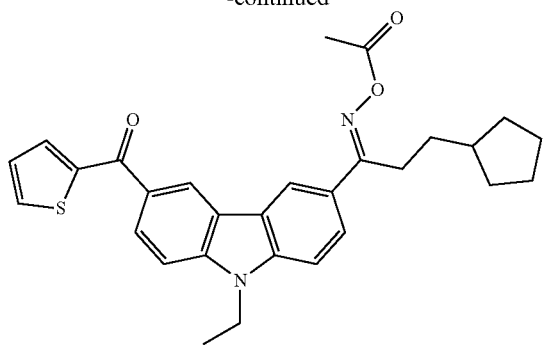
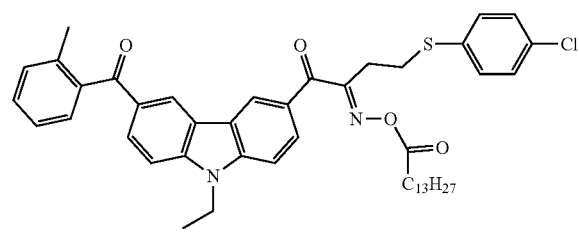
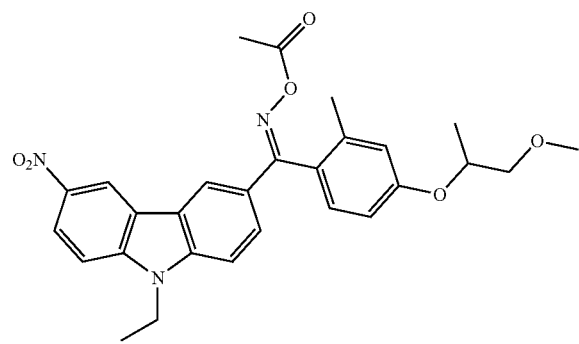
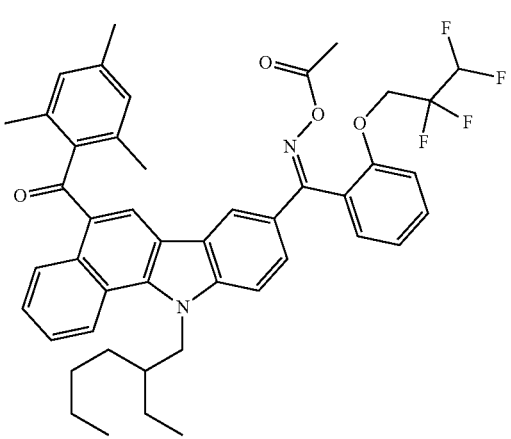
-continued
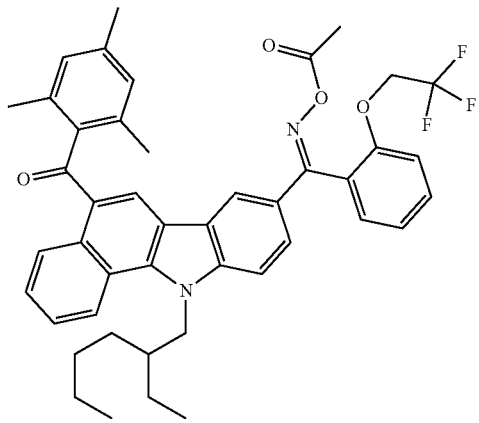
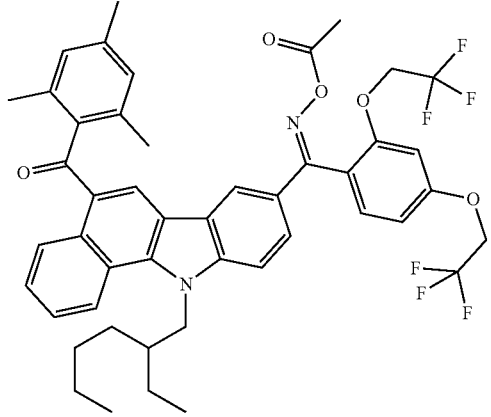
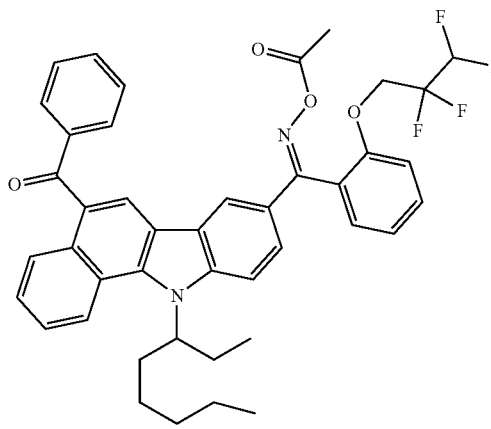
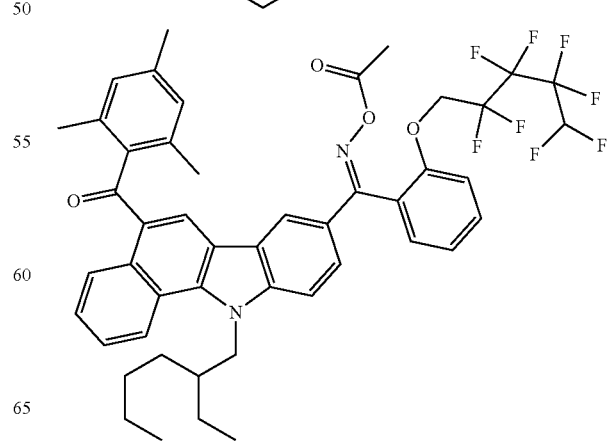

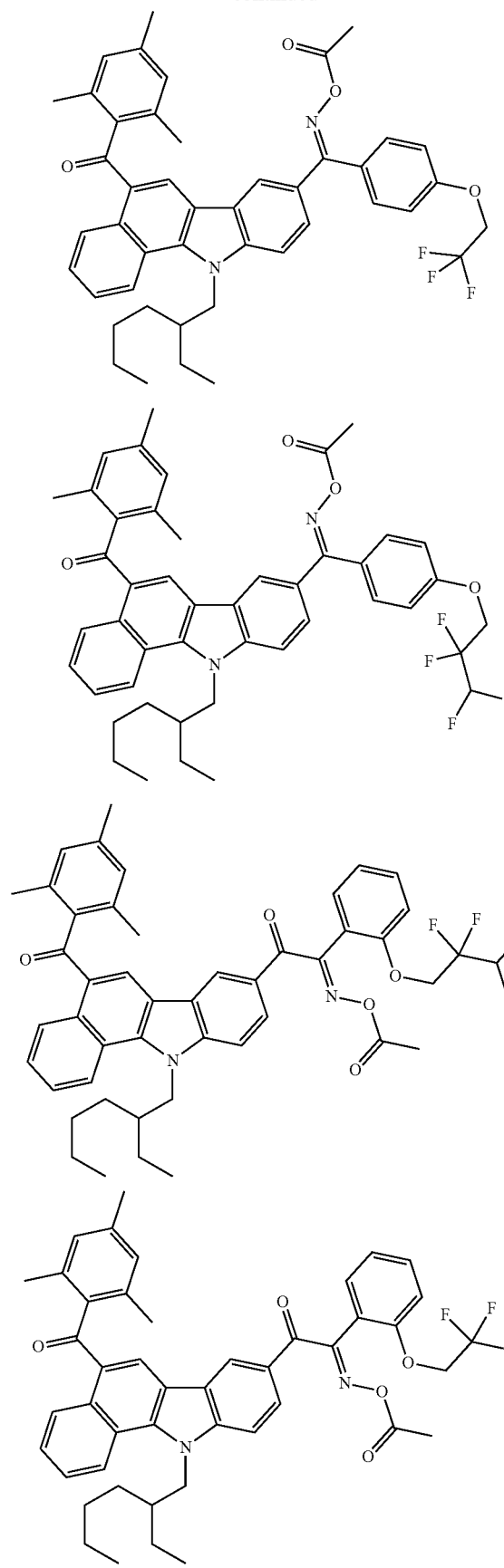
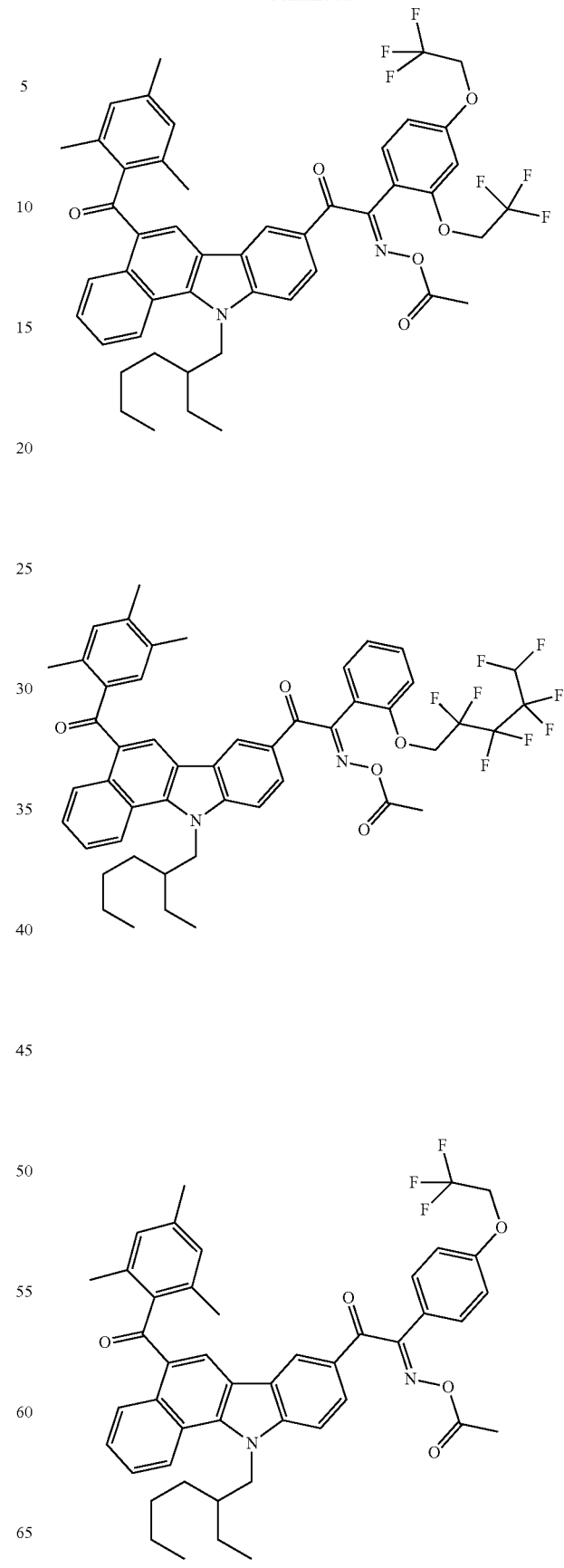

65
-continued
66
-continued
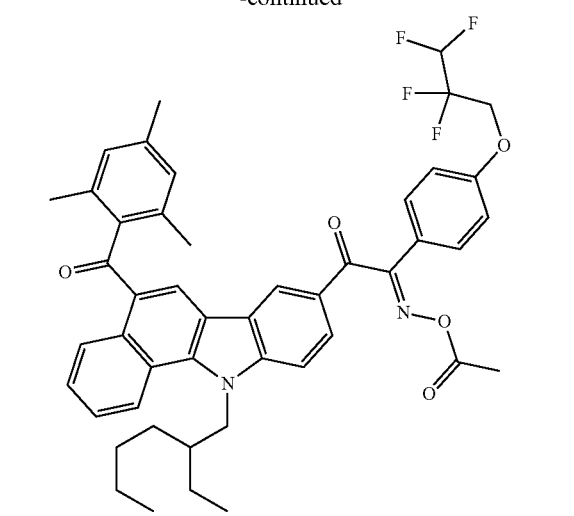
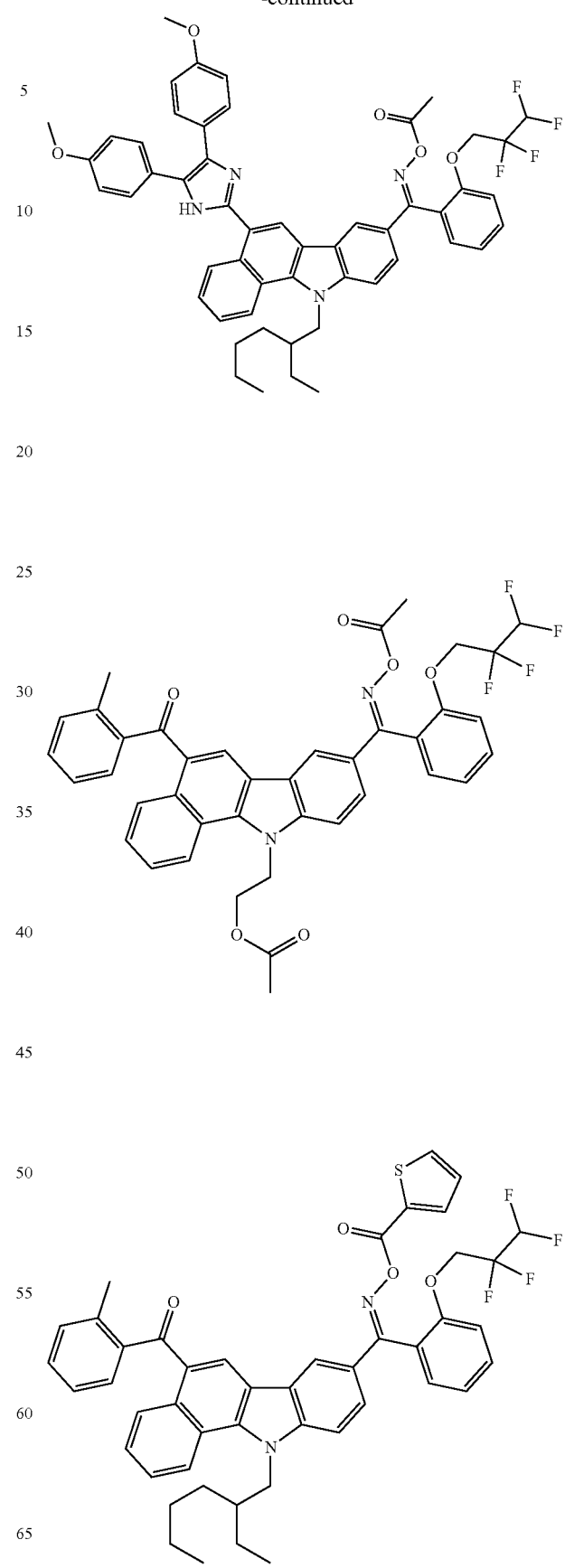

-continued
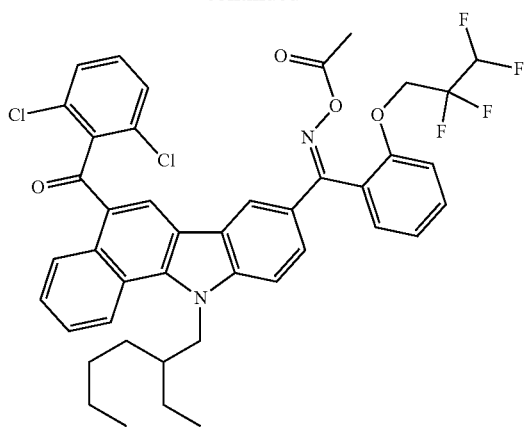
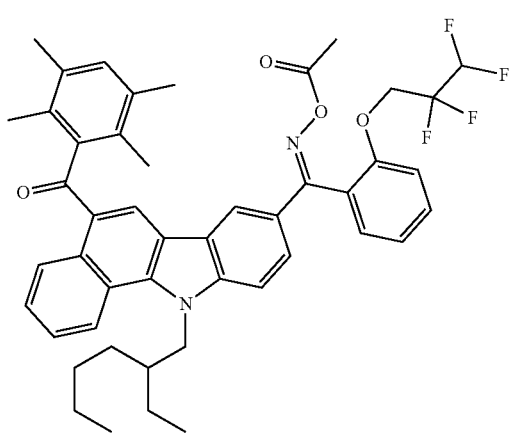
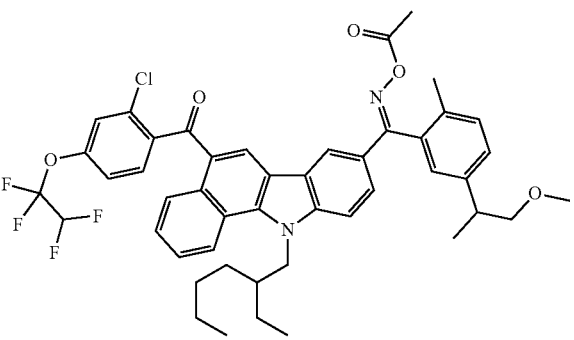
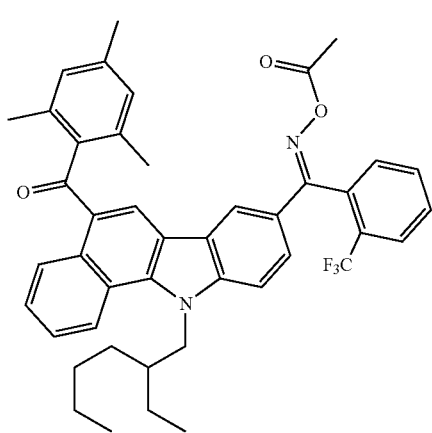
-continued
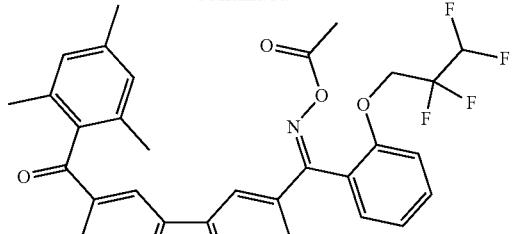
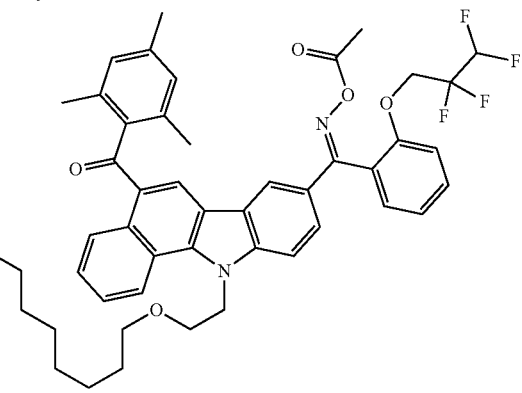
Preferable specific examples of the compound represented by the formula (c2) and having the group represented by the formula (c4) include following compounds.
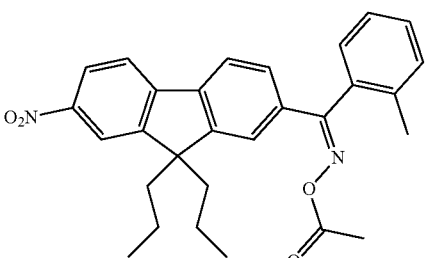
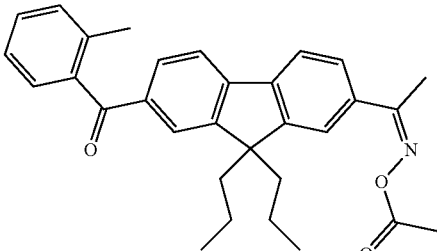
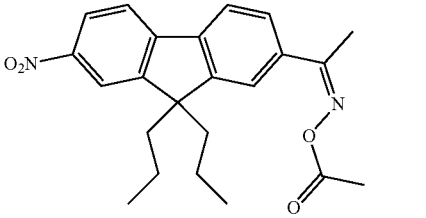

69
-continued
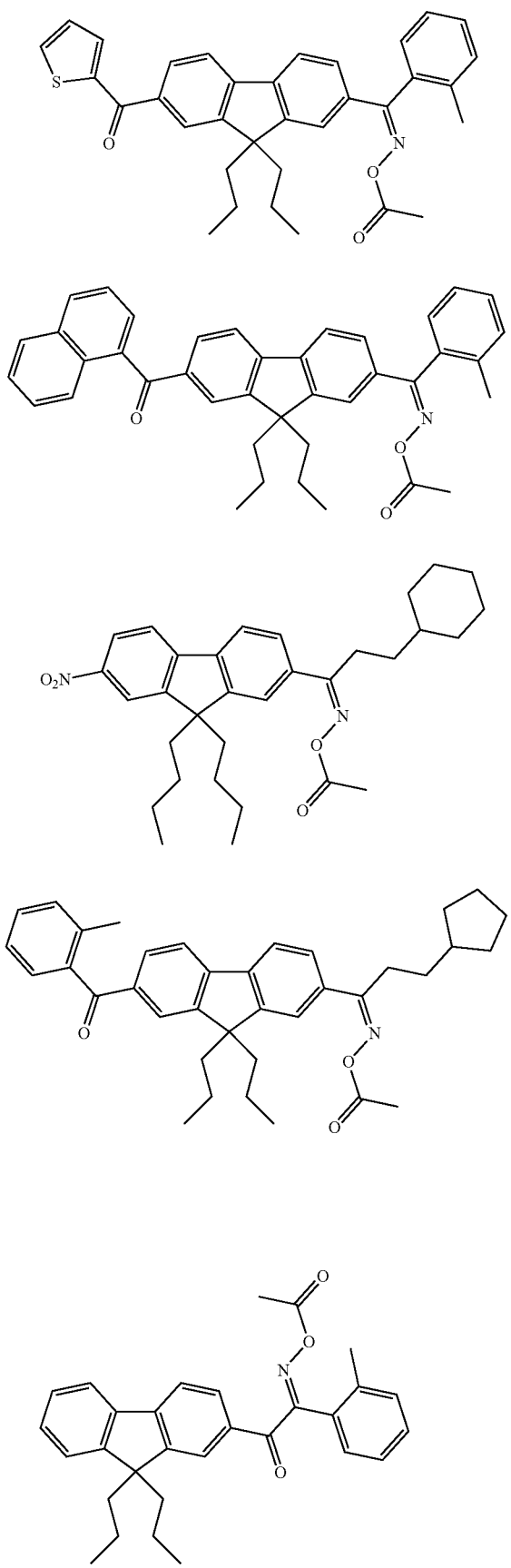
70
-continued
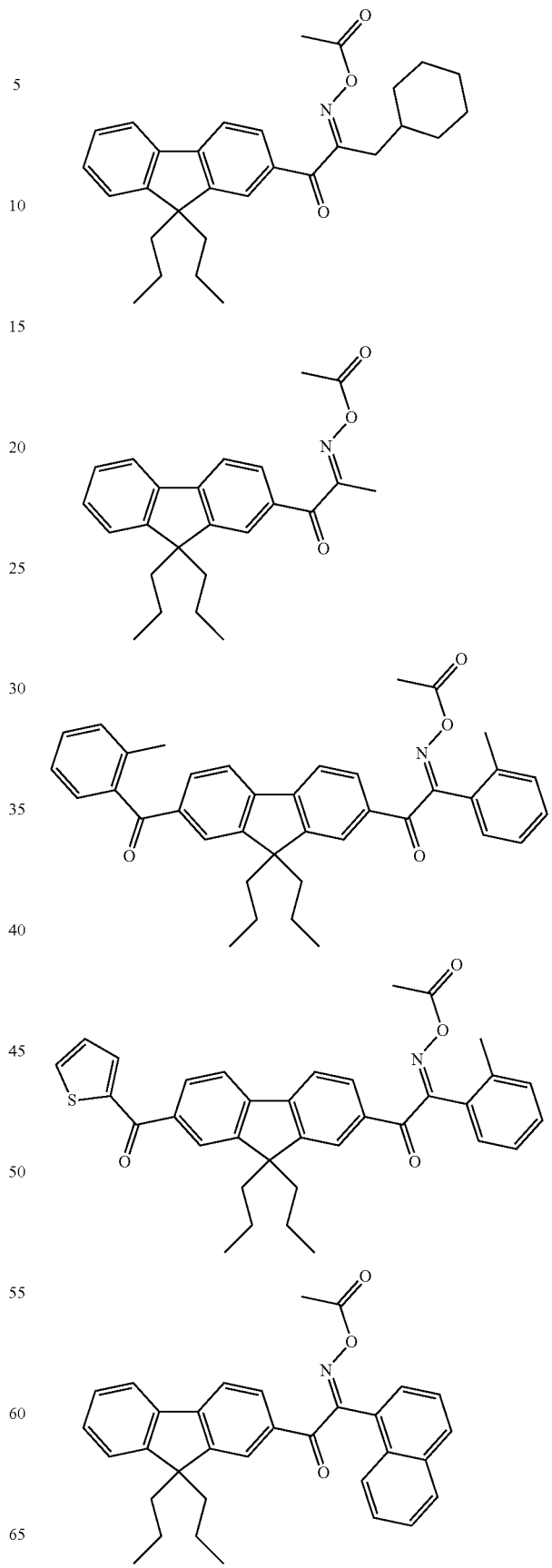

71
-continued
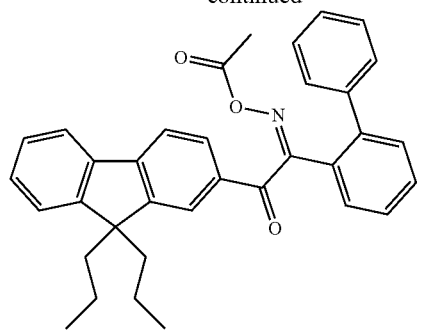
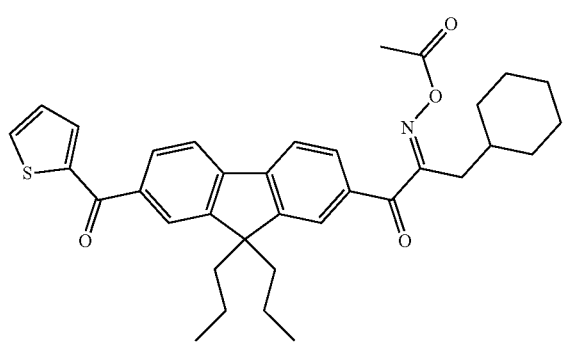
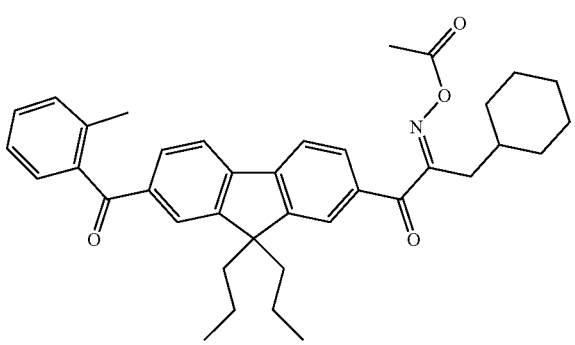
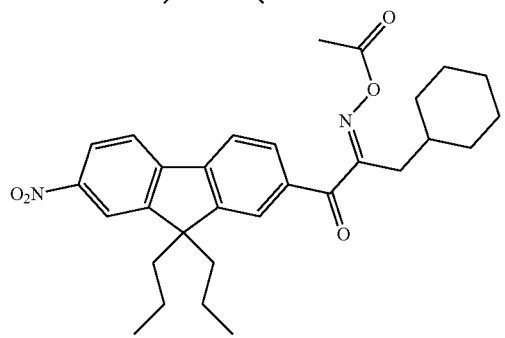
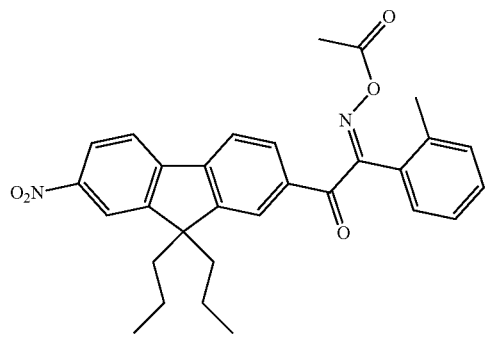
72
-continued
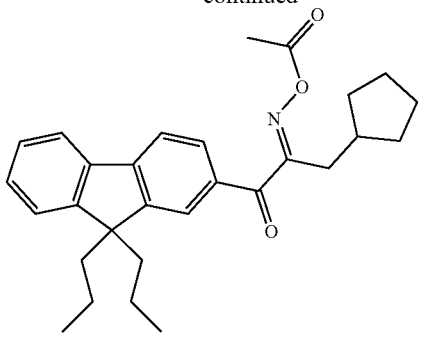
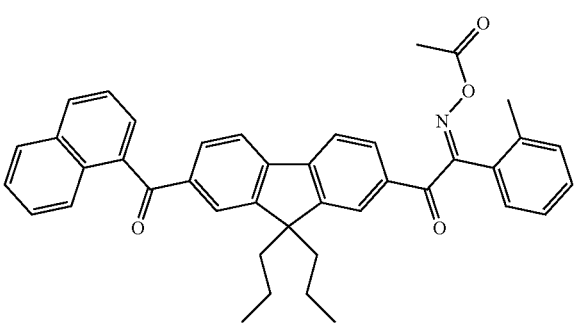
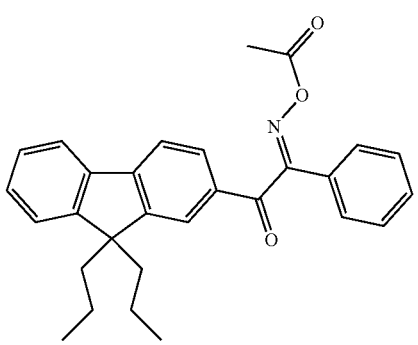
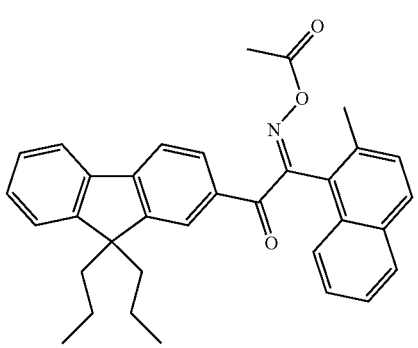
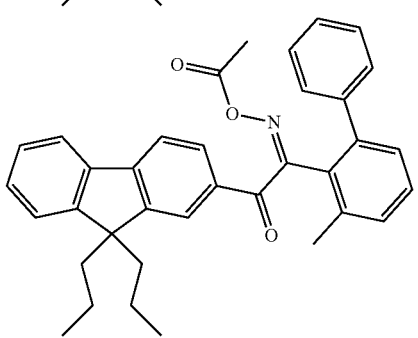

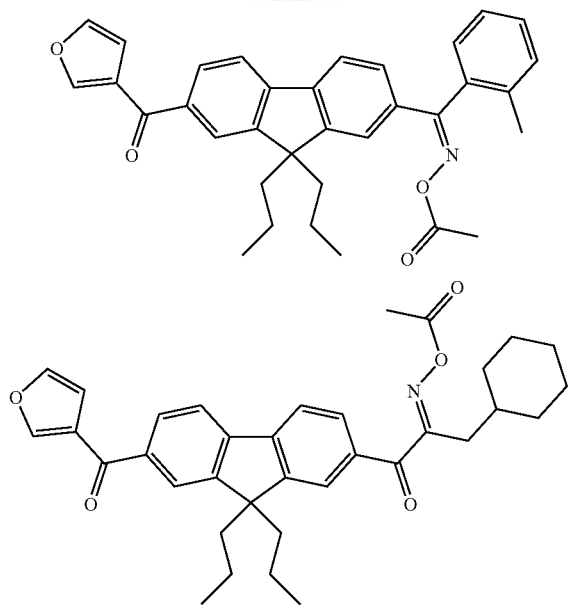
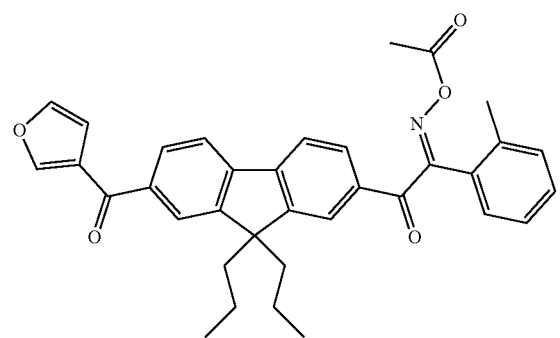
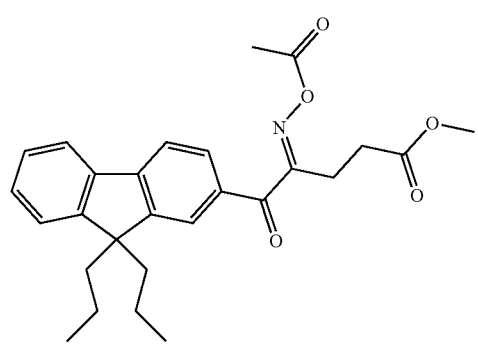
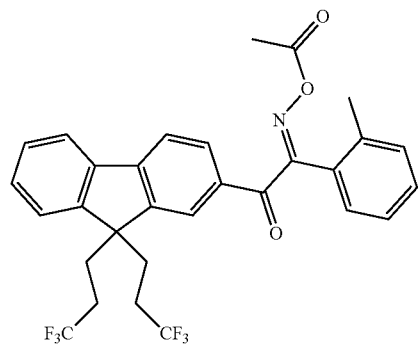
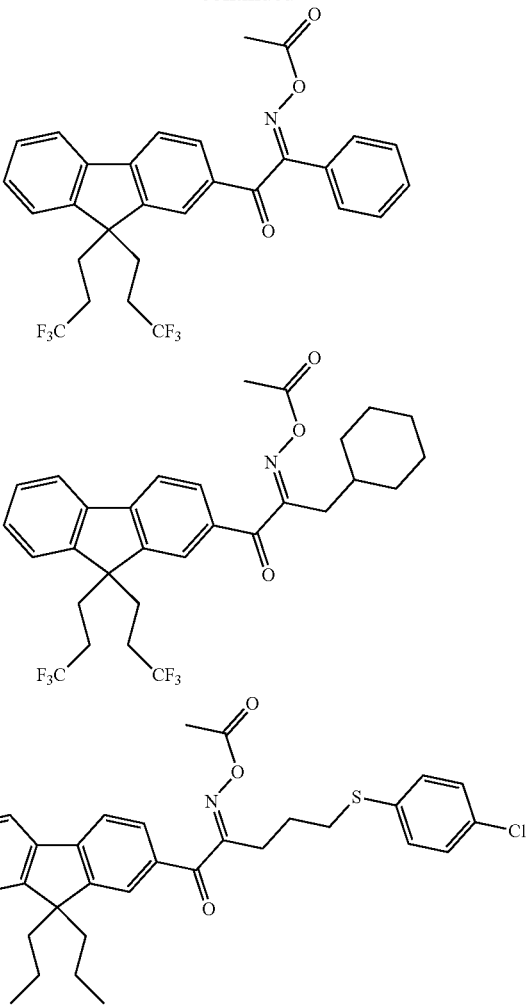
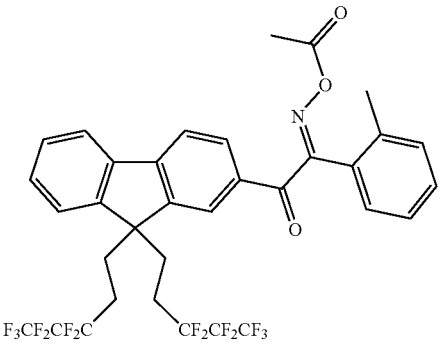
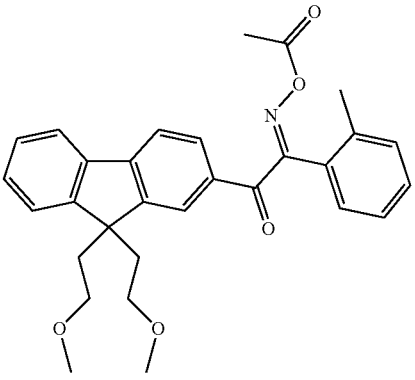

75
-continued
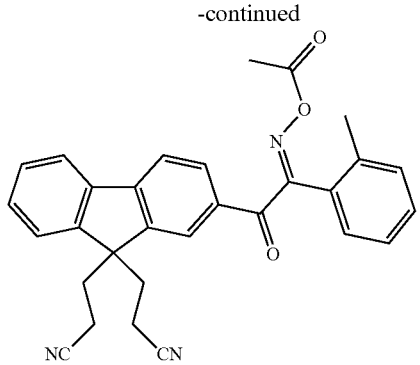
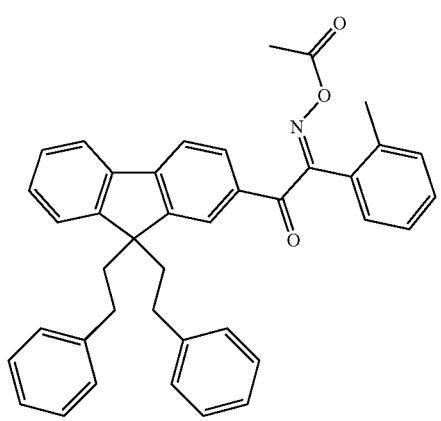
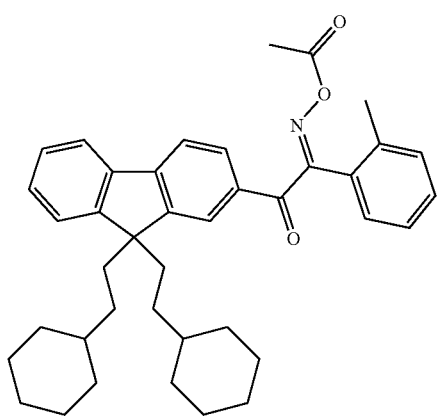
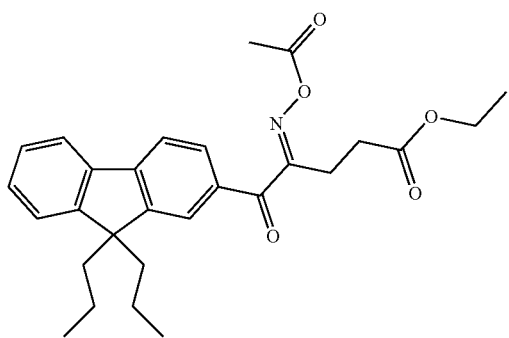
76
-continued
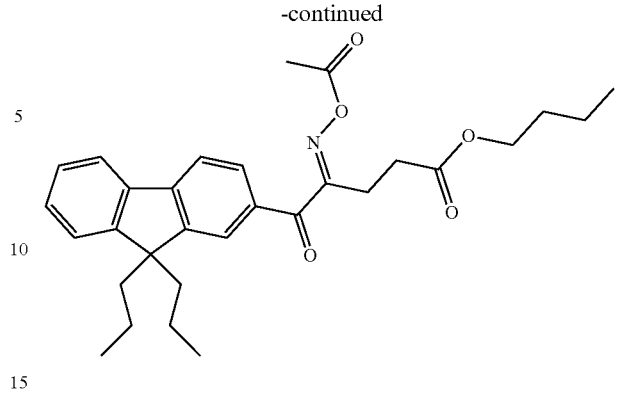
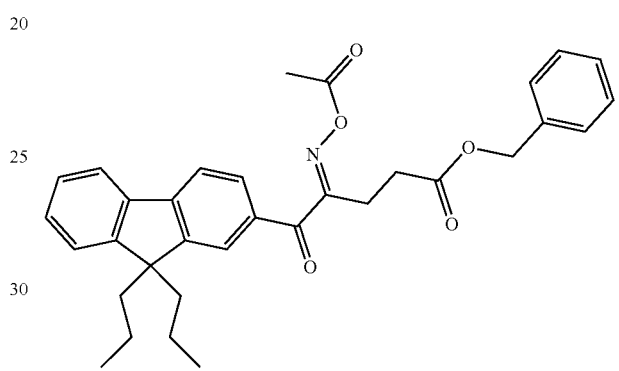
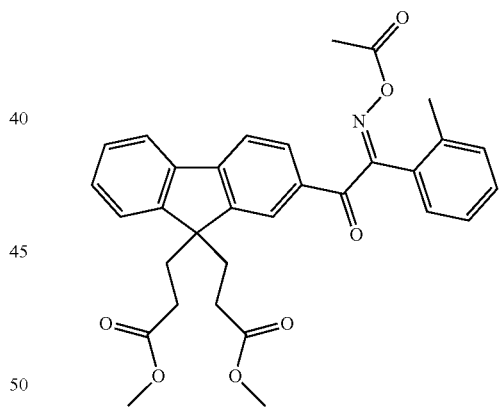
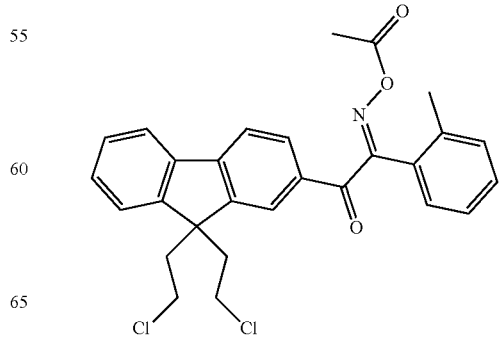

77
-continued
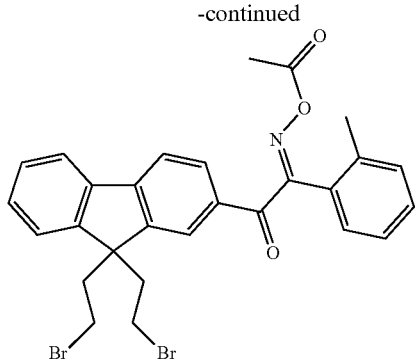
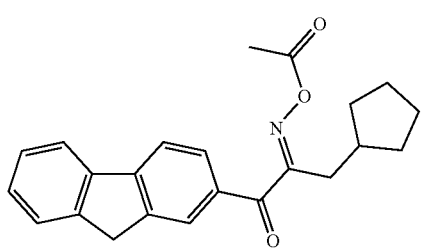
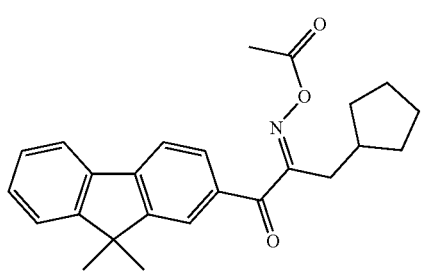
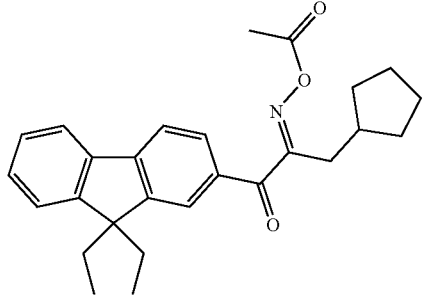
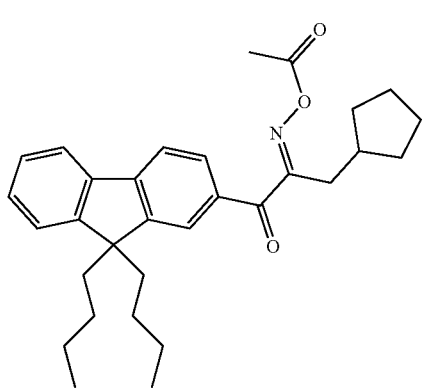
78
-continued
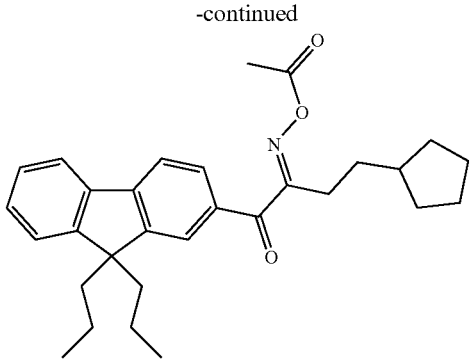
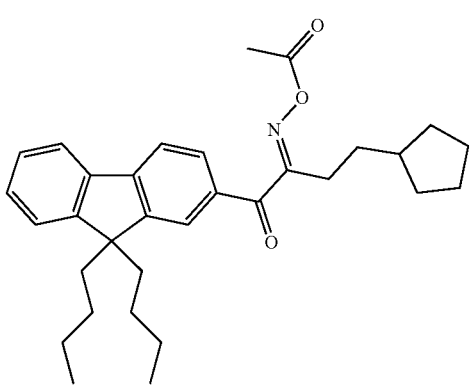
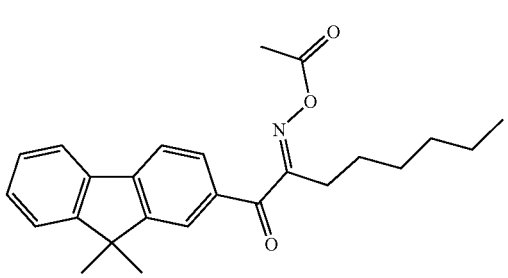

79
-continued
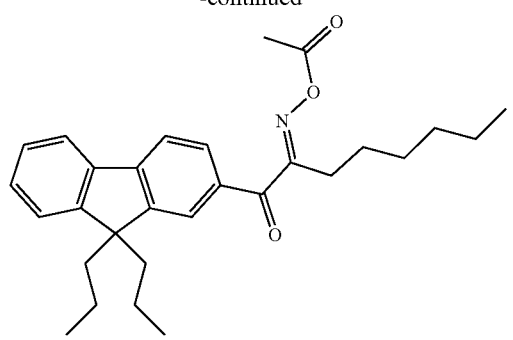
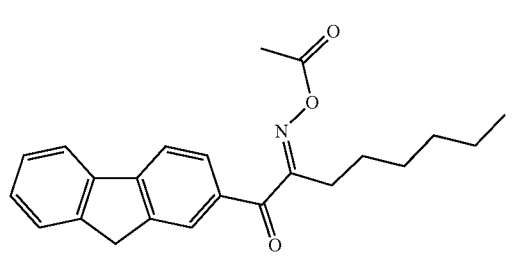
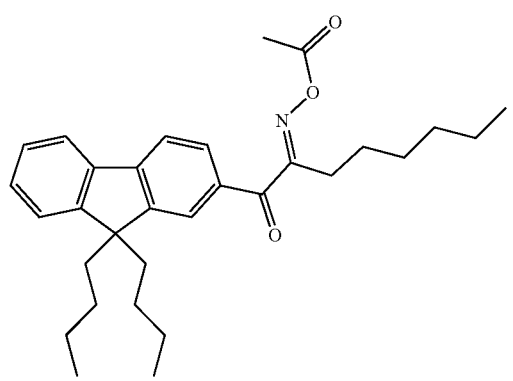
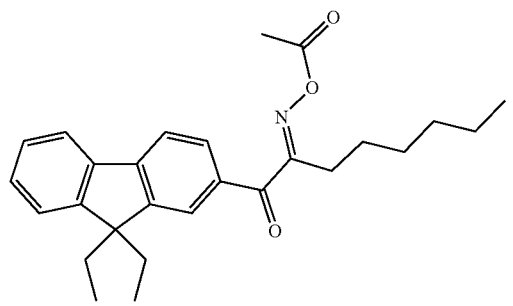
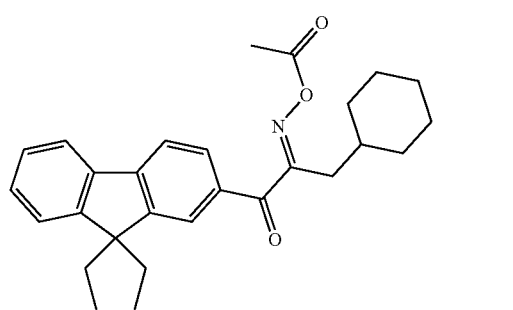
80
-continued
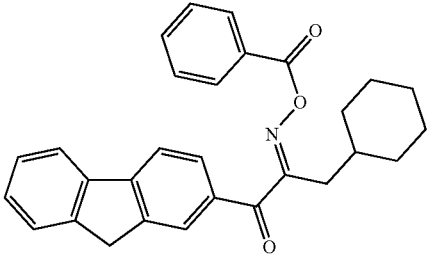
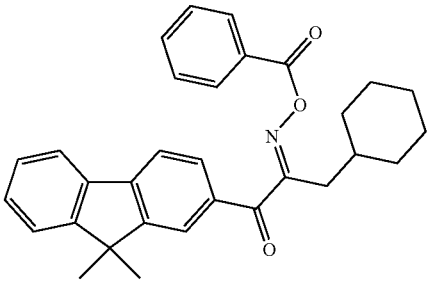
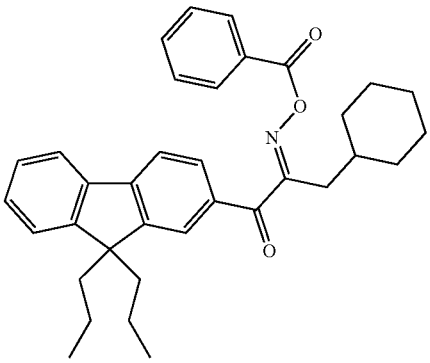
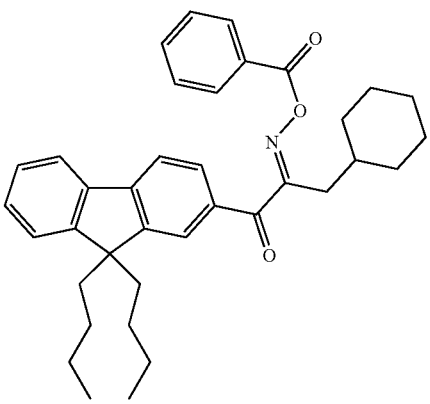
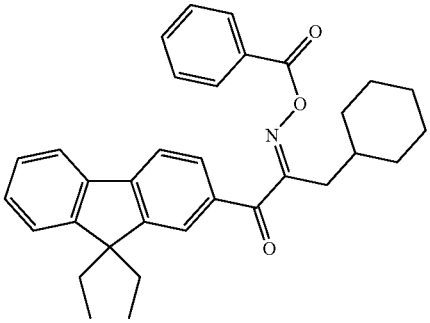

81
-continued
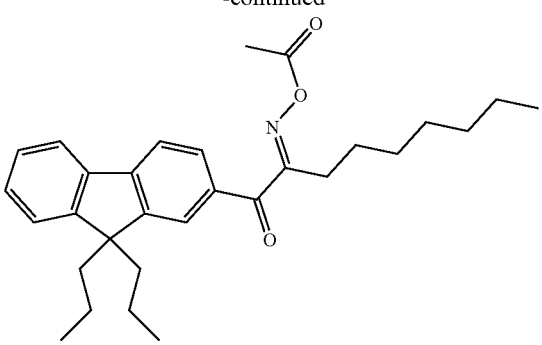
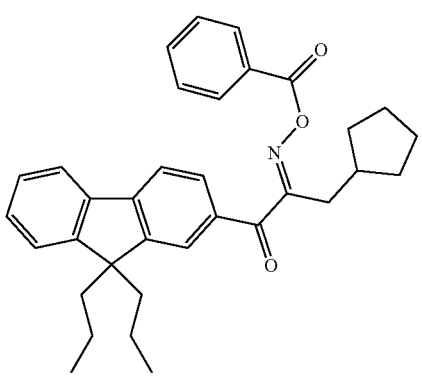
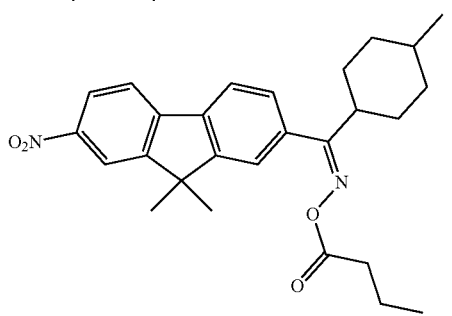
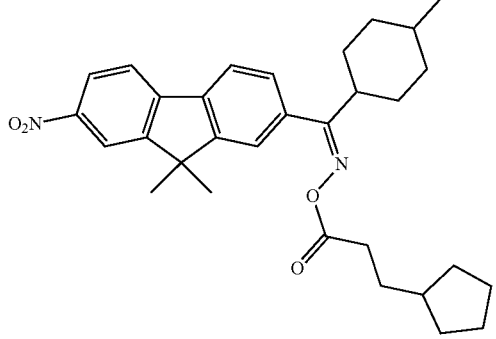
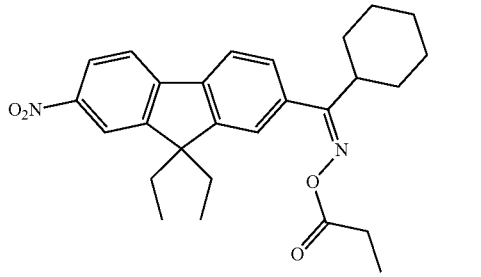
82
-continued
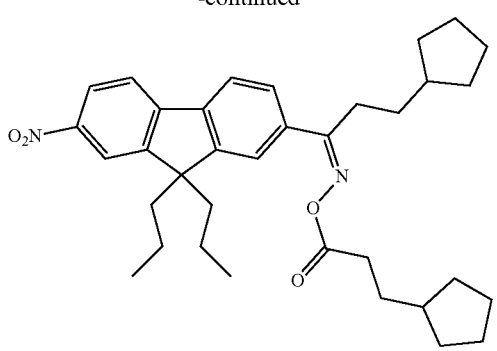
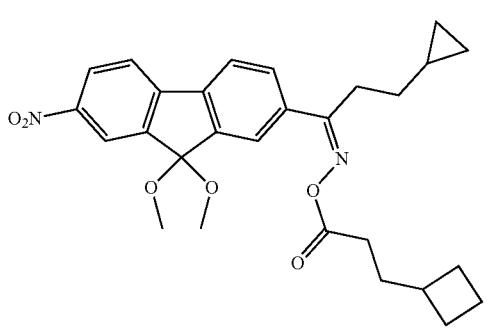
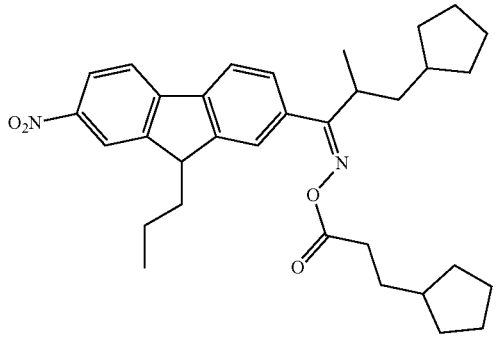
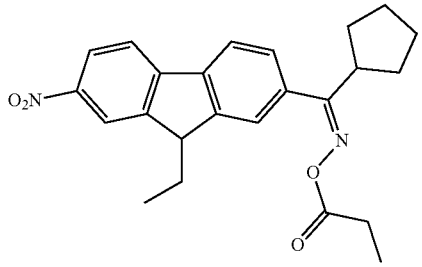
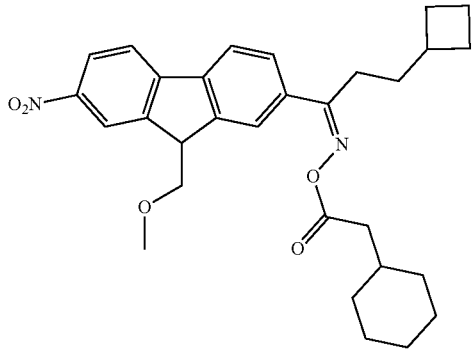

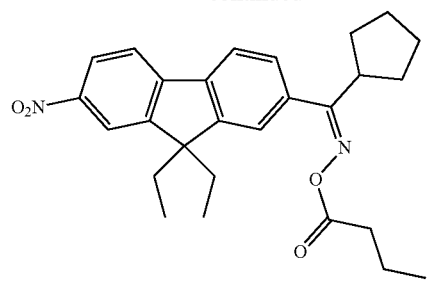
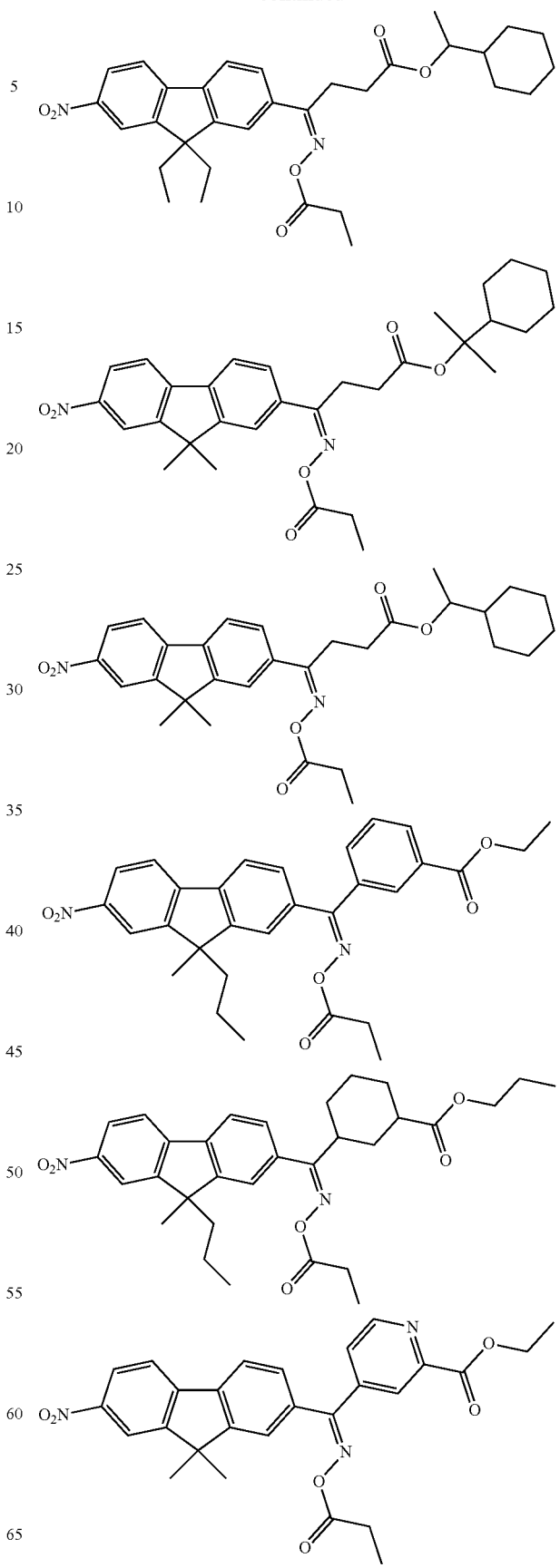

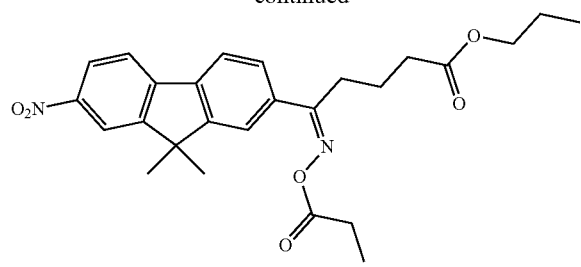
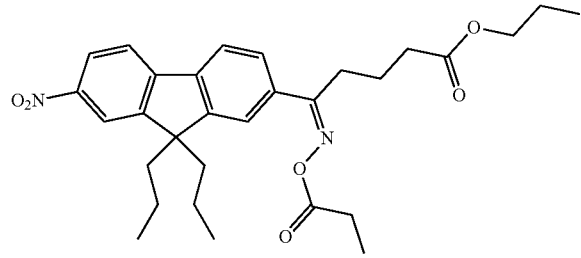
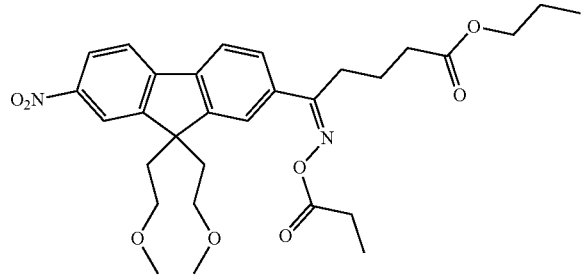
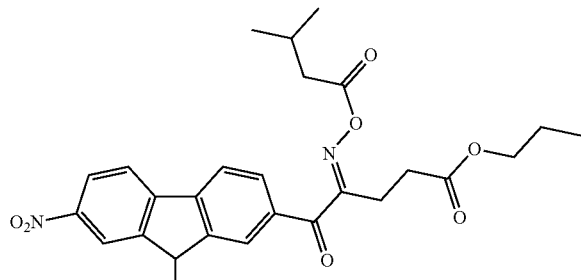
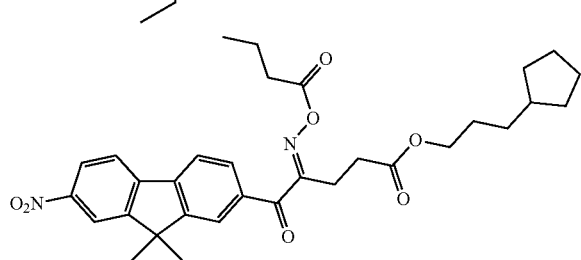
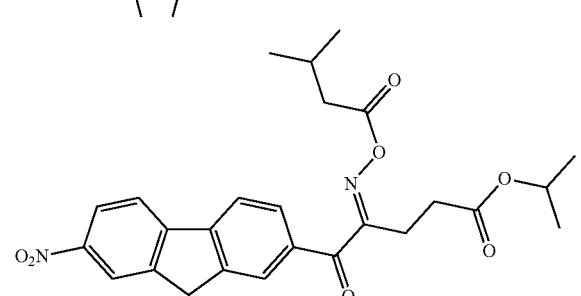
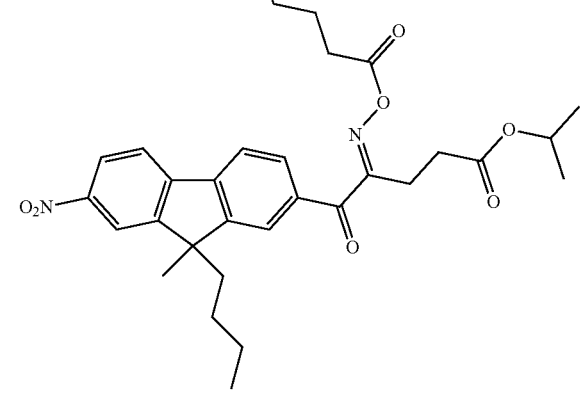
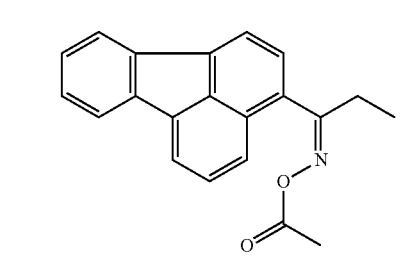
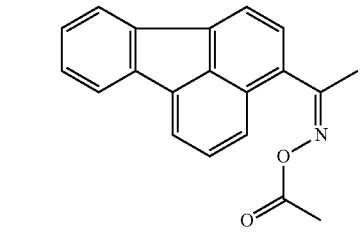
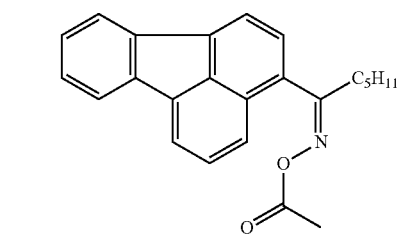
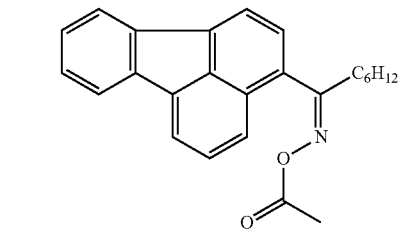
Preferable specific examples of the compound represented by the formula (c2) and having the group represented by the formula (c5) as $R^{c1}$ include following compounds.

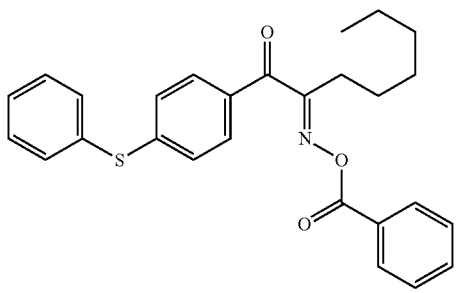

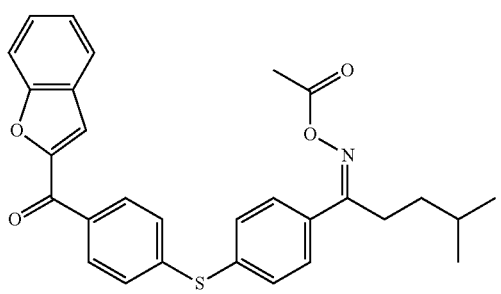

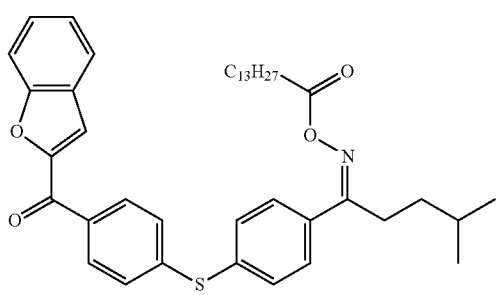

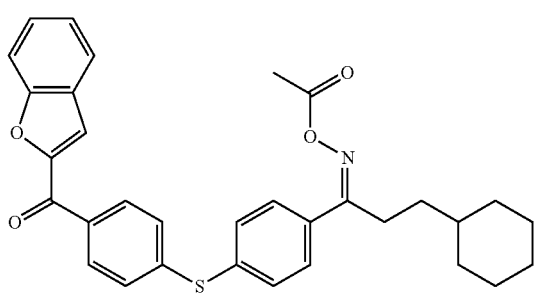

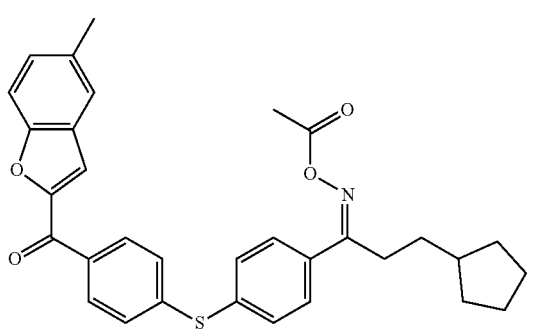

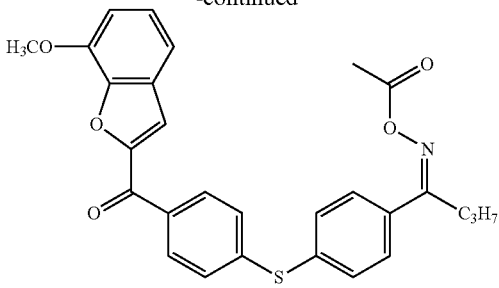

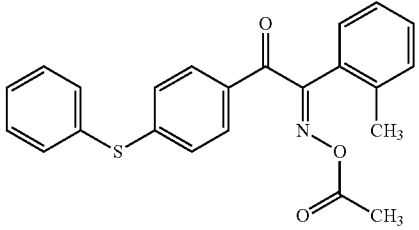 [SMILES: CC(=O)O/N=C(/C(=O)c1ccc(Sc2ccccc2)cc1)c1ccccc1C]

As a cationic polymerization initiator (C2), a conventionally known cationic polymerization initiator may be used without particular limitation. Typical examples of the cationic polymerization initiator (C2) can include onium salts. Examples of the cationic polymerization initiator (C2) include an oxonium salt, an ammonium salt, a phosphonium salt, a sulfonium salt, and an iodonium salt. A sulfonium salt and an iodonium salt are preferred, and a sulfonium salt is more preferred.

The content of the initiator (C) in the curable composition is not particularly limited. The content of the initiator (C) is appropriately determined depending on the type of radically polymerizable group or cationically polymerizable group, or on the type of initiator (C). The content of the initiator (C) in the curable composition relative to 100 parts by mass of the mass of the curable composition excluding the mass of the solvent (S) described later is preferably 0.01 parts by mass or more and 20 parts by mass or less, more preferably 0.1 parts by mass or more and 15 parts by mass or less, and even more preferably 1 part by mass or more and 10 parts by mass or less.

<Other Component>

The curable composition may contain various additives as needed, as components other than the components described above. Examples of the additive include a sensitizer, a curing accelerator, a filler, a dispersant, an adhesion promoter such as a silane coupling agent, an antioxidant, an antiaggregant agent, a thermal polymerization inhibitor, a defoaming agent, and a surfactant. As the filler, metal oxide particles such as titanium oxides and zirconium oxide particles are preferred from the viewpoint of the high refractive index of a cured product. The amount of these additives used is appropriately determined in consideration of the amount of these additives used in the curable composition.

<Solvent (S)>

The curable composition includes a solvent (S) for the purpose of adjustment of coatability and the like.

The solvent (S) includes triethylene glycol dimethyl ether. The solvent (S) essentially includes triethylene glycol dimethyl ether. Incorporation of triethylene glycol dimethyl ether in the curable composition facilitates favorable dissolution of the above-mentioned heterocyclic compound (A) in the curable composition. When the amount of the heterocyclic compound (A) to be dissolved in the curable composition can be increased, a cured product having a high refractive index is easily formed.

The solvent (S) may include, in addition to triethylene glycol dimethyl ether, an organic solvent other than triethylene glycol dimethyl ether as long as the desired effects are not impaired. The proportion of the mass of triethylene glycol dimethyl ether to the mass of the solvent (S) is preferably 50% by mass or more, more preferably 70% by mass or more, even more preferably 80% by mass or more, still even more preferably 90% by mass or more, still even more preferably 95% by mass or more, and particularly preferably 100% by mass.

Examples of other solvent other than triethylene glycol dimethyl ether as the solvent (S) include (poly)alkylene glycol monoalkyl ethers such as ethylene glycol monomethyl ether, ethylene glycol monoethyl ether, ethylene glycol n-propyl ether, ethylene glycol mono-n-butyl ether, diethylene glycol monomethyl ether, diethylene glycol monoethyl ether, diethylene glycol mono-n-propyl ether, diethylene glycol mono-n-butyl ether, triethylene glycol monomethyl ether, triethylene glycol monoethyl ether, propylene glycol monomethyl ether, propylene glycol monoethyl ether, propylene glycol mono-n-propyl ether, propylene glycol mono-n-butyl ether, dipropylene glycol monomethyl ether, dipropylene glycol monoethyl ether, dipropylene glycol mono-n-propyl ether, dipropylene glycol mono-n-butyl ether, tripropylene glycol monomethyl ether, and tripropylene glycol monoethyl ether; (poly)alkylene glycol monoalkyl ether acetates such as ethylene glycol monomethyl ether acetate, ethylene glycol monoethyl ether acetate, diethylene glycol monomethyl ether acetate, diethylene glycol monoethyl ether acetate, propylene glycol monomethyl ether acetate, and propylene glycol monoethyl ether acetate; other ethers such as diethylene glycol dimethyl ether, diethylene glycol methylethyl ether, diethylene glycol diethyl ether, and tetrahydrofuran; ketones such as methyl ethyl ketone, cyclohexanone, 2-heptanone, and 3-heptanone; alkyl lactates such as methyl 2-hydroxypropionate and ethyl 2-hydroxypropionate; other esters such as ethyl 2-hydroxy-2-methylpropionate, methyl 3-methoxypropionate, ethyl 3-methoxypropionate, methyl 3-ethoxypropionate, ethyl 3-ethoxypropionate, ethyl ethoxyacetate, ethyl hydroxyacetate, methyl 2-hydroxy-3-methylbutanoate, 3-methoxybutyl acetate, 3-methyl-3-methoxybutyl acetate, 3-methyl-3-methoxybutyl propionate, ethyl acetate, n-propyl acetate, isopropyl acetate, n-butyl acetate, isobutyl acetate, n-pentyl formate, isopentyl acetate, n-butyl propionate, ethyl butyrate, n-propyl butyrate, isopropyl butyrate, n-butyl butyrate, methyl pyruvate, ethyl pyruvate, n-propyl pyruvate, methyl acetoacetate, ethyl acetoacetate, and ethyl 2-oxobutanoate; aromatic hydrocarbons such as toluene and xylene; and amides such as N-methylpyrrolidone, N,N-dimethylformamide, and N,N-dimethylacetoamide. Among these other organic solvents, from the viewpoint of solubility of the heterocyclic compound (A), dipropylene glycol monomethyl ether acetate, and tripropylene glycol monomethyl ether are preferred.

The content of the solvent (S) is preferably an amount that achieves a solid content concentration of the curable composition of 1% by mass or more and 99% by mass or less, more preferably an amount that achieves a solid content concentration of the curable composition of 5% by mass or more and 50% by mass or less, and even more preferably an amount that achieves a solid content concentration of the curable composition of 10% by mass or more and 30% by mass or less.

<<Production Method of Cured Product>>

A cured product can be produced by shaping the curable composition described above into a desired shape and then subjecting the curable composition to light exposure or heating in accordance with the type of initiator (C). The shaping method is not particularly limited and appropriately selected depending on the shape of the cured product. Examples of the shaping method include coating and casting into a mold. Hereinafter, as a typical example of the production method of a cured product, a production method of a cured film will be described.

First, the curable composition is coated on a desired substrate to form a coating film. Then, as needed, the solvent (S) is at least partially removed from the coating film to form a coating film.

The method of coating the curable composition on the substrate is not particularly limited. The coating film can be formed by coating the curable composition on the substrate such that a desired film thickness is achieved, using a contact transfer-type applicator such as a roll coater, a reverse coater, a bar coater, or a slit coater, or a non-contact type applicator such as a spinner (a rotary applicator) or a curtain flow coater, for example.

When the curable composition includes the solvent (S), the coating film is preferably baked, as needed, to remove the solvent (S) at least partially from the coating film. The baking temperature is appropriately determined in consideration of the boiling point of the solvent (S) and the like. The baking may be carried out at a low temperature under reduced pressure conditions.

The method of baking is not particularly limited, and examples thereof include a method in which the coating film is dried using a hot plate at a temperature of 80° C. or higher and 150° C. or lower and preferably 85° C. or higher and 120° C. or lower, for 60 seconds or longer and 500 seconds or shorter.

The film thickness of the coating film formed as described above is not particularly limited. The film thickness of the coating film is appropriately determined depending on the applications of the cured film. The film thickness of the coating film is typically appropriately adjusted such that a cured film to be formed has a film thickness of preferably 0.1 µm or more and 10 µm or less and more preferably 0.2 µm or more and 5 µm or less.

When the curable composition includes a photosensitive initiator (C), a coating film is formed by the above method, and then the coating film is subjected to light exposure to thereby enable a cured film to be obtained.

The light exposure conditions for the coating film are not particularly limited as long as curing progresses favorably. Light exposure is carried out by irradiation with, for example, active energy rays such as ultraviolet rays and excimer laser light. The dose of energy used in the irradiation is not particularly limited, and examples thereof include a dose of 30 mJ/cm$^2$ or more and 5000 mJ/cm$^2$ or less. After the light exposure, the coating film subjected to light exposure may be baked in the same manner as the heating after coating.

When the curable composition includes a thermosensitive initiator (C), a coating film is formed by the above method, and then the coating film is heated to thereby enable a cured film to be obtained. The heating conditions are preferably 80° C. or higher and 280° C. or lower, and more preferably 120° C. or higher and 230° C. or lower. The heating time is, for example, preferably 5 minutes or longer and 12 hours or shorter, more preferably 10 minutes or longer and 6 hours or shorter, and particularly preferably 30 minutes or longer and 1 hour or shorter.

A cured product having a high refractive index can be formed in accordance with the above method. The refractive index of the cured product, as the refractive index for a light ray having a wavelength of 550 nm, is preferably 1.70 or more, and more preferably 1.73 or more. In addition, a cured product having a high light transmittance can be formed by the above method. The light transmittance of the cured product, as the light transmittance at a wavelength of 460 nm for a cured film having a film thickness of 1 μm, is preferably 90% or more, more preferably 92% or more, and particularly preferably 95% or more.

EXAMPLES

Hereinafter, the present invention is described in more detail by way of Examples, but the present invention is not limited to these Examples.

Preparation Example 1

To a reaction vessel having a volume of 300 ml, 3.91 g (0.027 mol) of 3-aminoquinoline and 200 mL of acetic acid were added. The inside of the reaction vessel was replaced by a nitrogen atmosphere, and then 5.00 g (0.027 mol) of cyanuric chloride was added to the reaction vessel at room temperature. Thereafter, 3-aminoquinoline was reacted with cyanuric chloride at room temperature for 2 hours. Subsequently, 6.51 g (0.060 mol) of 4-aminophenol was added to the reaction vessel, and the content of the reaction vessel was stirred at 110° C. for 3 hours. After the stirring was finished, 200 mL of water was added to the reaction liquid to precipitate a product. The precipitate was collected by filtration and then washed with ethanol. The washed precipitate was dried to obtain 8.80 g of an intermediate having the following structure.

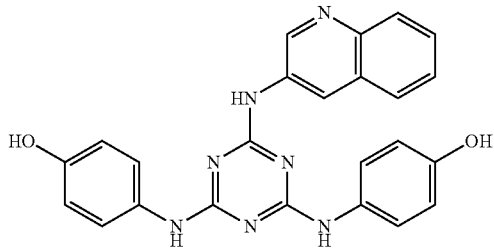 [SMILES: Oc1ccc(Nc2nc(Nc3ccc(O)cc3)nc(Nc3cnc4ccccc4c3)n2)cc1]

8.80 g (0.018 mol) of the intermediate obtained was mixed with 100 mL of N,N-dimethylacetamide to obtain a solution. The solution obtained was cooled in an ice bath. To the cooled solution, 4.97 g (0.055 mol) of acrylic chloride was added dropwise while the temperature of the solution was kept at 5° C. After acrylic chloride was added dropwise, the reaction liquid was stirred at room temperature for 3 hours. Next, 100 mL of water was added to the reaction liquid, and the precipitated solid was filtered off. The resulting precipitate was purified by silica gel chromatography to obtain 7.2 g of Compound A-4 having the following structure.

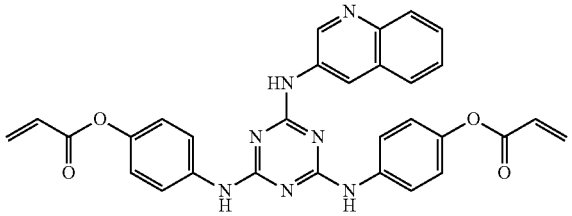

A-4

Preparation Example 2

Compound A-5 having the following structure was obtained in the same manner as in Preparation Example 1 except that 3-aminoquinoline was replaced by 2-mercapto-6-aminobenzothiazole.

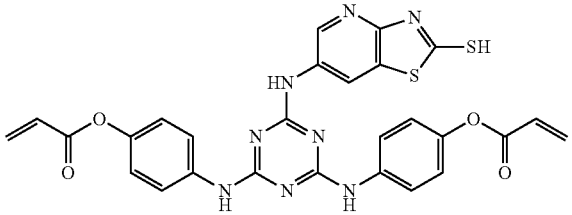

A-5

Preparation Example 3

To a reaction vessel having a volume of 300 mL, 2.53 g (0.027 mol) of aniline and 200 mL of acetic acid were added. The inside of the reaction vessel was replaced by a nitrogen atmosphere, and then 5.00 g (0.027 mol) of cyanuric chloride was added to the reaction vessel at room temperature. Thereafter, aniline was reacted with cyanuric chloride at room temperature for 2 hours. Subsequently, 7.05 g (0.060 mol) of 4-aminobenzonitrile was added to the reaction vessel, and the content of the reaction vessel was stirred at 110° C. for 3 hours. After the stirring was finished, 200 mL of water was added to the reaction liquid to precipitate a product. The precipitate was collected by filtration and then washed with ethanol. The washed precipitate was dried to obtain 7.303 g of Compound A-6 having the following structure.

$^1$H-NMR (CDCl$_3$): 7.02 (dd, 1H), 7.30-7.74 (m, 12H), 8.91 (s, 3H)

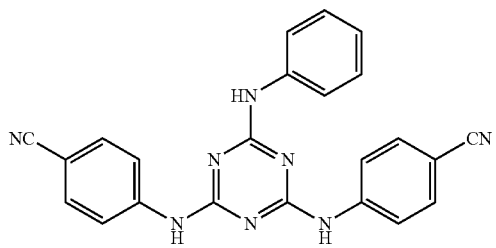

A-6

Example 1

Compound A-7 having the following structure was obtained in the same manner as in Preparation Example 3 except that aniline was replaced by 1-aminonaphthalene.

$^{1}$H-NMR (CDCl$_3$): 7.36-7.81 (m, 13H), 8.15 (d, 1H), 8.22 (d, 1H), 8.91 (s, 2H), 9.40 (s, 1H)

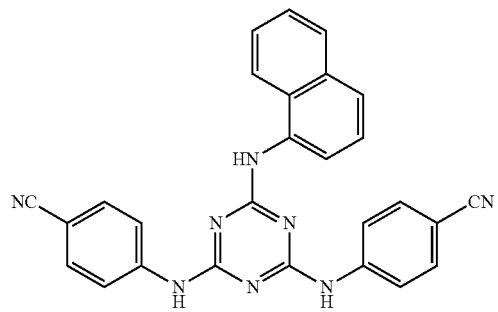

A-7

Example 2

Compound A-8 having the following structure was obtained in the same manner as in Preparation Example 3 except that aniline was replaced by 4-aminobenzonitrile and that 4-aminobenzonitrile was replaced by 1-aminonaphthalene.

$^{1}$H-NMR (CDCl$_3$): 7.36-7.82 (m, 14H), 8.15 (d, 2H), 8.22 (d, 2H), 8.91 (s, 2H), 9.43 (s, 1H)

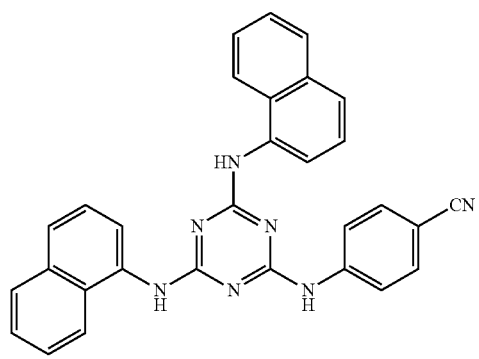

A-8

Example 3

Compound A-9 having the following structure was obtained in the same manner as in Preparation Example 3 except that aniline was replaced by 2-mercapto-6-aminobenzothiazole and that 4-aminobenzonitrile was replaced by 1-aminonaphthalene.

$^{1}$H-NMR (CDCl$_3$): 7.11 (d, 1H), 7.49-7.84 (m, 12H), 8.15 (d, 2H), 8.22 (d, 2H), 9.43 (s, 3H), 13.1 (s, 1H)

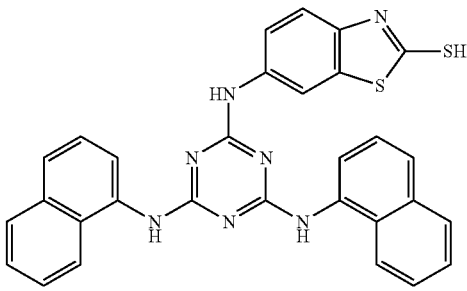

A-9

Compound A-4 to Compound A-6 and Compound A-7 to Compound A-9 obtained respectively in Preparation Examples 1 to 3 and Examples 1 to 3 and the following Compounds A-1, A-2, A-3, and A-10 to A-13 were used as samples to examine the solubility in triethylene glycol dimethyl ether and propylene glycol dimethyl ether according to the following method of each sample.

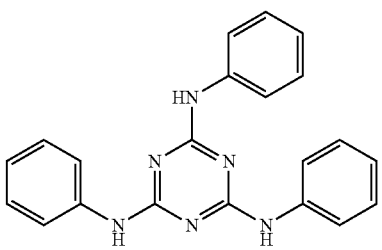

A-1

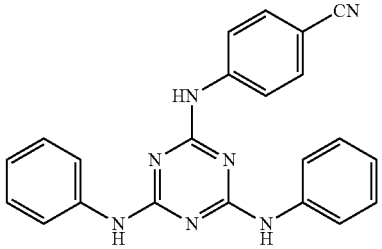

A-2

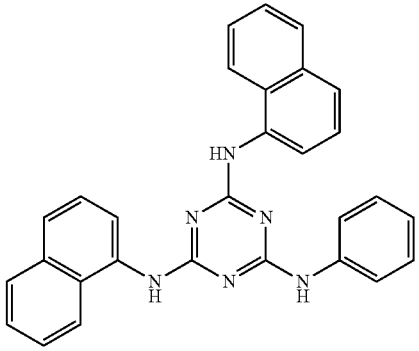

A-3

-continued

A-10
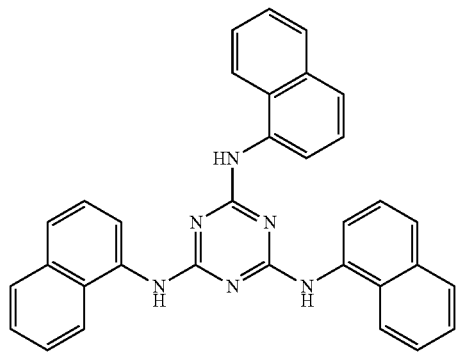

A-11
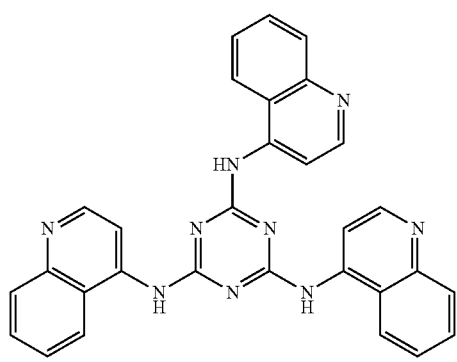

A-12
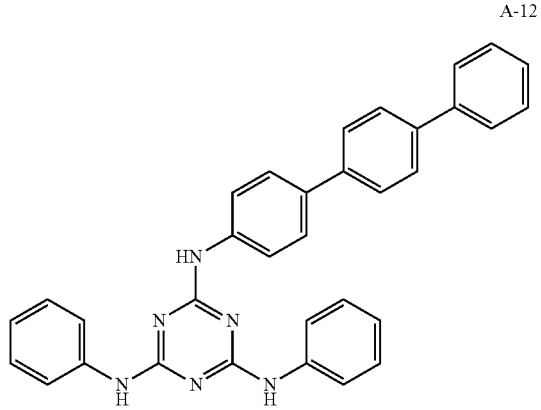

A-13
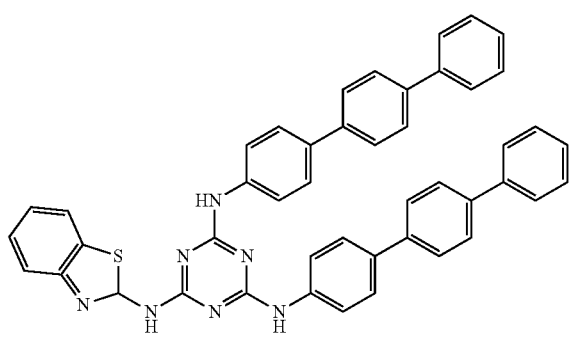

First, 1 g of each sample was added to 50 g of triethylene glycol dimethyl ether and to 50 g of propylene glycol monomethyl ether acetate at room temperature. Next, the sample in the solvent was stirred at 25° C. for an hour. Thereafter, the insoluble was removed with a filter made of teflon (R) having an opening size of 0.5 μm to obtain a solution of each sample. The concentration of each sample in the obtained solution was measured.

All of Compound A-1 to Compound A-li, which correspond to the compound represented by the formula (A1), each gave a solution thereof in triethylene glycol dimethyl ether at a concentration of 5% by mass or more. On the other hand, Compound A-12 and Compound A-13, which do not correspond to the compound represented by the formula (A1), each gave a solution thereof in triethylene glycol dimethyl ether at a concentration of 0.5% by mass or less. Compound A-1 to Compound A-7, Compound A-12, and Compound A-13 each gave a solution thereof in propylene glycol monomethyl ether acetate at a concentration of 0.5% by mass or less.

As described above, it can be seen that triethylene glycol dimethyl ether allows each of the compounds represented by the formula (A1) to be securely dissolved.

Examples 4 to 9, Comparative Example 1, and Comparative Example 2

In Examples 4 to 9, Compound A-1, Compound A-5, Compound A-6, and Compound A-8 to Compound A-10 mentioned above were used as the heterocyclic compound. In Comparative Example 1 and Comparative Example 2, Compound A-12 and Compound A-13 mentioned above were used as the heterocyclic compound.

In Examples 4 to 9, Comparative Example 1, and Comparative Example 2, a compound having the following structure was used as the photo radical polymerization initiator.

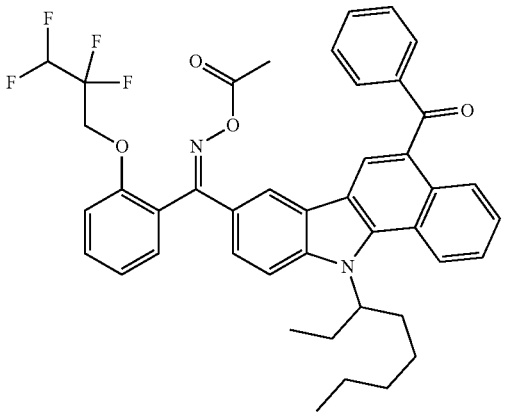 [SMILES: CCCCCC(CC)n1c2ccc(/C(=N\OC(C)=O)c3ccccc3OCC(F)(F)C(F)F)cc2c2cc(C(=O)c3ccccc3)c3ccccc3c21]

The curable compositions of Examples and Comparative Examples were each obtained by dissolving 89 parts by mass of a heterocyclic compound of the type described in Table 1, 10 parts by mass of dipentaerythritol hexaacrylate as the polymerizable compound, and 1 part by mass of the photo radical polymerization initiator at a solid concentration of 10% by mass in triethylene glycol dimethyl ether. The curable compositions obtained were used to carry out evaluation of the refractive index of the cured product, evaluation of the heat resistance of the cured product, evaluation of the surface appearance of the cured product, and the evaluation of the moisture resistance of cured product, in accordance with the following methods. These evaluation results are shown in Table 1.

<Measurement of Refractive Index>

The curable composition was coated onto a glass substrate using a spin coater. The film formed of the cured product was heated at 110° C. for 2 minutes to obtain a coating film having a thickness sufficient to form a cured film having a film thickness of 1 μm. The coating film obtained was subjected to light exposure using a high pressure mercury lamp such that the cumulative exposure amount reached 100 mJ/cm². The coating film after the light exposure was heated at 110° C. for 2 minutes to thereby obtain a cured film having a film thickness of 1 μm. The cured film obtained was subjected to refractive index measurement using a Prism Coupler manufactured by Metricon Corporation to determine the refractive index of the cured film at a wavelength of 550 nm. The refractive index was evaluated based on the measurement values in accordance with the following criteria.

Very Good: the refractive index is 1.70 or higher.
Good: the refractive index is 1.60 or higher and lower than 1.70.
Poor: the refractive index is lower than 1.60.

<Evaluation of Surface Appearance>

The surface of a cured film formed in the same manner as in measurement of refractive index was observed with an optical microscope. The surface appearance of the cured product was evaluated based on the evaluation results with the optical microscope in accordance with the following criteria.

Good: no roughness or cracks are observed on the surface.
Poor: roughness or cracks are observed on the surface.

<Evaluation of Heat Resistance>

The film thickness T0 at any position of a cured film formed in the same manner as in the measurement of refractive index was measured in μm to three decimal places. Subsequently, the cured film was heated at 200° C. for 30 minutes. After the heating, the film thickness T1 of the cured film was measured at the same position as in the measurement of the film thickness T0. The film thickness change rate was determined based on the measurement values of T0 and T1 according to the following expression.

Film thickness change rate (%)=|(T1−T0)/T0×100|

The heat resistance of the cured product was evaluated from the film thickness change rate determined in accordance with the following criteria.

Very Good: the film thickness change rate is less than 1%.
Good: the film thickness change rate is 1% or more and less than 3%.
Poor: the film thickness change rate is 3% or more.

<Evaluation of Moisture Resistance>

A cured film formed in the same manner as in the measurement of refractive index was placed in a constant temperature-humidity chamber and maintained under an atmosphere having a temperature of 85° C. and a relative humidity of 85% for 100 hours. The cured film sample after maintained in the high-temperature-and-high-humidity environment was observed with an optical microscope. The moisture resistance of the cured film was evaluated based on the observation results in accordance with the following criteria.

Very Good: no cracks or blisters are observed in the area observed of the surface of the cured product.
Good: 1 or more and 5 or less cracks or blisters are observed in the area observed of the surface of the cured product.
Poor: 6 or more cracks or blisters are observed in the area observed of the surface of the cured product.

TABLE 1

| | Heterocyclic compound | Refractive index 550 nm | Surface appearance | Heat resistance | Moisture resistance |
|---|---|---|---|---|---|
| Example 4 | A-1 | Good | Good | Good | Very Good |
| Example 5 | A-6 | Very Good | Good | Good | Good |
| Example 6 | A-5 | Very Good | Good | Very Good | Good |
| Example 7 | A-8 | Very Good | Good | Very Good | Good |
| Example 8 | A-9 | Very Good | Good | Very Good | Good |
| Example 9 | A-10 | Very Good | Good | Very Good | Very Good |
| Comparative example 1 | A-12 | Very Good | Poor | Good | Poor |
| Comparative example 2 | A-13 | Very Good | Poor | Poor | Poor |

According to Table 1, when the curable composition including the heterocyclic compound having a predetermined structure represented by the formula (A1) is used, it can be seen that a cured product having a high refractive index and having a favorable surface appearance, favorable heat resistance, and favorable moisture resistance can be formed. On the other hand, according to Table 1, when the structure of the heterocyclic compound does not correspond to the structure represented by the formula (A1), even if the curable composition includes the heterocyclic compound, it can be seen that a high refractive index cannot be exhibited and a favorable surface appearance and favorable moisture resistance are not achieved in the cured product.

What is claimed is:

1. A curable composition comprising a heterocyclic compound (A), an initiator (C), and a solvent (S), wherein the heterocyclic compound (A) is a compound represented by the following formula (A1):

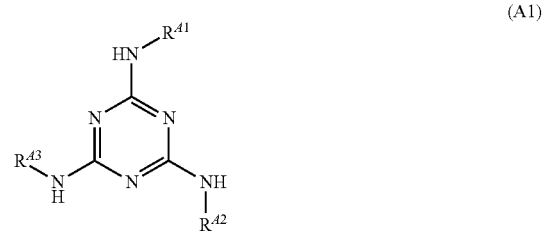

wherein $R^{A1}$, $R^{A2}$, and $R^{A3}$ are each independently an optionally substituted monocyclic aromatic group or an optionally substituted condensed aromatic group, when the monocyclic aromatic group or the condensed aromatic group has a substituent, the substituent does not contain an aromatic ring, and three —NH-groups bonded to the triazine ring each are bonded to the aromatic ring in the $R^{A1}$, the $R^{A2}$, and the $R^{A3}$;

when the heterocyclic compound (A) has a polymerizable group, the curable composition comprises or does not comprise a polymerizable compound (B) other than the heterocyclic compound (A);

when the heterocyclic compound (A) has no polymerizable group, the curable composition comprises a polymerizable compound (B) other than the heterocyclic compound (A); the polymerizable group is a radically polymerizable group-containing group or a cationically polymerizable group-containing group;

when the curable composition comprises the heterocyclic compound (A) having the polymerizable group and the polymerizable compound (B), the polymerizable group possessed by the heterocyclic compound (A) and the polymerizable group possessed by the polymerizable compound (B) each is a radically polymerizable group-containing group or a cationically polymerizable group-containing group; and the solvent (S) comprises triethylene glycol dimethyl ether.

2. The curable composition according to claim 1, comprising the polymerizable compound (B).

3. The curable composition according to claim 1, wherein the curable composition comprises the heterocyclic compound (A) having the radically polymerizable group or comprises the heterocyclic compound (A) having the radically polymerizable group and the polymerizable compound (B) having the radically polymerizable group, and the radically polymerizable group comprises a (meth) acryloyl group.

4. The curable composition according to claim 1, wherein at least one of the $R^{41}$, the $R^{42}$, and the $R^{43}$ is the optionally substituted condensed aromatic group.

5. The curable composition according to claim 1, wherein at least one of the $R^{41}$, the $R^{42}$, and the $R^{43}$ is an optionally substituted bicyclic condensed aromatic group.

6. The curable composition according to claim 4, wherein at least one of the $R^{41}$, the $R^{42}$, and the $R^{43}$ is an optionally substituted naphthalen-1-yl group.

7. The curable composition according to claim 6, wherein one or two of the $R^{41}$, the $R^{42}$, and the $R^{43}$ is are an optionally substituted naphthalen-1-yl group(s), and one or two of the $R^{41}$, the $R^{42}$, and the $R^{43}$ is are a 4-cyanophenyl group(s) or a benzothiazolyl group(s).

8. A cured product of the curable composition according to claim 1.

9. A compound represented by the following formula (A1):

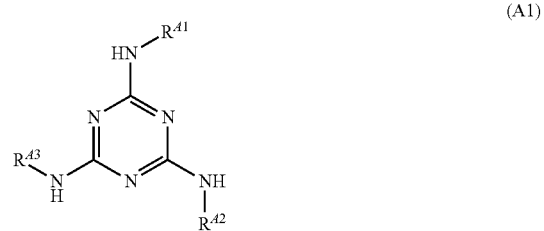

wherein one or two of $R^{41}$, the $R^{42}$, and the $R^{43}$ is are an optionally substituted naphthyl group(s), and one or two of the $R^{41}$, the $R^{42}$, and the $R^{43}$ is are a 4-cyanophenyl group(s) or a benzothiazolyl group(s).

10. The compound according to claim 9, wherein the naphthyl group is a naphthalen-1-yl group.

* * * * *